(12) United States Patent
Lee

(10) Patent No.: US 7,973,214 B2
(45) Date of Patent: Jul. 5, 2011

(54) DESIGNER ORGANISMS FOR PHOTOSYNTHETIC PRODUCTION OF ETHANOL FROM CARBON DIOXIDE AND WATER

(75) Inventor: James Weifu Lee, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 741 days.

(21) Appl. No.: 11/903,919

(22) Filed: Sep. 25, 2007

(65) Prior Publication Data

US 2008/0176304 A1 Jul. 24, 2008

Related U.S. Application Data

(60) Provisional application No. 60/826,806, filed on Sep. 25, 2006.

(51) Int. Cl.
*A01H 5/00* (2006.01)
*C12N 15/52* (2006.01)
*C12N 15/82* (2006.01)

(52) U.S. Cl. ........ 800/284; 800/288; 800/295; 800/296; 800/298; 435/257.2; 435/419; 435/468

(58) Field of Classification Search .................. None
See application file for complete search history.

(56) References Cited

U.S. PATENT DOCUMENTS

| | | | | |
|---|---|---|---|---|
| 5,270,175 | A * | 12/1993 | Moll | .............................. 435/41 |
| 6,699,696 | B2 | 3/2004 | Woods et al. | |
| 2002/0042111 | A1 | 4/2002 | Woods et al. | |

OTHER PUBLICATIONS

Deng M. et al. Applied and Environmental Microbiology, Feb. 1999; vol. 65, No. 2; pp. 523-528.*
Deng M. et al. Applied and Environmental Microbiology, Feb. 1999; p. 523-528.*
Greller R.P. et al., "Fermentative Metabolism of *Chlamydomonas Reinhardtii*", *Plant Physiol.* 75:212-218 (1984).
Cinco R.M. et al., "The Role of Carbon Dioxide in Light-Activated Hydrogen Production by *Chlamydomonas Reinhardtii*", *Photosynthesis Research* 38:27-33 (1993).
Quinn J.M. et al., "Coordinate Copper-and Oxygen-Responsive *Cyc6* and *Cpx1* Expression in *Chlamydomonas* is Mediated by the Same Element", *The Journal of Biological Chemistry* 275(9):6080-6089 (2000).
Teramoto H. et al., "Identification of *Lhcb* Gene Family Encoding the Light-Harvesting Chlorophyll-*a/b* Proteins of Photosystem II in *Chlamydomonas Reinhardtii*", *Plant Cell Physiol.* 42(8):849-856 (2001).
Pattanayak D. et al., "Nicotinamide Adenine Dinucleotide Phosphate Phosphatase Facilitates Dark Reduction of Nitrate: Regulation by Nitrate and Ammonia", *Biologia Plantarum* 41(1):75-84 (1998).
Muto S. et al., "Light-Induced Conversion of Nicotinamide Adenine Dinucleotide to Nicotinamide Adenine Dinucleotide Phosphate in Higher Plant Leaves", *Plant Physiol.* 68(2):324-328 (1981).
Matsumura-Kadota H. et al., "Light-Induced Conversion of $NAD^+$ to $NADP^+$ in *Chlorella* Cells", *Biochimica et Biophysica Acta* 679(2):300-307 (1982).
Liszewski K., "Progress in RNA Interference", *Generic Engineering News* 23(11):pp. 1, 11, 12, 14, 15 and 59 (2003).
Fire A. et al., "Potent and Specific Genetic Interference by Double-Stranded RNA in *Caenorhabditis Elegans*", *Nature* 391(6669):806-811 (1998).
Dykxhoorn D.M. et al., "Killing the Messenger: Short RNAs that Silence Gene Expression", *Nature Reviews Molecular Cell Biology* 4(6):457-467 (2003).
Lee J.W. et al., "Temperature Effect on Production of Hydrogen and Oxygen by *Chlamydomonas* Cold Strain CCMP1619 and Wild-Type 137c", *Applied Biochemistry and Biotechnology* 51/52:379-386 (1995).
Lee J.W. et al., "Improvement of Photosynethetic $CO_2$ Fixation at High Light intensity Through Reduction of Chlorophyll Antenna Size", *Applied Biochemistry and Biotechnology* 98-100:37-48 (2002).
Loppes R. et al., "Two Short Regions of the Promoter are Essential for Activation and Repression of the Nitrate Reductase Gene in *Chlamydomonas Reinhardtii*", *Mol. Genet. Genomics* 268:42-48 (2002).
Keppetipola S. et al., "Rapid Detection of in vitro Expressed Proteins Using Lumio Technology", *Gene Expression* 25.3:7-11 (2003).
Fuhrmann M. et al., "The Abundant Retinal Protein of the *Chlamydomonas* Eye is Not the Photoreceptor for Phototaxis and Photophobic Responses", *Journal of Cell Science* 114:3857-3863 (2001).
Schroda M. et al., "The *HSP70A* Promoter as a Tool for the Improved Expression of Transgenes in *Chlamydomonas*", *The Plant Journal* 21(2):121-131 (2000).
Griffin B.A. et al., "Specific Covalent Labeling of Recombinant Protein Molecules Inside Live Cells", *Science* 281:269-272 (1998).
Deng Ming-De et al., "Ethanol Synthesis by Genetic Engineering in Cyanobacteria", *Applied and Environmental Microbiology* 65(2):523-528 (1999).
Matsunaga T. et al., "Marine Microalgae", *Adv. Biochem Engin/Biotechnol* 96: 165-188 (2005).

* cited by examiner

*Primary Examiner* — Russell Kallis
(74) *Attorney, Agent, or Firm* — Scully, Scott, Murphy & Presser, P.C.

(57) ABSTRACT

The present invention provides a revolutionary photosynthetic ethanol production technology based on designer transgenic plants, algae, or plant cells. The designer plants, designer algae, and designer plant cells are created such that the endogenous photosynthesis regulation mechanism is tamed, and the reducing power (NADPH) and energy (ATP) acquired from the photosynthetic water splitting and proton gradient-coupled electron transport process are used for immediate synthesis of ethanol ($CH_3CH_2OH$) directly from carbon dioxide ($CO_2$) and water ($H_2O$). The ethanol production methods of the present invention completely eliminate the problem of recalcitrant lignocellulosics by bypassing the bottleneck problem of the biomass technology. The photosynthetic ethanol-production technology of the present invention is expected to have a much higher solar-to-ethanol energy-conversion efficiency than the current technology and could also help protect the Earth's environment from the dangerous accumulation of $CO_2$ in the atmosphere.

17 Claims, 16 Drawing Sheets

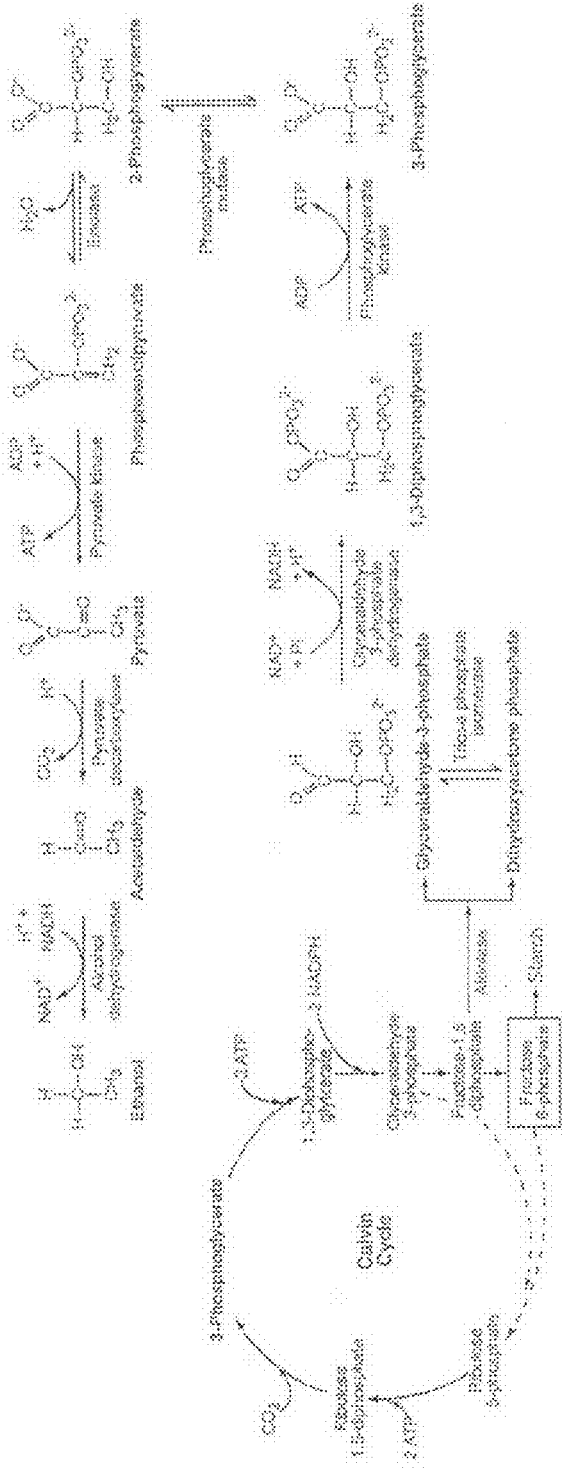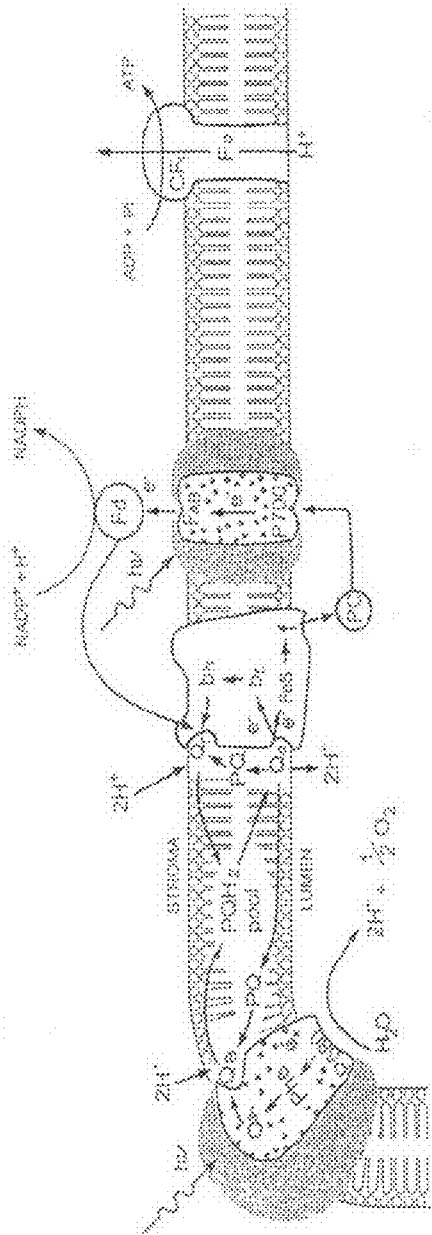
FIG. 4D

| PCR FD Primer | Inducible Promoter | Targeting Sequence | Ethanol-Production Pathway Gene(s) | PCR RE Primer |

FIG. 6A

| PCR FD Primer | Inducible Promoter | Targeting Sequence | NADPH/NADH-conversion designer gene(s) | PCR RE Primer |

FIG. 6B

| PCR FD Primer | Inducible Promoter | iRNA Starch-Synthesis Inhibitor(s) | PCR RE Primer |

FIG. 6C

| PCR FD Primer | Inducible Promoter | Starch-Synthase iRNA Sequence | Terminator | PCR RE Primer |

FIG. 6D

| PCR FD Primer | Inducible Promoter | G-1-P Adenylyltransferase iRNA Sequence | Terminator | PCR RE Primer |

FIG. 6E

| PCR FD Primer | Inducible Promoter | Phosphoglucomutase iRNA Sequence | Terminator | PCR RE Primer |

FIG. 6F

| PCR FD Primer | Inducible Promoter | Targeting Sequence | Starch-Degradation-Glycolysis Gene(s) | PCR RE Primer |

FIG. 6G

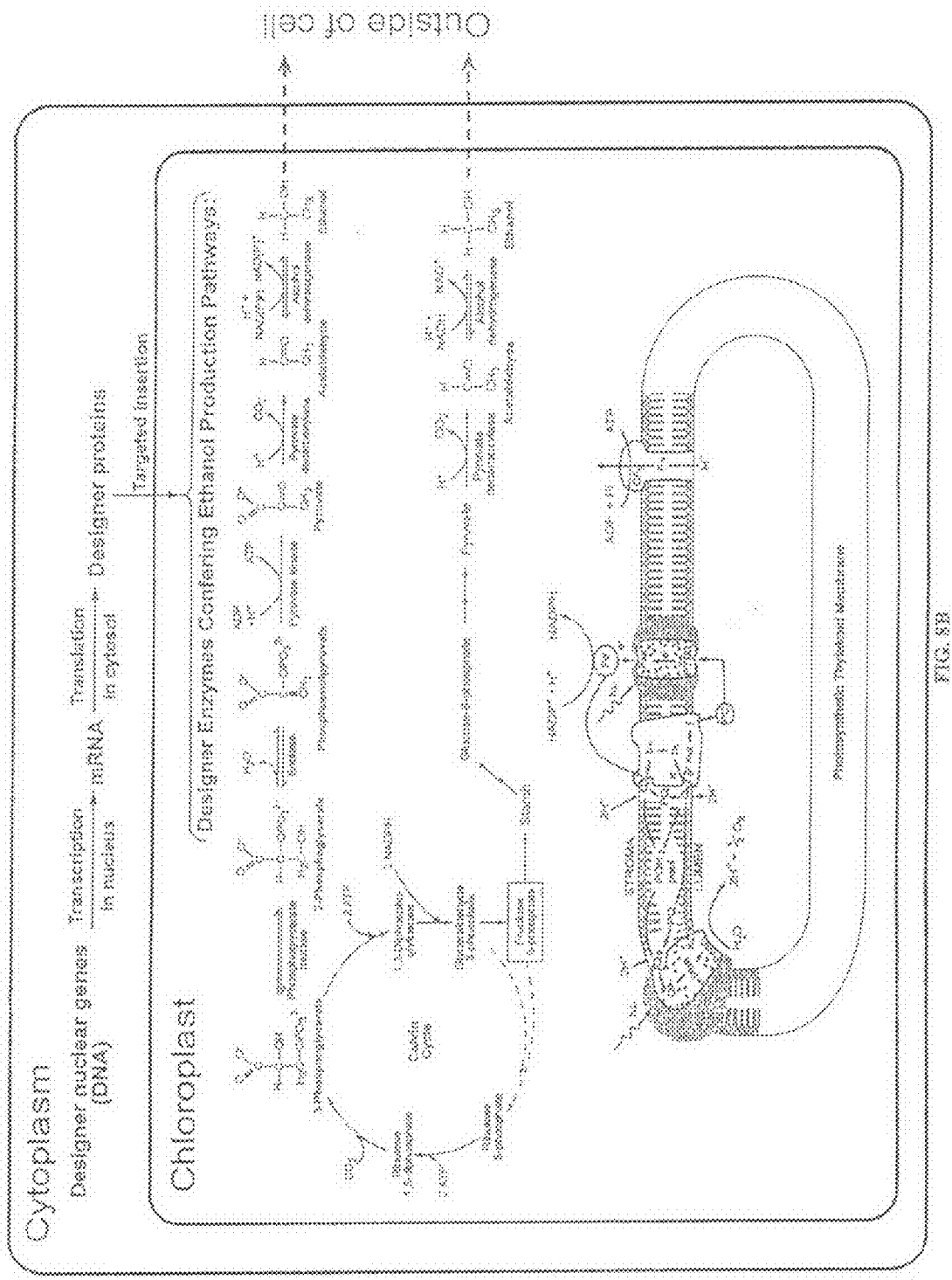

SEQUENCE LISTING

```
<160> NUMBER OF SEQ ID NOS: 28

<210> SEQ ID NO 1
<211> LENGTH: 1677
<212> TYPE: DNA
<213> ORGANISM: Artificial Sequence
<220> FEATURE:
<223> OTHER INFORMATION: Synthetic oligonucleotide

<400> SEQUENCE: 1
agaaaatctg gcaccacacc tatatggtag ggtgcgagtg accccgcgcg acttggagct      60
cgatggcccc gggttgtttg gggcgtccgc ctctcgcgct attctgagct ggagaccgag     120
gcgcatgaaa atgcattcgc ttccatagga cgctgcattg tggcttgaag gttcaaggga     180
agggttcaaa cgacccccgcc gtacgaactt ttgtcggggg gcgctcccgg ccccgggctc     240
ttgtgcgcgc attagggctt cgggtcgcaa gcaagacgat acatggccgc cgtcattgcc     300
aagtcctccg tctccgcggc cgtggctcgc ccggcccgct ccagcgtgcg ccccatggcc     360
gcgctgaagc ccgccgtcaa ggctgccccc gtggctgccc cggctcaggc caaccagatg     420
gctcccatca agatcggcat caatggtttt ggtcgtattg gccgcctcgt gtggcgtgcc     480
actcttaacc gtgacgatgt cgaggtcgtc gccatcaatg atccattcat tgatgtgcca     540
tacatggtct acatggccaa gtatgactcg gtccacggca acctgaccca cgacgttcag     600
caaggcgacg gcaagctgat ggtcaatggc aagtcaatca ccatcttcgg caagatggat     660
gccaaggaga tcccatggaa ggaggccggc gcgaccttcg tcgttgagtc gactggtgtg     720
ttcaccaccc tggagggcgc cagctctcac ctggtcggcg gtgctgagac cgtcgtcatc     780
tccgccccat caaacgatgc ccccatgttc gtcatgggtg tcaacgagga gggctacaag     840
ccagacatga aagtggtgtc caacgcgtct tgcaccacca ctgcctggg ccccctggcc     900 aaggtcatcc accttaagtt cggcatcctg gagggcctga tgaccaccgt ccacgcgacc     960
accgccaccc agaagaccgt cgacgggccg tccaagaagg actggcgcgg cgggcgcggc    1020
atcctggaca acatcatccc ctcggcgact ggtgccgcca aggccgtcgg caaggtgctg    1080
```

```
cctgccctga acggcaagct caccggcatg gccttccgcg tgcccacccc cgatgtctcg    1140
gtcgtcgatc tgaccgtgcg cctggagaag ggtgcgtcgt acgacgccat caaggccgag    1200
atcaagcgcg cgagcgagaa cgagctcaag ggcatcctgg cctacaccga ggatgccgtg    1260
gtctccaccg acttcatcgg caacaagcac agctccatct tcgacgccga ggccggcatc    1320
gccctcaacg acaactttgt caagctggtc tcctggtacg acaacgagtg gggctactcc    1380
aaccgtgtcg tcgacctgat cgcgcacatg gccaaggtca aggccgccag ccactaaatg    1440
gaggcgctcg ttgatctgag ccttgccccc tgacgaacgg cggtggatgg aagatactgc    1500
tctcaagtgc tgaagcggta gcttagctcc ccgtttcgtg ctgatcagtc ttttttcaaca    1560 cgtaaaaagc ggaggagttt tgcaattttg ttggttgtaa cgatcctccg ttgattttgg    1620
cctctttctc catgggcggg ctgggcgtat ttgaagcggt tctctcttct gccgtta       1677

<210> SEQ ID NO 2
<211> LENGTH: 1908
<212> TYPE: DNA
<213> ORGANISM: Artificial Sequence
<220> FEATURE:
<223> OTHER INFORMATION: Synthetic oligonucleotide

<400> SEQUENCE: 2
agaaaatctg gcaccacacc tatatggtag ggtgcgagtg accccgcgcg acttggagct      60
cgatggcccc gggttgtttg gggcgtccgc ctctcgcgct attctgagct ggagaccgag     120
gcgcatgaaa atgcattcgc ttccatagga cgctgcattg tggcttgaag gttcaaggga     180
agggttcaaa cgaccccgcc gtacgaactt ttgtcggggg gcgctcccgg ccccgggctc     240
ttgtgcgcgc attagggctt cgggtcgcaa gcaagacgat acatggccct ctctatgaag     300
atgcgcgcca acgcgcgcgt gtccggtcgc cgcgtcgccg ctgtggcccc ccgcgtggtg     360
cccttctcgt cggcctccag ctccgtgctg cgctctggct tcgcgctgag gtgtctgtgg     420
acatccgccg cgtgggccgc tctcgcatcc gtcgtcgagg cggtgaagaa gtcggttggc     480
gacctgcaca aggctgacct ggagggcaag gcgcgtgttcg tccgcgcgga cctgaacgtg     540
cctcttgaca aggccaccct ggccatcacc gacgacaccc gcattcgcgc ggccgtcccc     600
accctgaagt acctgctgga caacggtgct aaggtcctgc tgacctcgca cctgggtcgc     660
ccgaagggcg gtcccgagga caagtaccgc ctgaccccccg tggtggcccg cctgtcggag     720
ctgctgggca gcccgtgac caaggtcgat gactgcatcg gccccgaggt ggagaaggcg     780
gtgggcgcca tgaagaacgg cgagctgctg ctgctggaga actgccgctt ctacaaggag     840
gaggagaaga cgagcccga gttcgccaag aagctggccg ccaacgccga cctgtacgtg     900
aacgacgcgt tcggcactgc ccaccgcgcc cacgcctcca ccgagggtgt gaccaagttc     960
ctgaagccct ccgtggccgg cttcctgctg cagaaggagc tggactacct tgatggcgcc    1020
gtgtccaacc ccaagcgccc cttcgtggcc attgtgggcg gctccaaggt gtcctccaag    1080
atcaccgtca ttgaggcgct gatggagaag tgcgacaaga tcatcatcgg cggtggcatg    1140
atcttcacct tctacaaggc ccgcgcgctg aaggtgggct cctcgctggt tgaggacgac    1200
aagatcgagc tggccaagaa gctggaggag atggccaagg ccaagggtgt gcagctgctg    1260
ctgcccaccg acgtggtggt ggccgacaag ttcgacgcca cgccaacac ccagaccgtg    1320 cccatcaccg ccatccccga tggctggatg ggtctggaca ttggcccgga ctccgtcaag    1380
accttcaacg acgccctggc cgacgccaag accgttgtgt ggaacggccc catgggtgtg    1440
ttcgagtttc cccaagttcg ccaacgcacc gtgtcgatcg ccaacaccct ggccggcctg    1500
```

| | |
|---|---|
| acgcccaagg gctgcatcac catcattggt ggcggtgact ccgtggctgc cgtcgagcag | 1560 |
| gccggcgttg ccgagaagat gagccacatc tccaccggcg gcggtgcctc cctggagctg | 1620 |
| ctggagggca aggtcctgcc cggcgtggcc gccctgacg agaagtaaat ggaggcgctc | 1680 |
| gttgatctga gccttgcccc ctgacgaacg gcggtggatg aagatactg ctctcaagtg | 1740 |
| ctgaagcggt agcttagctc cccgtttcgt gctgatcagt cttttcaac acgtaaaaag | 1800 |
| cggaggagtt ttgcaatttt gttggttgta acgatcctcc gttgattttg gcctctttct | 1860 |
| ccatgggcgg gctgggcgta tttgaagcgg ttctctcttc tgccgtta | 1908 |

<210> SEQ ID NO 3
<211> LENGTH: 2349
<212> TYPE: DNA
<213> ORGANISM: Artificial Sequence
<220> FEATURE:
<223> OTHER INFORMATION: Synthetic oligonucleotide

<400> SEQUENCE: 3

| | |
|---|---|
| agaaaatctg gcaccacacc tatatggtag ggtgcgagtg accccgcgcg acttggagct | 60 |
| cgatggcccc gggttgtttg gggcgtccgc ctctcgcgct attctgagct ggagaccgag | 120 |
| gcgcatgaaa atgcattcgc ttccatagga cgctgcattg tggcttgaag gttcaaggga | 180 |
| agggttcaaa cgaccccgcc gtacgaactt ttgtcggggg gcgctcccgg ccccgggctc | 240 |
| ttgtgcgcgc attagggctt cgggtcgcaa gcaagacgat acctcgagca tatggccgcc | 300 |
| gtcattgcca agtcctccgt ctccgcggcc gtggctcgcc cggcccgctc cagcgtgcgc | 360 |
| cccatggccg cgctgaagcc cgccgtcaag gctgccccg tggctgcccc ggctcaggcc | 420 |
| aaccagatgg cgcacgacta caagctgaag gcccacccgg cgattcctgc gcccgagggc | 480 |
| ccgctgctgg tctgcattct ggacggcttc ggcgagaacg agtacaagga tgagttcaac | 540 |
| gccgtgcacg tggctaagac gcccactgtg gacgcgctgc gcgctgtgcc ccatcgcttc | 600 |
| cgttccatca aggcgcacgg aaaggctgtg ggcctgccca gcgatgccga catgggcaac | 660 |
| agcgaggtgg ggcacaacgc cctgggctcg ggccaggtgg tggaccaagg cgcgcgcctg | 720 |
| gtggacctgg cgctggagac cggccgtatg ttctcggacc ccggctggaa gctcatcagc | 780 |
| gaggccttcc cctcccacac cgtccacttc atcggcctgc tgtccgacgg cggcgtgcac | 840 |
| tcgcgcgccg atcagctgca cggctgcctg cgcggcgccg tggagcgcgg cgccaagcgc | 900 |
| gtgcgcgtgc acatcctgac tgacggccgc gacgtgccgg acggcagcag catccggttc | 960 |
| gtggaggagc tggaggcggt gctggcggag ctgcgcggca agggctgcga catcgccatc | 1020 |
| gcctcgggcg gcggccgcat gcaggtcacc atggaccgct acgaggcgga ctggagcatg | 1080 |
| gtgaagcgcg gctgggacgc gcacgtgctg ggcaaggcgc ccactactt caaggacgcc | 1140 |
| aagaccgcgg tcaccaccct gcgcggctcc gaggacgcgc cggtgtctga ccagtacgtg | 1200 |
| gccccctttg tgattgtgga cgaggcggac aagccggtgg gcaccattga ggacggcgac | 1260 |
| gcggtggtgc tgttcaactt ccgcgcggac cgcatggtgg agatcagcaa ggccttcgag | 1320 |
| tacgaggacg gcttcaccgc cttttgagcgc gagcgcttcc ccaagggcct gcgcttcgtg | 1380 |
| ggcatgatgc agtacgacgg cgacctgaag ctgcccgcca acttcctggt gccgccgccc | 1440 |
| ctgattgagc acgtgtcggg cgagtacctg tgcaagaacg ggctgagcac cttcgcctgc | 1500 |
| tccgagactc agaagttcgg gcagtgacg ttcttctgga acggcaaccg ctccggctac | 1560 |
| ctggacgcca gcaggagca gtacctggag atcccgtcgg acaagatcga gttcaacaag | 1620 |
| gctccggaca tgaaggcgcg cgagatcacc gccgccggca ttgaggcgct caagagcggc | 1680 |

| | |
|---|---|
| aagtacaagg tggtgcgcat caactacgcc aacccggaca tggtcggcca caccggcgac | 1740 |
| atggctgcca ccgtccgcgc ctgcgagacc gtggacgggt gcgtgaagga gctgctggag | 1800 |
| gtggtggaca gcctgaacgg ccgctggatc gtcacgtccg accacggcaa cgccgacgac | 1860 |
| atggtgcagc gcgacaagaa gggcaagccc ctgctgggcg aggacggcaa gccgctgccc | 1920 |
| ctgaccagcc acacgctggc gcccgtgccg ttcttcatcg gcggcaaggg cctgccggac | 1980 |
| ggcgtggtgc tgcgcgacga cctgccggac gccgggctgg ccaacgtggc cgccaccacc | 2040 |
| ttcaacctgc tgggcttcga ggcgcccggc atctacaagc ccagcatggt caaggcgtaa | 2100 |
| tctagataaa tggaggcgct cgttgatctg agccttgccc cctgacgaac ggcggtggat | 2160 |
| ggaagatact gctctcaagt gctgaagcgg tagcttagct ccccgtttcg tgctgatcag | 2220 |
| tcttttcaa cacgtaaaaa gcggaggagt tttgcaattt tgttggttgt aacgatcctc | 2280 |
| cgttgatttt ggcctctttc tccatggggcg ggctgggcgt atttgaagcg ttctctctt | 2340 |
| ctgccgtta | 2349 |

<210> SEQ ID NO 4
<211> LENGTH: 1815
<212> TYPE: DNA
<213> ORGANISM: Artificial Sequence
<220> FEATURE:
<223> OTHER INFORMATION: Synthetic oligonucleotide

<400> SEQUENCE: 4

| | |
|---|---|
| agaaaatctg gcaccacacc tatatggtag ggtgcgagtg accccgcgcg acttggagct | 60 |
| cgatggcccc gggttgtttg gggcgtccgc ctctcgcgct attctgagct ggagaccgag | 120 |
| gcgcatgaaa atgcattcgc ttccatagga cgctgcattg tggcttgaag gttcaaggga | 180 |
| agggttcaaa cgaccccgcc gtacgaactt ttgtcggggg gcgctcccgg ccccgggctc | 240 |
| ttgtgcgcgc attagggctt cgggtcgcaa gcaagacgat acctcgagca tatggccgcc | 300 |
| gtcattgcca agtcctccgt ctccgcggcc gtggctcgcc cggcccgctc cagcgtgcgc | 360 |
| cccatggccg cgctgaagcc cgccgtcaag gctgcccccg tggctgcccc ggctcaggcc | 420 |
| aaccaggtga ccaaggctgt tgagaacatc aacgctatta ttgcccccgc cctgaagggc | 480 |
| atggaccccg tcaagcaggc ggagattgac cagaagatga aggacctgga cggcactgac | 540 |
| aacaagggca agctgggtgc caacgccatc ctggccgtct ccatggccgt gtgcaaggcc | 600 |
| ggtgccgctg agaagggcgt gccccctgtac aagcacattg cggacctggc cggcaacagc | 660 |
| aagctgatcc tgcccgtgcc ctcgttcaac atcatcaacg cggcagcca cgccggcaac | 720 |
| gccctggcta tgcaggagtt catgatcctg cccgttggcg cctcgagctt ctctgaggcc | 780 |
| atgcgcatgg gctgcgaggt gtaccacgcc ctgaagggcc tgatcaaggc caagtacggc | 840 |
| caggacgcct gcaacgtggg tgatgagggt ggcttcgccc ccaacatcgg ctccaacgat | 900 |
| gagggcctga acttggtgaa cgaggccatc gagaaggccg gctacaccgg caaggtgaag | 960 |
| atcggcatgg acgtggcctc gtcggagttc tacaccgagg acggcatgta cgacctggac | 1020 |
| ttcaagaacc agcccaacga tggctcgcag aagaagacca aggagcagat gctggagctg | 1080 |
| tacaacgagt tctgcaagaa gtacccggtc atctccatcg aggacccctt cgagcaggac | 1140 |
| gactgggagc cctgcgccaa gctgaccacc gagaacatct gccaggtggt cggcgacgac | 1200 |
| atcctggtga ccaaccccgt gcgcgtgaag aaggccatcg accgcaaggc cgtcaacgct | 1260 |
| ctgctgctca aggtcaacca gatcggtacc attaccgagt ccattgaggc cgtgcgcatg | 1320 |
| gccaaggagg ccggctgggg tgtcatgacc agccaccgct cgggtgagac tgaggactct | 1380 |

```
ttcatcgccg acctggcggt gggcctggcc tccggccaga tcaagaccgg cgcccctgc      1440 cgctcggagc gcaatgccaa gtacaaccag ctgctgcgca tcgaggagga gctgggcgag      1500
aacgctgtgt acgctggcga gagctggcgc acatcggct ggggctgctg ccccggctgc       1560
tgctaatcta gataaatgga ggcgctcgtt gatctgagcc ttgcccctg acgaacggcg       1620 gtggatggaa gatactgctc tcaagtgctg aagcggtagc ttagctcccc gtttcgtgct      1680
gatcagtctt tttcaacacg taaaaagcgg aggagttttg caattttgtt ggttgtaacg      1740
atcctccgtt gatttggcc tctttctcca tgggcgggct gggcgtattt gaagcggttc       1800
tctcttctgc cgtta                                                       1815

<210> SEQ ID NO 5
<211> LENGTH: 2021
<212> TYPE: DNA
<213> ORGANISM: Artificial Sequence
<220> FEATURE:
<223> OTHER INFORMATION: Synthetic oligonucleotide

<400> SEQUENCE: 5
agaaaatctg gcaccacacc atggtagggt gcgagtgacc ccgcgcgact tggaagggtt        60
caaacgaccc cgccgtacga acttttgtcg gggggcgctc ccggctcgag catatggccg       120
ccgtcattgc caagtcctcc gtctccgcgg ccgtggctcg cccggcccgc tccagcgtgc      180
gccccatggc cgcgctgaag cccgccgtca aggctgcccc cgtggctgcc ccggctcagg      240
ccaaccagat gtctagatta gaaagattga cctcattaaa cgttgttgct ggttctgact      300
tgagaagaac ctccatcatt ggtaccatcg gtccaaagac caacaaccca gaaaccttgg      360
ttgctttgag aaaggctggt ttgaacattg tccgtatgaa cttctctcac ggttcttacg      420
aataccacaa gtctgtcatt gacaacgcca gaaagtccga agaattgtac ccaggtagac      480
cattggccat tgctttggac accaagggtc cagaaatcag aactggtacc accaccaacg      540
atgttgacta cccaatccca ccaaaccacg aaatgatctt caccaccgat gacaagtacg      600
ctaaggcttg tgacgacaag atcatgtacg ttgactacaa gaacatcacc aaggtcatct      660
ccgctggtag aatcatctac gttgatgatg tgttttgtc tttccaagtt ttggaagtcg       720
ttgacgacaa gactttgaag gtcaaggctt gaacgccgg taagatctgt tcccacaagg       780
gtgtcaactt accaggtacc gatgtcgatt gccagctttt gtctgaaaag gacaaggaag      840
atttgagatt cggtgtcaag aacggtgtcc acatggtctt cgcttctttc atcagaaccg      900
ccaacgatgt tttgaccatc agagaagtct gggtgaaca aggtaaggac gtcaagatca       960
ttgtcaagat tgaaaaccaa caaggtgtta caacttcga cgaaatcttg aaggtcactg       1020
acggtgttat ggttgccaga ggtgacttgg gtattgaaat cccagcccca gaagtcttgg      1080
ctgtccaaaa gaaattgatt gctaagtcta acttggctgg taagccagtt atctgtgcta      1140
cccaaatgtt ggaatccatg acttacaacc caagaccaac cagagctgaa gtttccgatg      1200
tcggtaacgc tatcttggat ggtgctgact gtgttatgtt gtctggtgaa accgccaagg      1260
gtaactaccc aatcaacgcc gttaccacta tggctgaaac cgctgtcatt gctgaacaag      1320
ctatcgctta cttgccaaac tacgatgaca tgagaaactg tactccaaag ccaacctcca      1380
ccaccgaaac cgtcgctgcc tccgctgtcg ctgctgtttt cgaacaaaag gccaaggcta      1440
tcattgtctt gtccacttcc ggtaccaccc caagattggt ttccaagtac agaccaaact      1500
gtccaatcat cttggttacc agatgccaa gagctgctag attctctcac ttgtacagag      1560
gtgtcttccc attcgttttc gaaaaggaac ctgtctctga ctggactgat gatgttgaag      1620
```

| cccgtatcaa cttcggtatt gaaaaggcta aggaattcgg tatcttgaag aagggtgaca | 1680 |
| cttacgtttc catccaaggt ttcaaggccg gtgctggtca ctccaacact ttgcaagtct | 1740 |
| ctaccgttgg ctgctgcccc ggctgctgct aatctagata aatggaggcg ctcgttgatc | 1800 |
| tgagccttgc cccctgacga acggcggtgg atggaagata ctgctctcaa gtgctgaagc | 1860 |
| ggtagcttag ctccccgttt cgtgctgatc agtcttttc aacacgtaaa agcggagga | 1920 |
| gttttgcaat tttgttggtt gtaacgatcc tccgttgatt ttggcctctt tctccatggg | 1980 |
| cgggctgggc gtatttgaag cggttctctc ttctgccgtt a | 2021 |

<210> SEQ ID NO 6
<211> LENGTH: 2231
<212> TYPE: DNA
<213> ORGANISM: Artificial Sequence
<220> FEATURE:
<223> OTHER INFORMATION: Synthetic oligonucleotide

<400> SEQUENCE: 6

| agaaaatctg gcaccacacc atggtagggt gcgagtgacc ccgcgcgact tggaagggtt | 60 |
| caaacgaccc cgccgtacga acttttgtcg gggggcgctc ccggctcgag catatggccg | 120 |
| ccgtcattgc caagtcctcc gtctccgcgg ccgtggctcg cccggcccgc tccagcgtgc | 180 |
| gccccatggc cgcgctgaag cccgccgtca aggctgcccc cgtggctgcc ccggctcagg | 240 |
| ccaaccagat ggtatcaacc tacccagaat cagaggttac tctaggaagg tacctctttg | 300 |
| agcgactcca ccaattgaaa gtggacacca ttttcggctt gccgggtgac ttcaacctt | 360 |
| ccttattgga caaagtgtat gaagttccgg atatgaggtg ggctggaaat gccaacgaat | 420 |
| tgaatgctgc ctatgctgcc gatggttact ccagaataaa gggattgtct tgcttggtca | 480 |
| caacttttgg tgttggtgaa ttgtctgctt taaacggagt tggtggtgcc tatgctgaac | 540 |
| acgtaggact tctacatgtc gttggagttc catccatatc gtcacaggct aaacagttgt | 600 |
| tgctccacca taccttgggt aatggtgact tcactgtttt tcacagaatg tccaatagca | 660 |
| tttctcaaac tacagcattt ctctcagata tctctattgc accaggtcaa atagatagat | 720 |
| gcatcagaga agcatatgtt catcagagac cagtttatgt tggtttaccg gcaaatatgg | 780 |
| ttgatctcaa ggttccttct agtctcttag aaactccaat tgatttgaaa ttgaaacaaa | 840 |
| atgatcctga agctcaggaa gaagttgttg aaacagtcct gaagttggtg tcccaagcta | 900 |
| caaaccccat tatcttggta gacgcttgtg ccctcagaca caattgcaaa gaggaagtca | 960 |
| aacaattggt tgatgccact aattttcaag tctttacaac tccaatgggt aaatctggta | 1020 |
| tctccgaatc tcatccaaga tttggcggtg tctatgtcgg acaatgtcg agtcctcaag | 1080 |
| tcaaaaaagc cgttgaaaat gccgatctta tactatctgt tggttcgttg ttatcggact | 1140 |
| tcaatacagg ttcatttca tactcctaca gacgaagaa tgttgttgaa ttccactctg | 1200 |
| actatatgaa aatcagacag gccacctcc caggagttca aatgaaagaa gccttgcaac | 1260 |
| agttgataaa aagggtctct tcttacatca atccaagcta cattcctact cgagttccta | 1320 |
| aaaggaaaca gccattgaaa gctccatcag aagctccttt gacccaagaa tatttgtggt | 1380 |
| ctaaagtatc cggctggttt agagagggtg atattatcgt aaccgaaact ggtacatctg | 1440 |
| ctttcggaat tattcaatcc cattttccca gcaaacactact cggtatatcc caagtcttgt | 1500 |
| ggggctcaat tggtttcaca gtaggtgcaa cagttggtgc tgccatggca gcccaggaaa | 1560 |
| tcgaccctag caggagagta attttgttcg tcggtgatgg ttcattgcag ttgacggttc | 1620 |
| aggaaatctc tacgttgtgt aaatgggatt gtaacaatac ttatctttac gtgttgaaca | 1680 |

```
atgatggtta cactatagaa aggttgatcc acggcaaaag tgccagctac aacgatatac    1740
agccttggaa ccatttatcc ttgcttcgct tattcaatgc taagaaatac caaaatgtca    1800
gagtatcgac tgctggagaa ttggactctt tgttctctga taagaaattt gcttctccag    1860
ataggataag aatgattgag gtgatgttat cgagattgga tgcaccagca atcttgttg     1920 ctcaagcaaa gttgtctgaa cgggtaaacc ttgaaaatgg ctgctgcccc ggctgctgct    1980
aatctagata aatggaggcg ctcgttgatc tgagccttgc cccctgacga acggcggtgg    2040
atggaagata ctgctctcaa gtgctgaagc ggtagcttag ctccccgttt cgtgctgatc    2100
agtctttttc aacacgtaaa aagcggagga gttttgcaat tttgttggtt gtaacgatcc    2160
tccgttgatt ttggcctctt tctccatggg cgggctgggc gtatttgaag cggttctctc    2220
ttctgccgtt a                                                         2231

<210> SEQ ID NO 7
<211> LENGTH: 1649
<212> TYPE: DNA
<213> ORGANISM: Artificial Sequence
<220> FEATURE:
<223> OTHER INFORMATION: Synthetic oligonucleotide

<400> SEQUENCE: 7
agaaaatctg gcaccacacc atggtagggt gcgagtgacc ccgcgcgact tggaagggtt      60
caaacgaccc cgccgtacga acttttgtcg ggggcgctc ccggatggta gggtgcgagt     120
gaccccgcgc gacttggaag ggttcaaacg accccgccgt acgaacttttt gtcgggggc    180 gctcccggct cgagcatatg gccgccgtca ttgccaagtc ctccgtctcc gcggccgtgg    240
ctcgcccggc ccgctccagc gtgcgcccca tggccgcgct gaagcccgcc gtcaaggctg    300 ccccgtggc tgccccggct caggccaacc agatgtctat cccaaaaact caaaaaggtg     360
ttatcttcta cgaatcccac ggtaagttgg aatacaaaga tattccagtc caacccccaa    420
aggccaacga attgttgatc aacgtcaagt actccggtgt ctgtcacact gacttgcacg    480
cttggcacgg tgactggcct ttgccagtca agctaccatt agttggtggt cacgaaggtg    540
ccggtgtcgt tgtcgccatg ggtgaaaacg tcaagggctg gaacatcggt gactacgccg    600
gtattaagtg gttgaacggt tcttgtatgg cctgtgaata ctgtgaattg ggtaacgaat    660
ccaactgtcc tcacgctgac ttgtctggtt acacccacga cggttctttc aacaatacg     720 ctaccgctga ctccgtccaa gccgctcaca ttccaaaggg tactgacttg gctgaatgtg    780
ctccagtctt gtgtgctggt atcactgtct acaaggcttt gaagtccgct aacttgtctg    840
ccggccaatg ggttgccatt tccggtgctg ctggtggtct aggttctttg gctgtccaat    900
acgccaaggc catgggttac agagtcgtcg gtattgacgg tggtgaaggt aaggaagaat    960
tattcagatc cattggtggt gaagttttca tcgatttcac tactgaaaag gacattgtcg   1020
gtgccgtcat caaggccact gacggtggtg ctcacgtat cattaacgtt ccgtttccg     1080 aagccgccat cgaagcttct accagatact gtagagctaa cggtaccact gttttggtcg   1140
gtatgccagc cggtgctaag tgttgttctg atgtcttcaa ccaagtcgtc aagtccatct   1200
ccattgtcgg ttcttacgtc ggtaacagag ctgacaccag agaagctttg gacttcttcg   1260 ccagagggttt ggtcaagtct ccaatcaagg ttgtcggttt gtctaccttg ccagaaattt   1320
acgaaaagat ggaaaagggt caaatcgtcg gtagatacgt tgttgacact tctaaaggct   1380 gctgcccgg ctgctgctaa tctagataaa tggaggcgct cgttgatctg agccttgccc    1440
cctgacgaac ggcggtggat ggaagatact gctctcaagt gctgaagcgg tagcttagct   1500
```

-continued

| | |
|---|---|
| ccccgtttcg tgctgatcag tcttttttcaa cacgtaaaaa gcggaggagt tttgcaattt | 1560 |
| tgttggttgt aacgatcctc cgttgatttt ggcctctttc tccatgggcg ggctgggcgt | 1620 |
| atttgaagcg gttctctctt ctgccgtta | 1649 |

<210> SEQ ID NO 8
<211> LENGTH: 2351
<212> TYPE: DNA
<213> ORGANISM: Artificial Sequence
<220> FEATURE:
<223> OTHER INFORMATION: Synthetic oligonucleotide

<400> SEQUENCE: 8

| | |
|---|---|
| agaaaatctg gcaccacacc gagctgtcat gcgttgttcc gttatgtgtc gtcaaacgcc | 60 |
| ttcgagcgct gcccggaaca atgcgtacta gtataggagc catgaggcaa gtgaacagaa | 120 |
| gcgggctgac tggtcaaggc gcacgatagg gctgacagag cgtgctgacgg ggtgtaccgc | 180 |
| cgagtgtccg ctgcattccc gccggattgg gaaatcgcga tggtcgcgca taggcaagct | 240 |
| cgcaaatgct gtcagcttat cttacatgaa cacacaaaca ctctcgcagg cactagcctc | 300 |
| aaatggccgc cgtcattgcc aagtcctccg tctccgcggc cgtggctcgc ccggcccgct | 360 |
| ccagcgtgcg ccccatggcc gcgctgaagc ccgccgtcaa ggctgccccc gtggctgccc | 420 |
| cggctcaggc caaccagatg gcgcacgact acaagctgaa ggcccacccg gcgattcctg | 480 |
| cgcccgaggg cccgctgctg gtctgcattc tggacggctt cggcgagaac gagtacaagg | 540 |
| atgagttcaa cgccgtgcac gtggctaaga cgcccactgt ggacgcgctg cgcgctgtgc | 600 |
| cccatcgctt ccgttccatc aaggcgcacg aaaggctgt gggcctgccc agcgatgccg | 660 |
| acatgggcaa cagcgaggtg gggcacaacg ccctgggctc gggccaggtg gtggaccaag | 720 |
| gcgcgcgcct ggtggacctg gcgctggaga ccggccgtat gttctcggac cccggctgga | 780 |
| agctcatcag cgaggccttc ccctcccaca ccgtccactt catcggcctg ctgtccgacg | 840 |
| gcggcgtgca ctcgcgcgcc gatcagctgc acggctgcct gcgcggcgcc gtggagcgcg | 900 |
| gcgccaagcg cgtgcgcgtg cacatcctga ctgacgccg cgacgtgccg gacggcagca | 960 |
| gcatccggtt cgtggaggag ctggaggcgg tgctggcgga gctgcgcggc aagggctgcg | 1020 |
| acatcgccat cgcctcgggc ggcggccgca tgcaggtcac catggaccgc tacgaggcgg | 1080 |
| actggagcat ggtgaagcgc ggctgggacg cgcacgtgct gggcaaggcg ccccactact | 1140 |
| tcaaggacgc caagaccgcg gtcaccaccc tgcgcggctc cgaggacgcg ccggtgtctg | 1200 |
| accagtacgt ggccccctt gtgattgtgg acaggcgga caagccggtg gcaccattg | 1260 |
| aggacggcga cgcggtggtg ctgttcaact tccgcgcgga ccgcatggtg gagatcagca | 1320 |
| aggccttcga gtacgaggac ggcttcaccg cctttgagcg cgagcgcttc cccaagggcc | 1380 |
| tgcgcttcgt gggcatgatg cagtacgacg gcgacctgaa gctgcccgcc aacttcctgg | 1440 |
| tgccgccgcc cctgattgag cacgtgtcgg gcagtacct gtgcaagaac gggctgagca | 1500 |
| ccttcgcctg ctccgagact cagaagttcg gcacgtgac gttcttctgg aacggcaacc | 1560 |
| gctccggcta cctggacgcc aagcaggagc agtacctgga gatcccgtcg acaagatcg | 1620 |
| agttcaacaa ggctccggac atgaaggcgc gcgagatcac cgccgccggc attgaggcgc | 1680 |
| tcaagagcgg caagtacaag gtggtgcgca tcaactacgc caacccggac atggtcggcc | 1740 |
| acaccggcga catggctgcc accgtccgcg cctgcgagac cgtggacggg tgcgtgaagg | 1800 |
| agctgctgga ggtggtggac agcctgaacg gccgctggat cgtcacgtcc gaccacggca | 1860 |
| acgccgacga catggtgcag cgcgacaaga agggcaagcc cctgctgggc gaggacggca | 1920 |

| | |
|---|---|
| agccgctgcc cctgaccagc cacacgctgg cgcccgtgcc gttcttcatc ggcggcaagg | 1980 |
| gcctgccgga cggcgtggtg ctgcgcgacg acctgccgga cgccgggctg ccaacgtgg | 2040 |
| ccgccaccac cttcaacctg ctgggcttcg aggcgcccgg catctacaag cccagcatgg | 2100 |
| tcaaggcgta atggaggcg ctcgttgatc tgagccttgc ccctgacga acggcggtgg | 2160 |
| atggaagata ctgctctcaa gtgctgaagc ggtagcttag ctccccgttt cgtgctgatc | 2220 |
| agtcttttc aacacgtaaa aagcggagga gttttgcaat tttgttggtt gtaacgatcc | 2280 |
| tccgttgatt ttggcctctt tctccatggg cgggctgggc gtatttgaag cggttctctc | 2340 |
| ttctgccgtt a | 2351 |

<210> SEQ ID NO 9
<211> LENGTH: 1796
<212> TYPE: DNA
<213> ORGANISM: Artificial Sequence
<220> FEATURE:
<223> OTHER INFORMATION: Synthetic oligonucleotide

<400> SEQUENCE: 9

| | |
|---|---|
| agaaaatctg gcaccacacc gagctgtcat gcgttgttcc gttatgtgtc gtcaaacgcc | 60 |
| ttcgagcgct gcccggaaca atgcgtacta gtataggagc catgaggcaa gtgaacagaa | 120 |
| gcgggctgac tggtcaaggc gcacgatagg gctgacgagc gtgctgacgg ggtgtaccgc | 180 |
| cgagtgtccg ctgcattccc gccggattgg gaaatcgcga tggtcgcgca taggcaagct | 240 |
| cgcaaatgct gtcagcttat cttacatgaa cacacaaaca ctctcgcagg cactagcctc | 300 |
| aaatggccgc cgtcattgcc aagtcctccg tctccgcggc cgtggctcgc ccggcccgct | 360 |
| ccagcgtgcg ccccatggcc gcgctgaagc ccgccgtcaa ggctgccccc gtggctgccc | 420 |
| cggctcaggc caaccaggtg accaaggctg ttgagaacat caacgctatt attgcccccg | 480 |
| ccctgaaggg catggacccc gtcaagcagg cggagattga ccagaagatg aaggacctgg | 540 |
| acggcactga caacaagggc aagctgggtg ccaacgccat cctggccgtc tccatggccg | 600 |
| tgtgcaaggc cggtgccgct gagaagggcg tgccctgta caagcacatt gcggacctgg | 660 |
| ccggcaacag caagctgatc ctgcccgtgc cctcgttcaa catcatcaac ggcggcagcc | 720 |
| acgccggcaa cgccctggct atgcaggagt tcatgatcct gcccgttggc gcctcgagct | 780 |
| tctctgaggc catgcgcatg ggctgcgagg tgtaccacgc cctgaagggc ctgatcaagg | 840 |
| ccaagtacgg ccaggacgcc tgcaacgtgg gtgatgaggg tggcttcgcc cccaacatcg | 900 |
| gctccaacga tgagggcctg aacttggtga acgaggccat cgagaaggcc ggctacaccg | 960 |
| gcaaggtgaa gatcggcatg gacgtggcct cgtcggagtt ctacaccgag gacggcatgt | 1020 |
| acgacctgga cttcaagaac cagcccaacg atggctcgca gaagaagacc aaggagcaga | 1080 |
| tgctggagct gtacaacgag ttctgcaaga agtacccggt catctccatc gaggacccct | 1140 |
| tcgagcagga cgactgggag ccctgcgcca agctgaccac cgagaacatc tgccaggtgg | 1200 |
| tcggcgacga catcctggtg accaaccccg tgcgcgtgaa gaaggccatc gacgccaagg | 1260 |
| ccgtcaacgc tctgctgctc aaggtcaacc agatcggtac cattaccgag tccattgagg | 1320 |
| ccgtgcgcat ggccaaggag gccggctggg gtgtcatgac cagccaccgc tcgggtgaga | 1380 |
| ctgaggactc tttcatcgcc gacctggcgg tgggcctggc ctccggccag atcaagaccg | 1440 |
| gcgccccctg ccgctcggag cgcaatgcca agtacaacca gctgctgcgc atcgaggagg | 1500 |
| agctgggcga gaacgctgtg tacgctgcg agagctggcg ccacatcggc tggtaaatgg | 1560 |
| aggcgctcgt tgatctgagc cttgccccct gacgaacggc ggtggatgga agatactgct | 1620 |

```
ctcaagtgct gaagcggtag cttagctccc cgtttcgtgc tgatcagtct ttttcaacac    1680
gtaaaaagcg gaggagtttt gcaattttgt tggttgtaac gatcctccgt tgattttggc    1740
ctctttctcc atgggcgggc tgggcgtatt tgaagcggtt ctctcttctg ccgtta        1796
```

<210> SEQ ID NO 10
<211> LENGTH: 1832
<212> TYPE: DNA
<213> ORGANISM: Artificial Sequence
<220> FEATURE:
<223> OTHER INFORMATION: Synthetic oligonucleotide

<400> SEQUENCE: 10

```
agaaaatctg gcaccacacc gagctgtcat gcgttgttcc gttatgtgtc gtcaaacgcc      60
ttcgagcgct gcccggaaca atgcgtacta gtataggagc catgaggcaa gtgaacagaa     120
gcgggctgac tggtcaaggc gcacgatagg gctgacgagc gtgctgacgg ggtgtaccgc     180
cgagtgtccg ctgcattccc gccggattgg gaaatcgcga tggtcgcgca taggcaagct     240
cgcaaatgct gtcagcttat cttacatgaa cacacaaaca ctctcgcagg cactagcctc     300
aaatggccgc cgtcattgcc aagtcctccg tctccgcggc cgtggctcgc ccggcccgct     360
ccagcgtgcg ccccatggcc gcgctgaagc ccgccgtcaa ggctgccccc gtggctgccc     420
cggctcaggc caaccagatg tgcgagatgc tggacgcggg cgtggtgggc tgccgcgtgg     480
acctgacgtg gggcccgctg gagttccacc gcaagtcgct tgccaatctg cagcaggca     540 tgcgcaagag ccgccgcctg tgttgcacca tggtggacac gctgggccgc gagctcatga     600
tccgccgcca gagaggggca ggctggaccc agcgccagag gggtggggtg atcatcacca     660
cgcgcacgga cgtggacgcc agcagcaacg tgctgcccat cacttacagc aagttcacgg     720
agatggcggt caagggcgac accatctaca tcggccgcta cctggtgtgc ggcgcagaca     780
gcgcctcgct gtacctggag gtcatggacg tgcaggcga cgacgtgtac tgcatcgcca     840
agaacgacgc ggtgctggac ggcctgctga cggtgttcca cgcggagcgc tccgtggagg     900
ggctggccaa cgtgcagaac gacctgccgc tgctgtccga ctacgacaag gagtgcctgc     960
acatcctggc gcaggacttc gagcgcgcgc cctacatctc caagctggag tccatcgcct    1020
cctccgccgt gcgcgccgcc gaccgcgtgg gcgccagcct gattgtggtg tacacgcaca    1080
ccggcaagac ggcgcagctg gtggccaagt accggccgcc catgcccatc ctgacgctgg    1140
tggtgccgca cctggtgtct gaccagctca agtggaagct ggagggcagg tccagcgcgc    1200
gccagtgcct catcagtcgc gcgctgctgc cggtgctggc cgcgccctcg cccagcggcg    1260
accagctgct gcaggaggcg gtggccatgg cgggccgcgt caagctggtc aagccgcacg    1320
accacgtggt gtgcgtgcag cgcatccacg acgacttctg cgtcaagatc atctccgtgg    1380
acgacatggg cgcgggcatc aagcgcgacg acacggtcat gtcgcacagc gtgtttggca    1440
gcagccccat ggccgtgcag ggctcgtccg gctacgactc gccgcgcgtg cacaacaacc    1500
ccatcggcaa caagttcggc cccatgccgc ccgccatcat caccaccggc aatagcttca    1560
ccctgggcgg catgggcgtg ggcgtgctgt aaatggaggc gctcgttgat ctgagccttg    1620 cccctgacg aacggcggtg gatggaagat actgctctca agtgctgaag cggtagctta    1680
gctccccgtt tcgtgctgat cagtcttttt caacacgtaa aaagcggagg agttttgcaa    1740
ttttgttggt tgtaacgatc ctccgttgat tttggcctct ttctccatgg gcgggctggg    1800
cgtatttgaa gcggttctct cttctgccgt ta                                  1832
```

<210> SEQ ID NO 11
<211> LENGTH: 2390
<212> TYPE: DNA
<213> ORGANISM: Artificial Sequence
<220> FEATURE:
<223> OTHER INFORMATION: Synthetic oligonucleotide

<400> SEQUENCE: 11

| | | | | | |
|---|---|---|---|---|---|
| agaaaatctg | gcaccacacc | gagctgtcat | gcgttgttcc | gttatgtgtc | gtcaaacgcc | 60 |
| ttcgagcgct | gcccggaaca | atgcgtacta | gtataggagc | catgaggcaa | gtgaacagaa | 120 |
| gcgggctgac | tggtcaaggc | gcacgatagg | gctgacgagc | gtgctgacgg | ggtgtaccgc | 180 |
| cgagtgtccg | ctgcattccc | gccggattgg | gaaatcgcga | tggtcgcgca | taggcaagct | 240 |
| cgcaaatgct | gtcagcttat | cttacatgaa | cacacaaaca | ctctcgcagg | cactagcctc | 300 |
| aaatggccgc | cgtcattgcc | aagtcctccg | tctccgcggc | cgtggctcgc | ccggcccgct | 360 |
| ccagcgtgcg | ccccatggcc | gcgctgaagc | ccgccgtcaa | ggctgccccc | gtggctgccc | 420 |
| cggctcaggc | caaccagatg | gccaccaccg | tgtcgcccgc | agacgccaac | ctcggcctgc | 480 |
| acattgccaa | ccggcttgtt | gagatcggct | gcaccagctg | cttcgcggtg | cccggcgact | 540 |
| tcaacctgct | gctgctggac | cagctgctca | agcagcccga | gctgtccctg | gtgtggtgct | 600 |
| gcaacgagct | gaatgcgggc | tacgcggcgg | acggctacgc | ccgcaagcgc | ggcgtgggct | 660 |
| gcctgtgcgt | gaccttctgt | gtgggaggct | ctccgccct  | gaacgctgtg | ggcggtgcct | 720 |
| acagtgagga | cctgccgctc | atcgtcatca | gcggggggcc | caactcgcag | gaccacgcct | 780 |
| ccaaccgcat | cctgcaccac | accacggggcg | ccaacgagta | cggccagcag | ctgcgcgcct | 840 |
| tcagggaggt | gacctgctgc | aggtggtca  | tccagcacat | cgaggacgcg | cacatgctgc | 900 |
| tggatacggc | catcagtgag | gcgatgctga | agcgcaagcc | cgtgtacatc | gaggtggcat | 960 |
| gtgagtgtgt | cgtgacttgg | tacttgttag | ggggcgggt  | gatggggggg | ccgtcgctct | 1020 |
| gggccgcggt | ggaggcggcg | gtggagtggc | tgggcggtgg | cgtgaagccg | ctgctgctgg | 1080 |
| cgggcgtgcg | cacgcgcccg | cccgccgcgc | gcaaggcgat | gctggccctg | gcggaggcca | 1140 |
| gccgctaccc | cgtggccgtg | atgccggacg | ccaagggcat | gttccccgag | gaccacgagc | 1200 |
| agtacatcgg | catgtactgg | ggccgggtgt | ccacgccgtg | tgtgtgcgag | gtggtggaga | 1260 |
| gcagcgacat | cgtgctgtgc | gtgggaggag | tgtggacgga | ctactccact | gccggctact | 1320 |
| cgctgctgct | caagcccgag | aagatgctgc | gcgtggacaa | caaccgcgtc | acattgggca | 1380 |
| acggaccgac | gtttggctgc | atcgtgatga | ccgacttcct | ggaggccctg | ccaagcgggg | 1440 |
| tggcgcccaa | cgacaccggc | cacgtcatct | acaagcgcat | ggctctgccg | ccctcggagc | 1500 |
| cgccgccgca | ggccgagggc | gaactgctgc | gcaccaacgt | gctgttcaaa | cacatccagc | 1560 |
| acatgctgac | tccctccacc | agcctcatca | gcgaggtggg | cgactcctgg | ttcaacacac | 1620 |
| tcaagctcaa | gctgcccgcc | ggctgcgagt | acgagctgca | gatgcgctac | ggctccattg | 1680 |
| gctggagtgt | gggcgcggtg | ctgggctacg | gcgtggcgga | gcgcagacg  | gcgcccgacc | 1740 |
| gccgcgtggt | ggcgtgcatc | ggcgacggct | ccttccagat | gaccgcacag | gaggtgagca | 1800 |
| ccatgctgcg | ctacggcctg | gaccccatca | tcttcctcat | caacaacggc | ggctacacca | 1860 |
| tcgaggtgga | gatccacgac | ggcccctaca | acgtgatcaa | gaactgggac | taccccggta | 1920 |
| tggtgcgcgc | gctgcacaac | ggccaggggca | agctgtggac | cgccgaggcc | cgcaccgagc | 1980 |
| ccgagctgca | ggccgccgtg | gccgaggctg | tgcagcggcg | cggcgagctg | tgcttcatca | 2040 |
| tggtggtgac | tcaccgtgac | gactgcagca | aggagctgct | ggagtggggc | agccgcgtgg | 2100 |
| cggcggccaa | cagccgcaag | ccgcccacca | ccggctacgg | cggccactaa | atggaggcgc | 2160 |

| | |
|---|---:|
| tcgttgatct gagccttgcc ccctgacgaa cggcggtgga tggaagatac tgctctcaag | 2220 |
| tgctgaagcg gtagcttagc tccccgtttc gtgctgatca gtcttttca acacgtaaaa | 2280 |
| agcggaggag ttttgcaatt ttgttggttg taacgatcct ccgttgattt tggcctcttt | 2340 |
| ctccatgggc gggctgggcg tatttgaagc ggttctctct tctgccgtta | 2390 |

<210> SEQ ID NO 12
<211> LENGTH: 3341
<212> TYPE: DNA
<213> ORGANISM: Artificial Sequence
<220> FEATURE:
<223> OTHER INFORMATION: Synthetic oligonucleotide

<400> SEQUENCE: 12

| | |
|---|---:|
| agaaaatctg gcaccacacc gagctgtcat gcgttgttcc gttatgtgtc gtcaaacgcc | 60 |
| ttcgagcgct gcccggaaca atgcgtacta gtataggagc catgaggcaa gtgaacagaa | 120 |
| gcgggctgac tggtcaaggc gcacgatagg gctgacgagc gtgctgacgg ggtgtaccgc | 180 |
| cgagtgtccg ctgcattccc gccggattgg gaaatcgcga tggtcgcgca taggcaagct | 240 |
| cgcaaatgct gtcagcttat cttacatgaa cacacaaaca ctctcgcagg cactagcctc | 300 |
| aaatggccgc cgtcattgcc aagtcctccg tctccgcggc cgtggctcgc ccggcccgct | 360 |
| ccagcgtgcg ccccatggcc gcgctgaagc ccgccgtcaa ggctgccccc gtggctgccc | 420 |
| cggctcaggc caaccagcat gctgaggtga agaaggagcg cgcccagcc accgatgagg | 480 |
| cgctgacgga gctgaaggcg ctgctgaagc gcgcccagac cgcccaggcg cagtactcca | 540 |
| cctacaccca ggagcaggtg gacgagatct ccgcgccgc cgccgaggcc gccaacgccg | 600 |
| cccgtatccc cctggccaag atggccgtgg aggagacccg catgggcgtg gctgaggaca | 660 |
| aggtggtgaa gaaccacttc gcctccgagt tcatctacaa caagtacaag cacactaaga | 720 |
| cctgcggcgt catcgagcac gaccccgccg cggcatcca aaggtggct gagcccgtgg | 780 |
| gcgtcattgc cggtatcgtg cccaccacca accccacctc caccgccatc ttcaagtcgc | 840 |
| tgctgtcgct caagacccgc aacgcgctgg tgctgtgccc gcaccccgc gccgccaaga | 900 |
| gcgccatcgc cgccgcgcgc atcgtgcgtg acgccgccgt ggccgccggc gcgccgccca | 960 |
| acatcatcag ctgggtggag acgccctcgc tgccggtgtc ccaggcgctg atgcaggcga | 1020 |
| ctgagatcaa cctcatcctg gccaccggtg gcccggccat ggtgcgcgcc gcctactcgt | 1080 |
| ccggcaaccc gtcgctgggt gtgggcgccg caacacccc ggccctgatt gacgagactg | 1140 |
| ccgacgtggc catggccgtg tcctccatcc tgctgtccaa gaccttgac aacggcgtca | 1200 |
| tctgcgcctc ggagcagtcg gtggtggtgg tggccaaggc ctacgacgcc gtgcgcaccg | 1260 |
| agttcgtgcg ccgcggggcc tacttcctga ccgaggacga caaggtcaag gtccgcgccg | 1320 |
| gtgtggtttgt ggacggcaag ctgaacccca acattgtggg ccagtccatc cccaagctgg | 1380 |
| cggccctgtt cggcatcaag gtgccccagg cacaacggt gctcatcggc gaggtggaga | 1440 |
| agatcggccc cgaggaggcg ctgtcgcagg agaagctgtg ccccatcctg gccatgtacc | 1500 |
| gggcgcccga ctacgaccac ggcgtcaaga tggcctgcga gctcatcatg tacgcggcg | 1560 |
| ccggccacac ctcggtgctg tacaccaacc cgctcaacaa cgcccacatc cagcagtacc | 1620 |
| agagcgcggt caagaccgtg cgcatcctca tcaaccccc cgcctcgcag ggcgccattg | 1680 |
| gtgacctgta caacttccac ctggaccct ccctcaccct gggctgcggc acctggggct | 1740 |
| ccacctcggt gtccaccaac gtgggcccgc agcacctgct gaacatcaag accgtcaccg | 1800 |
| cgcgccgcga gaacatgctg tggttccgcg tgccgcccaa gatctacttc aagggcggct | 1860 |

-continued

| | |
|---|---|
| gcctggaggt ggcgctgacc gatctgcgtg gcaaatcgcg cgctttcatt gtcacggaca | 1920 |
| agccgctttt tgacatggga tacgccgaca aggtcaccca catcctggac agcattaacg | 1980 |
| tgcaccacca ggtgttctac cacgtgaccc ccgacccgac cctggcctgc attgaggcgg | 2040 |
| gtctgaagga gatcctggag ttcaagcccg atgtcatcat cgcgctgggt ggtggctcgc | 2100 |
| ccatggacgc cgccaagatc atgtggctga tgtacgagtg cccgacacc cgcttcgacg | 2160 |
| gcctggccat gcgcttcatg gacatccgca agcgcgtgta cgaggtgccg gagctgggca | 2220 |
| agaaggccac catggtgtgc atccccacca ccagtggcac cggctcggag gtgacgccct | 2280 |
| tctcggtggt caccgacgag cgcctgggcg ccaagtaccc cctggccgat tacgccctga | 2340 |
| cccccagcat ggccattgtg acccccagc tggtgctcaa catgcccaag aagctgaccg | 2400 |
| cctgggcgg cattgacgcg ctcacgcacg cgctggagag ctacgtgtcc atctgcgcca | 2460 |
| ccgactacac caagggtctg tcgcgcgagg ccatcagcct gctgttcaag tacctgcccc | 2520 |
| gcgcctacgc caacggctcc aacgactacc tggcgcgtga aaggtgcac tacgccgcca | 2580 |
| cgattgccgg catggccttc gccaacgcct tcctgggcat ctgccactcc atggcgcaca | 2640 |
| agctgggcgc cgcctaccac gtgcctcacg gcctggccaa cgccgcgctg atcagccacg | 2700 |
| tcatccgcta caacgccacc gacatgcccg ccaagcaggc cgccttcccg cagtacgagt | 2760 |
| accccaccgc caagcaggac tacgccgacc tggccaacat gctgggcctg gcggcaaca | 2820 |
| cggtggacga gaaggtgatc aagctgattg aggcggtgga ggagctcaag gccaaggtgg | 2880 |
| acatcccgcc caccatcaag gagatcttca acgaccccaa ggtggacgcc gacttcctgg | 2940 |
| cgaacgtgga cgccctggcc gaggacgcct tcgacgacca gtgcacgggc gccaacccgc | 3000 |
| gctaccgct catggccgac ctgaagcagc tctacctgga cgcccacgcc gcgcccatcc | 3060 |
| tgcccgtcaa gaccctggag ttcttctcca agatcaacta aatggaggcg ctcgttgatc | 3120 |
| tgagccttgc cccctgacga acggcggtgg atggaagata ctgctctcaa gtgctgaagc | 3180 |
| ggtagcttag ctccccgttt cgtgctgatc agtcttttc aacacgtaaa aagcggagga | 3240 |
| gttttgcaat tttgttggtt gtaacgatcc tccgttgatt ttggcctctt tctccatggg | 3300 |
| cgggctgggc gtatttgaag cggttctctc ttctgccgtt a | 3341 |

<210> SEQ ID NO 13
<211> LENGTH: 1556
<212> TYPE: DNA
<213> ORGANISM: Artificial Sequence
<220> FEATURE:
<223> OTHER INFORMATION: Synthetic oligonucleotide

<400> SEQUENCE: 13

| | |
|---|---|
| agaaaatctg gcaccacacc atggtagggt gcgagtgacc ccgcgcgact tggaagggtt | 60 |
| caaacgaccc cgccgtacga acttttgtcg ggggcgctc ccggatggta gggtgcgagt | 120 |
| gaccccgcgc gacttggaag ggttcaaacg accccgccgt acgaactttt gtcgggggc | 180 |
| gctcccggat ggccctgatg atgaagtcgt cggccagcct gaaggctgtg tcgctggccg | 240 |
| ctctcgccgc gccgtcgttg tgcgcgccgg gcaagtacga tgaggagctg attaagaccg | 300 |
| ctggcaccgt tgcctccaag ggccgcggta tcctggccat ggacgagtca aacgccacct | 360 |
| gcggcaaacg cctggactcc atcggcgtgg agaacaccgg ggagaaccgc cgcgcctacc | 420 |
| gcgagctgct ggtgaccgcc cccggcctgg ccagtacat ctccggcgct atcctgttcg | 480 |
| aggagaccct gtatcagtcc accgcctccg gcaagaagtt cgtcgatgtg atgaaggagc | 540 |
| agaacatcgt gcccggcatc aaggtcgaca agggcctggt gccctgtcca acaccaacga | 600 |

| | |
|---|---|
| tgagctggtg catgggcctg gacggctgga caagcgctgc tgagtactac aaggccggcg | 660 |
| ctcgcttcgc caagtggcgc tcggtcgtct cgatccccca cggcccctcg atcatgctgc | 720 |
| cgcgactggc ctacggcctg gcccgctacg ccgccatcgc ccagaacgcc ggtctggtgc | 780 |
| ccattgtgga gcccgaggtc ctgctggacg gtgagcacga catcgaccgc tgcctggagg | 840 |
| tgcaggaggc catctgggcc gagaccttca agtacatggc cgacaacaag gtcatgttgc | 900 |
| agggtatcct gctgaagccc gccatggtca cccccggcgc tgactgcaag aacaaggccg | 960 |
| gccccgccaa ggttgccgag tacaccctga agatgctggc cgcgcgtgcc ccccggtcc | 1020 |
| ccggcatcat gttcctgtcg gcggccagt ccgagctgga gtcgaccctg aacctgaacg | 1080 |
| ccatgaacca gagccccaac ccgtggcacg tgtcgttctc gtacgcccgc gctctgacga | 1140 |
| acaccgttct gaagacctgg caggcaagcc cgagaacggt ccaggcgccc aggctcgctg | 1200 |
| ctcaagcgcg caaggccaac tcggacgctc agcagggcaa gtacgacgcc accaccgagg | 1260 |
| gcaaggaggc tgcccagggc atgtacgaga agggaaaagg ctacgtctac taataaatgg | 1320 |
| aggcgctcgt tgatctgagc cttgccccct gacgaacggc ggtggatgga agatactgct | 1380 |
| ctcaagtgct gaagcggtag cttagctccc cgtttcgtgc tgatcagtct tttcaacac | 1440 |
| gtaaaaagcg gaggagtttt gcaattttgt tggttgtaac gatcctccgt tgatttggc | 1500 |
| ctctttctcc atgggcggc tgggcgtatt tgaagcggtt ctctcttctg ccgtta | 1556 |

<210> SEQ ID NO 14
<211> LENGTH: 1379
<212> TYPE: DNA
<213> ORGANISM: Artificial Sequence
<220> FEATURE:
<223> OTHER INFORMATION: Synthetic oligonucleotide

<400> SEQUENCE: 14

| | |
|---|---|
| agaaaatctg gcaccacacc atggtagggt gcgagtgacc ccgcgcgact tggaagggtt | 60 |
| caaacgaccc cgccgtacga acttttgtcg gggggcgctc ccggatggta gggtgcgagt | 120 |
| gaccccgcgc gacttggaag ggttcaaacg accccgccgt acgaactttt gtcgggggc | 180 |
| gctcccggat ggcagctacc tctctcactg ccctccttc tttctccggt ctccgccgca | 240 |
| tttctcccaa gctcgacgct gccgccgtct cctcccacca atccttcttc caccgcgtca | 300 |
| attcctctac ccgtctcgtt tcttcctctt cttcttctca tcgctccccc agaggtgttg | 360 |
| ttgccatggc tggatccgga aagttttcg ttggaggaaa ctggaagtgt aacgggacta | 420 |
| aggactccat cgccaagctt atctccgatc tcaacagtgc aaccttggaa gcagatgtag | 480 |
| atgttgttgt gtcacctcca tttgtctaca tcgaccaggt caaatcctcg ttgacagacc | 540 |
| gtattgacat atcaggtcag aactcttggg ttgggaaagg tggagccttc actggtgaaa | 600 |
| tcagcgtgga acagctcaaa gaccttggct gcagtgggt cattcttggg cattccgaac | 660 |
| ggagacatgt catcggagaa aaagatgagt ttatcggaa gaaagctgca tatgcattga | 720 |
| gtgagggtct tggagtgata gcttgtattg ggaaaagct agaagagagg gaagcaggca | 780 |
| agacgtttga tgtttgcttc gcgcaactga aggcgtttgc tgatgctgtg cctagctggg | 840 |
| acaatatagt tgttgcatac gagcctgtat gggcaattgg aactggtaaa gttgcatctc | 900 |
| ctcagcaagc acaagaagtc catgtagctg tccgcgttg gctaaagaag aatgtctctg | 960 |
| aggaagttgc ttccaaaacg agaatcatat atggaggttc tgtcaatgga ggcaacagtg | 1020 |
| cagagcttgc caaagaagaa gacattgatg gatttcttgt tggtggtgcc tccttgaagg | 1080 |
| gtcctgagtt tgcaaccatt gtgaactcag tcacgtcgaa gaaagttgct gcttgataaa | 1140 |

```
tggaggcgct cgttgatctg agccttgccc cctgacgaac ggcggtggat ggaagatact   1200
gctctcaagt gctgaagcgg tagcttagct ccccgtttcg tgctgatcag tcttttttcaa  1260 cacgtaaaaa gcgaggagt tttgcaattt tgttggttgt aacgatcctc cgttgatttt   1320
ggcctctttc tccatgggcg ggctgggcgt atttgaagcg gttctctctt ctgccgtta   1379
```

<210> SEQ ID NO 15
<211> LENGTH: 2156
<212> TYPE: DNA
<213> ORGANISM: Artificial Sequence
<220> FEATURE:
<223> OTHER INFORMATION: Synthetic oligonucleotide

<400> SEQUENCE: 15

```
agaaaatctg gcaccacacc atggtagggt gcgagtgacc ccgcgcgact tggaagggtt     60
caaacgaccc cgccgtacga acttttgtcg gggggcgctc ccggatggta gggtgcgagt    120
gaccccgcgc gacttggaag ggttcaaacg accccgccgt acgaactttt gtcgggggc    180 gctcccggat ggccgccgtc attgccaagt cctccgtctc cgcggccgtg gctcgcccgg   240
cccgctccag cgtgcgcccc atggccgcgc tgaagcccgc cgtcaaggct gccccgtgg    300 ctgccccggc tcaggccaac cagatggaag cttcgatttc gtttctgggg tcaacaaaac   360
ccaatatttc cttgtttaac ccttcttcaa acgtccttcc tcgtagagat ttccctcttc   420
ctgctttgaa attgaagaaa gtttcagtgc tgcctcgaat cttgcaccag aaacgactca   480
tcagagctca gtgctctgat ggattcaaac cagaggaaga cgatgggttt gtcctagaag   540
acgttcctca cttgaccaaa tttctccctg atttaccgtc atatccaaat ccattgaaag   600
aaagccaagc atatgccatt gttaagcgaa cttttgtcag ttccgaagat gtggttgcgc   660
aaaatattgt agtccagaag ggaagtaagc gaggagtaca ctttaggcga gcagggcctc   720
gagaaagagt gtacttcaga tcagatgaag taaaagcttg catagtgact tgtgggggct   780
tgtgccctgg aatcaatact gttatacggg aaattgtatg tggattgaac aatatgtatg   840
gtgttaataa cattctcggc attcaggag atatagagg cttttactcc aaaaacacta    900
tgaacctgac acctaaagta gttaacgata ttcataaacg cggtggcact tttcttcaaa   960
cctcaagagg aggacatgat acagcgaaga ttgttgataa tattcaagat agaggaataa  1020
atcaggtata tattattgga ggtggtggga cgcaaaaggg tgcagagaag atatacgagg  1080
aagttgagag gcgtggtctt caagtggcgg tttctggcat tcctaagaca attgataatg  1140
atattgctgt gattgacaaa tcatttggct ttgatacggc ggttgaggaa gcacaacgag  1200
ctattaatgc tgcacatgta gaggtcgaga gcgtggaaaa tggagttggt atcgttaaac  1260
tcatgggcag atacagtggt tttattgcca tgattgcaac tttagcgaat cgtgatgtgg  1320
attgttgctt gattccagag tctccatttt tccttgaagg aaagggtggg ctctttgagt  1380
ttattgaaga acgactcaaa gagaataggc acatggttat tgtgatagct gaaggagctg  1440
gacaggatta tgttgctcaa agcatgcgtg catctgaaac taaagacgcc tcaggaaata  1500
gactcttgct tgatgttggt ctatggttga ctcaacagat aaaggatcac tttacaaatg  1560
ttcggaaaat gatgataaat atgaagtaca tagacccaac gtatatgata agagcaaatac  1620 cgagtaacgc atcagacaat gtctattgca ctcttcttgc ccaaagtgca gttcatggag  1680
caatggctgg gtactcaggt ttcactgtag gaccagttaa cagtagacat gcttacatcc  1740
caatttctgt gacggaagtg acaaatacgg tgaagttaac tgataggatg tgggctagac  1800
tccttgcatc gacaaatcaa ccgagttttct tgactggtga aggagcattg cagaatgtga  1860
```

```
tcgacatgga aactcaagaa aagatcgata acatgaagat ctcttctatc taataaatgg    1920
aggcgctcgt tgatctgagc cttgccccct gacgaacggc ggtggatgga agatactgct    1980
ctcaagtgct gaagcggtag cttagctccc cgtttcgtgc tgatcagtct ttttcaacac    2040
gtaaaaagcg gaggagtttt gcaattttgt tggttgtaac gatcctccgt tgattttggc    2100
ctctttctcc atgggcgggc tgggcgtatt tgaagcggtt ctctcttctg ccgtta        2156

<210> SEQ ID NO 16
<211> LENGTH: 860
<212> TYPE: DNA
<213> ORGANISM: Artificial Sequence
<220> FEATURE:
<223> OTHER INFORMATION: Synthetic oligonucleotide

<400> SEQUENCE: 16
agaaaatctg gcaccacacc tatatggtag ggtgcgagtg accccgcgcg acttggagct      60
cgatggcccc gggttgtttg gggcgtccgc ctctcgcgct attctgagct ggagaccgag     120
gcgcatgaaa atgcattcgc ttccatagga cgctgcattg tggcttgaag gttcaaggga     180
agggttcaaa cgaccccgcc gtacgaactt ttgtcggggg cgctcccgg ccccgggctc      240 ttgtgcgcgc attagggctt cgggtcgcaa gcaagacgat acatgccagc cggctcacca     300
ccgccaccag cggcttgcgg gggtccacct ccaggcccag accttctgc agaaactcct      360 tgcacagcgc cttcccggcg gggcggtcgg cgtcgaagtt ggctggcagc agcgcgtcag     420
tggccgggtt ccactcctca cagtcaatgc cgttcaggat gccgtggaac ttggagcgca     480
gctcggggcg cgcgaaggtg gatctcgccg tcccagcggt agcccttggg cacctcgatg     540
tcgcattcgt gcttgaggcc ctcaatctgg tccttgggca ggcactcgta gaacggcagc     600
atgaccgtca cgaagtgtaa atggaggcgc tcgttgatct gagccttgcc ccctgacgaa     660
cggcggtgga tggaagatac tgctctcaag tgctgaagcg gtagcttagc tccccgtttc     720
gtgctgatca gtcttttttca acacgtaaaa agcggaggag ttttgcaatt ttgttggttg    780
taacgatcct ccgttgattt tggcctcttt ctccatgggc gggctgggcg tatttgaagc     840
ggttctctct tctgccgtta                                                 860

<210> SEQ ID NO 17
<211> LENGTH: 1328
<212> TYPE: DNA
<213> ORGANISM: Artificial Sequence
<220> FEATURE:
<223> OTHER INFORMATION: Synthetic oligonucleotide

<400> SEQUENCE: 17
agaaaatctg gcaccacacc gagctgtcat gcgttgttcc gttatgtgtc gtcaaacgcc      60
ttcgagcgct gcccggaaca atgcgtacta gtataggagc catgaggcaa gtgaacagaa     120
gcgggctgac tggtcaaggc gcacgatagg gctgacgagc gtgctgacgg ggtgtaccgc     180
cgagtgtccg ctgcattccc gccggattgg gaaatcgcga tggtcgcgca taggcaagct     240
cgcaaatgct gtcagcttat cttacatgaa cacacaaaca ctctcgcagg cactagcctc     300
aaatgaagag cttcatgcgg agggatgcgc tcggcgcggg gctccgcggt gcagccagca     360
caaagcccgt ctcaagggtc gccagcgtga ggcctgcgcc taccgcctac cgcactgcct     420
gccaagttgc gaaggtggat gaaatggtgt cggtggatga ggagcttact cgtctccgca     480
aggagaacga gctcctgcgc gcccaactgg cgctgtacca gcagaaccag cagccgtccg     540
tgggtgccgc tgccgttgcc ccgcctgctg ccgccacgaa ggtgctggag aagccggcgc     600
```

| | |
|---|---|
| cgtaagtaac ctaacggtga gcagcatgca atattttagc gtcgatactc ggaaactata | 660 |
| ggagcgcatc agccgaccga tgttcgcgtt gctgtcgcag gcccaaccgt gccaccgccg | 720 |
| tggtgtgcaa ggcgcagaag gcggccaggc cgccgctgcc gctgctctgg ccataagtaa | 780 |
| cctaacggcg ccggcttctc cagcaccttc gtggcggcag caggcggggc aacggcagcg | 840 |
| gcacccacgg acggctgctg gttctgctgg tacagcgcca gttgggcgcg caggagctcg | 900 |
| ttctccttgc ggagacgagt aagctcctca tccaccgaca ccatttcatc caccttcgca | 960 |
| acttggcagg cagtgcggta ggcggtaggc gcaggcctca cgctggcgac ccttgagacg | 1020 |
| ggctttgtgc tggctgcacc gcggagcccc gcgccgagcg catccctccg catgaagctc | 1080 |
| ttcattaaat ggaggcgctc gttgatctga gccttgcccc ctgacgaacg gcggtggatg | 1140 |
| gaagatactg ctctcaagtg ctgaagcggt agcttagctc cccgtttcgt gctgatcagt | 1200 |
| cttttcaac acgtaaaaag cggaggagtt ttgcaatttt gttggttgta acgatcctcc | 1260 |
| gttgattttg gcctctttct ccatgggcgg gctgggcgta tttgaagcgg ttctctcttc | 1320 |
| tgccgtta | 1328 |

<210> SEQ ID NO 18
<211> LENGTH: 1889
<212> TYPE: DNA
<213> ORGANISM: Artificial Sequence
<220> FEATURE:
<223> OTHER INFORMATION: Synthetic oligonucleotide

<400> SEQUENCE: 18

| | |
|---|---|
| agaaaatctg gcaccacacc atggtagggt gcgagtgacc ccgcgcgact tggaagggtt | 60 |
| caaacgaccc cgccgtacga acttttgtcg ggggcgctc ccggatggta gggtgcgagt | 120 |
| gaccccgcgc gacttggaag ggttcaaacg accccgccgt acgaactttt gtcggggggc | 180 |
| gctcccggct cgagcatatg gccgccgtca ttgccaagtc ctccgtctcc gcggccgtgg | 240 |
| ctcgcccggc ccgctccagc gtgcgcccca tggccgcgct gaagcccgcc gtcaaggctg | 300 |
| cccccgtggc tgccccggct caggccaacc agatggcgaa caaacacatg tcccttctc | 360 |
| tcttcatcgt cctccttggc ctctcgtgca gcttggcctc cgggcaagtc ctgtttcagg | 420 |
| gttttaactg ggagtcgtgg aagcacaatg gcggtggta caacttcctg atgggcaagg | 480 |
| tggacgacat cgccgccgct ggcgtcacgc acgtgtggct ccccccggcg tcgcagtccg | 540 |
| tcgccgagca agggtacatg ccgggccggc tctacgacct ggacgcctcc aagtacggca | 600 |
| acaaggcgca gctcaagtcc ctcatcggcg cgctccacgg caagggcgtc aaggccatcg | 660 |
| ccgacatcgt catcaaccac cgcacggcgg agcgcaagga cggccgggc atctactgca | 720 |
| tcttcgaggg cggcaccccg gacgcgcgcc tcgactgggg cccccacatg atctgccgcg | 780 |
| acgaccggcc ctacgccgac ggcaccggca cccggacac cggcgccgac ttcggggccg | 840 |
| cgccggacat cgaccacctc aacccgcgcg tccagaagga gctcgtcgag tggctcaact | 900 |
| ggctcaggac cgacgtcggc ttcgacggct ggcgcttcga cttcgccaag gctactccg | 960 |
| cggacgtggc caagatctac gtcgaccgct ccgagcccag cttcgccgtc gccgagatat | 1020 |
| ggacgtcgct ggcgtacggc ggggacggca agccgaacct caaccaggac ccgcaccggc | 1080 |
| aggagctggt gaactgggtg aacaaggtgg gcggctccgg ccccgccacc acgttcgact | 1140 |
| tcaccaccaa gggcatcctc aacgtggccg tggagggcga gctgtggcgc ctgcgcggca | 1200 |
| ccgacggcaa ggcgccgggc atgatcgggt ggtggccggc caaggcggtg accttcgtcg | 1260 |
| acaaccacga caccggctcc acgcagcaca tgtggcccct ccttccgac agggtcatgc | 1320 |

| | | | | |
|---|---|---|---|---|
| agggatatgc | ctacatcctc | acgcacccag | ggaccccatg | catcttctac gatcatttct | 1380 |
| tcgactgggg | cttgaaggag | gagatcgatc | gtctggtgtc | aatcaggacc cgacagggga | 1440 |
| tacacagtga | gagcaagctg | cagatcatgg | aggccgacgc | cgacctttac cttgccgaga | 1500 |
| tcgacggcaa | ggtcatcgtc | aagctcgggc | caagatacga | tgtcggacac ctcattcctg | 1560 |
| aaggcttcaa | ggtggtcgcg | catggcaatg | actatgccgt | atgggagaaa gtataaggct | 1620 |
| gctgccccgg | ctgctgctaa | tctagataaa | tggaggcgct | cgttgatctg agccttgccc | 1680 |
| cctgacgaac | ggcggtggat | ggaagatact | gctctcaagt | gctgaagcgg tagcttagct | 1740 |
| ccccgtttcg | tgctgatcag | tcttttttcaa | cacgtaaaaa | gcggaggagt tttgcaattt | 1800 |
| tgttggttgt | aacgatcctc | cgttgatttt | ggcctctttc | tccatgggcg ggctgggcgt | 1860 |
| atttgaagcg | gttctctctt | ctgccgtta | | | 1889 |

<210> SEQ ID NO 19
<211> LENGTH: 3089
<212> TYPE: DNA
<213> ORGANISM: Artificial Sequence
<220> FEATURE:
<223> OTHER INFORMATION: Synthetic oligonucleotide

<400> SEQUENCE: 19

| | | | | |
|---|---|---|---|---|
| agaaaatctg | gcaccacacc | atggtagggt | gcgagtgacc | ccgcgcgact tggaagggtt | 60 |
| caaacgaccc | cgccgtacga | acttttgtcg | ggggcgctc | ccggatggta gggtgcgagt | 120 |
| gaccccgcgc | gacttggaag | ggttcaaacg | accccgccgt | acgaactttt gtcgggggc | 180 |
| gctcccggat | ggccgccgtc | attgccaagt | cctccgtctc | cgcggccgtg gctcgcccgg | 240 |
| cccgctccag | cgtgcgcccc | atggccgcgc | tgaagcccgc | cgtcaaggct gccccgtgg | 300 |
| ctgccccggc | tcaggccaac | cagatggcgg | atgcgaaagc | aaacggaaag aatgaggcgg | 360 |
| ccaaactggc | gaaaattccg | gcggctgcga | atccattggc | taatgaacca tcggcgattg | 420 |
| catcaaatat | aagttaccac | gtgcagtaca | gtcctcattt | ctcgccgact aagttcgagc | 480 |
| cggagcaagc | tttctttgcc | acggcggagg | ttgtccgcga | tcgtcttatt caacaatgga | 540 |
| atgagacata | ccaccatttt | aataaagttg | atccgaagca | aacatactac ctatcaatgg | 600 |
| aatttcttca | aggaaggact | ttgactaatg | caattggcag | tttggacatt cagaatgcat | 660 |
| atgctgatgc | tttaaataat | ttggggcatg | tccttgagga | gatagctgaa caggaaaaag | 720 |
| atgctgcact | aggaaatggt | gggctgggca | ggctagcttc | atgcttctta gactccatgg | 780 |
| caacattgaa | tttgcctgca | tggggttatg | gtttgagata | ccggtatggg ctgttcaagc | 840 |
| agaagatcac | caagcagggt | caagaagaag | ttgctgaaga | ttggcttgag aaatttagtc | 900 |
| cttgggaagt | tgtcaggcat | gatgtggtat | ttccggtcag | attttttggg agtgttatgg | 960 |
| ttaatccaaa | tggaacgaga | aaatggggttg | ggggtgaagt | tgtccaagcc gtagcttatg | 1020 |
| atataccaat | tccagggtac | aaaaccaaga | acactatcag | tcttcgtctc tgggacgcta | 1080 |
| aagctagcgc | tgaggatttc | aatttatttc | agtttaatga | tggacaatac gaatctgctg | 1140 |
| cacagcttca | ttctcgagct | caacagattt | gtgctgtgct | ctaccccggg gattctactg | 1200 |
| aagaagggaa | gcttttaagg | ctgaaacaac | aattctttct | ctgcagtgct tcacttcagg | 1260 |
| atatgattct | tagattcaag | gagaggaaaa | gtggaaggca | gtggtctgaa tttcccagca | 1320 |
| aggtagctgt | acaactgaat | gatactcatc | caacacttgc | aattccagag ttgatgcgat | 1380 |
| tgctaatgga | tgaggaagga | cttggatggg | atgaagcatg | ggatataaca acaaggactg | 1440 |
| ttgcttatac | caatcacaca | gtacttcctg | aagcacttga | gaagtggtca caagcagtaa | 1500 |

```
tgtggaagct tcttcctcgc catatggaaa taattgaaga gattgacaag agattcattg    1560
caatggtccg ctccacaagg agtgaccttg agagtaagat tcccagcatg tgcatcttgg    1620
ataataatcc caaaaagccg gttgttagga tggcaaactt atgtgtagta tctgcgcata    1680
cggtaaatgg tgttgctcag ttgcacagtg atatcttaaa ggccgacttg ttcgctgact    1740
atgtttctct atggccaaac aaactccaaa ataaaactaa tggcattact cctcgtcgat    1800
ggctccggtt ttgcaatcct gagctcagca aaattatcac aaaatggtta aaaaccgatc    1860
agtgggttac gaaccttgac ctgcttgtag gtcttcgtca gtttgctgac aacacagaac    1920
tccaagctga atgggaatct gctaagatgg ccagtaagaa acatttggca gactacatat    1980
ggcgagtaac cggtgtaacg attgatccta atagcttatt tgacatacaa gtcaagcgca    2040
ttcatgaata caagagacaa ctgctaaata ttttgggcgc aatctacaga tacaagaagt    2100
tgaaggagat gagccctcag gagcggaaga aaactactcc acgcaccatt atgtttggag    2160
ggaaagcatt tgcaacatat acaaacgcaa aagaatagt aaagttggtt aatgatgttg    2220
gtgaagtcgt caacaccgat cctgaggtca atagttattt gaaggtggta tttgttccaa    2280
attacaatgt ctctgttgcg gagttgctta ttccaggaag tgagctatct cagcatatta    2340
gcacagcagg catggaggca agtggcacaa gcaacatgaa attttctcta aatggttgcc    2400
tcattatagg aacattggat ggagctaatg tggaaatcag gcaggagata ggagaggaga    2460
atttctttct ctttggtgca ggagcagacc aagtccctaa gctgcggaag gaaagagaag    2520
atggattgtt caaaccagat cctcggtttg aagaggccaa gcaatttata agaagtggag    2580
catttggaag ctatgactac aacccgcttc ttgattccct ggagggaac actggttatg    2640 gtcgtggtga ttatttcta gttggttatg acttcccaag ttacttagag gctcaggaca    2700
gagttgacca agcttacaag gaccggaaga agtggctgaa gatgtctata ttaagtacag    2760
ctggcagtgg gaaattcagc agtgatcgca caattgcaca gtatgctaag gaaatctgga    2820
acataacaga atgccgtaca tcatgataaa tggaggcgct cgttgatctg agccttgccc    2880
cctgacgaac ggcggtggat ggaagatact gctctcaagt gctgaagcgg tagcttagct    2940
ccccgtttcg tgctgatcag tcttttttcaa cacgtaaaaa gcggaggagt tttgcaattt    3000
tgttggttgt aacgatcctc cgttgatttt ggcctctttc tccatgggcg ggctgggcgt    3060
atttgaagcg gttctctctt ctgccgtta                                      3089
```

<210> SEQ ID NO 20
<211> LENGTH: 1949
<212> TYPE: DNA
<213> ORGANISM: Artificial Sequence
<220> FEATURE:
<223> OTHER INFORMATION: Synthetic oligonucleotide

<400> SEQUENCE: 20

```
agaaaatctg gcaccacacc atggtagggt gcgagtgacc ccgcgcgact tggaagggtt      60
caaacgaccc cgccgtacga acttttgtcg ggggcgctc ccggatggta gggtgcgagt     120
gaccccgcgc gacttggaag ggttcaaacg accccgccgt acgaactttt gtcgggggc     180 gctcccggat ggccgccgtc attgccaagt cctccgtctc cgcggccgtg gctcgcccgg     240
cccgctccag cgtgcgcccc atggccgcgc tgaagcccgc cgtcaaggct gccccgtgg     300 ctgccccggc tcaggccaac cagatggcta taacaccccg ccgaaaacct tcccggaagg     360
gatcaatggc tgatatgccg aaggatgtgc ttgaccagct caagacgctg aagagctct     420 tcacagttga ccaggagaag ctgaagcaga tcgttgagca tttcatcaag gagttacaga     480
```

| | |
|---|---|
| agggcctcag tgtcgaaggc ggaaacattc ccatgaacgt gacttgggtt ctgggatttc | 540 |
| ccactggcca tgagaaaggt acatttctgg ctctggacat gggggggcacc aacctgcgcg | 600 |
| tctgcgaaat tgagctctcc gaagagaagg gcgagtttga tgtcacacag tccaagtatc | 660 |
| gaatcccccga agagctcaag agcggtgaat catcagaact atgggaatat attgccgact | 720 |
| gtgtacagca gttcatagaa tactaccatg acggttgcac ggctttgcca gacctgccgc | 780 |
| tgggctttac cttttcgtac cctgctactc aagaatatgt tgaccacggt gtcctacaga | 840 |
| gatggaccaa gggttttgat attgacggcg tcgagggcaa agacgtcgtc ccaatgttag | 900 |
| aagaagcttt ggctaagaag gttaaaaatt cagctctttc cccattttc tttggctata | 960 |
| tggtgctaat tactttacag ggtctcccca ttaaagttgc cgctctagta acgacacga | 1020 |
| ctggcacact tattgcttcc gcctacactg acccagagat gaaaatcggc tgtatcttcg | 1080 |
| gcacaggcgt caacgccgcc tacatggaaa atgcgggctc tatccctaaa atagcccact | 1140 |
| acaatttacc tcccgacacc ccagtcgcta tcaactgcga atacgcgcc ttcgacaacg | 1200 |
| aactcattgt cctccccga acgcagtatg acgacgtatc ccaactacgt aaaccatact | 1260 |
| ccctggactc ctccttccta gccttcatcg aagaagatcc cttcgagaac ctgtcagaaa | 1320 |
| cgcgagatct cttcgaacgc accctgggga tctacgcatt gccctcggag ctagaattct | 1380 |
| gcagacgcct ggcggaattg atcggcacac gtgccgcacg cctctccgct tgcggtgttg | 1440 |
| cggccatctg caagaagaaa aatatcaccc attgccatgt cggagcggac gggtcggtgt | 1500 |
| tcgagaagta cccgcatttc aaggccaggg gcgccagagc cctgcgggag atccttgact | 1560 |
| ggccagatag tgaaccggat cgggttgtga tgagcggagc ggaggatggg tctggcgttg | 1620 |
| gtgcggcgct tattgcggct ttgacgcttg agagggttaa acaagcttct tgggaatgga | 1680 |
| agtacatcgg aagcggtctg tcttaataaa tggaggcgct cgttgatctg agccttgccc | 1740 |
| cctgacgaac ggcggtggat ggaagatact gctctcaagt gctgaagcgg tagcttagct | 1800 |
| ccccgtttcg tgctgatcag tcttttttcaa cacgtaaaaa gcggaggagt tttgcaatttt | 1860 |
| tgttggttgt aacgatcctc cgttgatttt ggcctctttc tccatgggcg ggctgggcgt | 1920 |
| atttgaagcg gttctctctt ctgccgtta | 1949 |

<210> SEQ ID NO 21
<211> LENGTH: 2249
<212> TYPE: DNA
<213> ORGANISM: Artificial Sequence
<220> FEATURE:
<223> OTHER INFORMATION: Synthetic oligonucleotide

<400> SEQUENCE: 21

| | |
|---|---|
| agaaaatctg gcaccacacc atggtagggt gcgagtgacc ccgcgcgact tggaagggtt | 60 |
| caaacgaccc cgccgtacga acttttgtcg ggggcgctc ccggatggta gggtgcgagt | 120 |
| gaccccgcgc gacttggaag ggttcaaacg accccgccgt acgaactttt gtcgggggc | 180 |
| gctcccggat ggccgccgtc attgccaagt cctccgtctc cgcggccgtg gctcgcccgg | 240 |
| cccgctccag cgtgcgcccc atggccgcgc tgaagcccgc cgtcaaggct gccccgtgg | 300 |
| ctgccccggc tcaggccaac cagatgtccg atttctccgt ccagaccatt gccaccacgg | 360 |
| ccttcacaga ccaaaagcct ggaacctctg gtctcagaaa gaaagttact gtgtttcaac | 420 |
| agcctcacta cactgaaaac ttcattcagg ctattctcga tgccattccg gaaggtgccc | 480 |
| aagtgccac tcttgttgta ggaggtgatg gccgttccta caacgacaag gtcatcaact | 540 |
| tgatcgccaa aatcgcctcg gccaacggag tttccaagtt gattttgggt caagacggga | 600 |

```
ttctttccac tccagcaact tcgcatgtaa tcaggatcag gggtgcaact ggaggaatta      660
ttctcactgc ttcacacaac cccggaggcc ccaaaaacga tttgggtatt aagtacaact      720
tgggaaacgg tgcaccagct ccagaatcgg ttaccaacaa gatctatgat gtctccaagg      780
aattgacttc gtacaagctc attgatttac ccgacattga tttgtccaaa acccagaccg      840
tgcaattggg ccctcttgaa gtggaaatca ttgactccac ctctgattac gtagccatgt      900
tgaaggatat ctttgacttc cccttgatca agtcgttcct cgagactgcc actaaggagc      960
agggattcaa ggttttattt gattcgctca atggtgtcac tggcccctac ggctacaaga     1020
tcttcgttga agaattagga ttgcctctta actcaatcca aaattaccac ccattgcctg     1080
actttggtgg tttacaccca gatccaaact tgacctatgc tcatactttg gtcgagaggg     1140
tcgataagga gaatattgcc tttggtgctg catctgatgg tgacggtgac agaaacatga     1200
tctacggtgc tggtaccttt gtttcgcctg gtgactctgt agccatcatc tcggaatacg     1260
ccgattccat cccttacttc aagaagcaag gtgtctacgg tttggccaga tccatgccta     1320
cctctggagc catcgatttg gtagcaaagg ctaaaggatt gaatgtttac gaagtgccaa     1380
ccggttggaa gttcttctgc aacctttcg acgctgacaa gttgagtatc tgtggtgaag     1440
agtcgtttgg aacaggctcc aaccacatca gagaaaagga cggcctttgg gctgtagttg     1500
cctggttgaa cgtgctagca gattacaacg tcaagaatcc agaatccaag acatctattt     1560
ctgtagtgca gaactcgttt tggaagaaat acggaagaac tttcttcact agatatgact     1620
acgaaaacgt atcgtctgaa ggtgctgccg agctcatcaa cttgttgtct tctattgttg     1680
actctaagaa accaggaagt agcttagctg atggctacgt cgtcaaggaa gctgctaact     1740
tctcgtacac cgatttggac ggctctgttt cgtccaacca aggtttgttc atcaagtttg     1800
aaagcggctt gagattcata gtaagattgt ctggtactgg atcatccggt gctacagtca     1860
gattatatct cgaaaagcac tctgccgacg aatccaccta tggcttaggc gtagaccagt     1920
acttagttga tgacatcaag tttgtcttgg acttgttgaa gttcaagcag ttcttgggaa     1980
aggatgaacc agatgttcgt acctagtaaa tggaggcgct cgttgatctg agccttgccc     2040
cctgacgaac ggcggtggat ggaagatact gctctcaagt gctgaagcgg tagcttagct     2100
ccccgtttcg tgctgatcag tcttttttcaa cacgtaaaaa gcggaggagt tttgcaattt     2160
tgttggttgt aacgatcctc cgttgatttt ggcctctttc tccatgggcg ggctgggcgt     2220
atttgaagcg gttctctctt ctgccgtta                                       2249
```

<210> SEQ ID NO 22
<211> LENGTH: 2231
<212> TYPE: DNA
<213> ORGANISM: Artificial Sequence
<220> FEATURE:
<223> OTHER INFORMATION: Synthetic oligonucleotide

<400> SEQUENCE: 22

```
agaaaatctg gcaccacacc atggtagggt gcgagtgacc ccgcgcgact tggaagggtt       60
caaacgaccc cgccgtacga acttttgtcg ggggcgctc ccggatggta gggtgcgagt      120
gaccccgcgc gacttggaag ggttcaaacg accccgccgt acgaactttt gtcgggggc      180 gctcccggat ggccgccgtc attgccaagt cctccgtctc cgcggccgtg gctcgcccgg      240
cccgctccag cgtgcgcccc atggccgcgc tgaagcccgc cgtcaaggct gccccgtgg      300 ctgccccggc tcaggccaac cagatgtcca ataactcatt cactaacttc aaactggcca      360
ctgaattgcc agcctggtct aagttgcaaa aaatttatga atctcaaggt aagactttgt      420
```

```
ctgtcaagca agaattccaa aaagatgcca agcgttttga aaaattgaac aagactttca      480
ccaactatga tggttccaaa atcttgttcg actactcaaa gaacttggtc aacgatgaaa      540
tcattgctgc attgattgaa ctggccaagg aggctaacgt caccggtttg agagatgcta      600
tgttcaaagg tgaacacatc aactccactg aagatcgtgc tgtctaccac gtcgcattga      660
gaaacagagc taacaagcca atgtacgttg atggtgtcaa cgttgctcca gaagtcgact      720
ctgtcttgaa gcacatgaag gagttctctg aacaagttcg ttctggtgaa tggaagggtt      780
ataccggtaa gaagatcacc gatgttgtta acatcggtat tggtggttcc gatttgggtc      840
cagtcatggt cactgaggct ttgaagcact acgctggtgt cttggatgtc cacttcgttt      900
ccaacattga cggtactcac attgctgaaa ccttgaaggt tgttgaccca gaaactactt      960 tgttttttgat tgcttccaag actttcacta ccgctgaaac tatcactaac gctaacactg     1020
ccaagaactg gttcttgtcg aagacaggta atgatccatc tcacattgct aagcatttcg     1080
ctgctttgtc cactaacgaa accgaagttg ccaagttcgg tattgacacc aaaaacatgt     1140
ttggtttcga agttgggtc ggtggtcgtt actctgtctg gtcggctatt ggtttgtctg      1200
ttgccttgta cattggctat gacaactttg aggctttctt gaagggtgct gaagccgtcg     1260
acaaccactt cacccaaacc ccattggaag acaacattcc attgttgggt ggtttgttgt     1320
ctgtctggta caacaacttc tttggtgctc aaacccattt ggttgctcca ttcgaccaat     1380
acttgcacag attcccagcc tacttgcaac aattgtcaat ggaatctaac ggtaagtctg     1440
ttaccagagg taacgtgttt actgactact ctactggttc tatcttgttt ggtgaaccag     1500
ctaccaacgc tcaacactct ttcttccaat tggttcacca aggtaccaag ttgattccat     1560
ctgatttcat cttagctgct caatctcata acccaattga gaacaaatta catcaaaaga     1620
tgttggcttc aaacttcttt gctcaagctg aagctttaat ggttggtaag gatgaagaac     1680
aagttaaggc tgaaggtgcc actggtggtt tggtcccaca aaggtcttc tcaggtaaca     1740 gaccaactac ctctatcttg gctcaaaaga ttactccagc tactttgggt gctttgattg     1800
cctactacga acatgttact ttcactgaag gtgccatttg gaatatcaac tctttcgacc     1860 aatgggggtgt tgaattgggt aaagtcttgg ctaaagtcat cggcaaggaa ttggacaact     1920
cctccaccat ttctacccac gatgcttcta ccaacggttt aatcaatcaa ttcaaggaat     1980
ggatgtgata aatggaggcg ctcgttgatc tgagccttgc ccctgacga acggcggtgg     2040 atggaagata ctgctctcaa gtgctgaagc ggtagcttag ctccccgttt cgtgctgatc     2100
agtctttttc aacacgtaaa aagcggagga gttttgcaat tttgttggtt gtaacgatcc     2160
tccgttgatt ttggcctctt tctccatggg cgggctgggc gtatttgaag cggttctctc     2220
ttctgccgtt a                                                            2231
```

<210> SEQ ID NO 23  
<211> LENGTH: 56  
<212> TYPE: PRT  
<213> ORGANISM: Artificial Sequence  
<220> FEATURE:  
<223> OTHER INFORMATION: Synthetic peptide

<400> SEQUENCE: 23

Met Ser Ala Leu Val Leu Lys Pro Cys Ala Ala Val Ser Ile Arg Gly  
1               5                   10                  15

Ser Ser Cys Arg Ala Arg Gln Val Ala Pro Arg Ala Pro Leu Ala Ala  
            20                  25                  30

Ser Thr Val Arg Val Ala Leu Ala Thr Leu Glu Ala Pro Ala Arg Arg

```
              35                  40                  45

Leu Gly Asn Val Ala Cys Ala Ala
        50                  55

<210> SEQ ID NO 24
<211> LENGTH: 45
<212> TYPE: PRT
<213> ORGANISM: Artificial Sequence
<220> FEATURE:
<223> OTHER INFORMATION: Synthetic peptide

<400> SEQUENCE: 24

Met Ala Ala Val Ile Ala Lys Ser Ser Val Ser Ala Ala Val Ala Arg
1               5                   10                  15

Pro Ala Arg Ser Ser Val Arg Pro Met Ala Ala Leu Lys Pro Ala Val
            20                  25                  30

Lys Ala Ala Pro Val Ala Ala Pro Ala Gln Ala Asn Gln
        35                  40                  45

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide

<400> SEQUENCE: 25

Met Ala Met Ala Met Arg Ser
1               5

<210> SEQ ID NO 26
<211> LENGTH: 33
<212> TYPE: PRT
<213> ORGANISM: Artificial Sequence
<220> FEATURE:
<223> OTHER INFORMATION: Synthetic peptide

<400> SEQUENCE: 26

Met Leu Ala Ala Lys Ser Ile Ala Gly Pro Arg Ala Phe Lys Ala Ser
1               5                   10                  15

Ala Val Arg Ala Ala Pro Lys Ala Gly Arg Arg Thr Val Val Val Met
            20                  25                  30

Ala

<210> SEQ ID NO 27
<211> LENGTH: 7
<212> TYPE: PRT
<213> ORGANISM: Artificial Sequence
<220> FEATURE:
<223> OTHER INFORMATION: Synthetic peptide

<400> SEQUENCE: 27

Gly Cys Cys Pro Gly Cys Cys
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is any non-cysteine amino acid
<220> FEATURE:
```

```
<221> NAME/KEY: MISC_FEATURE
<222> LOCATION: (4)..(4)
<223> OTHER INFORMATION: Xaa is any non-cysteine amino acid

<400> SEQUENCE: 28

Cys Cys Xaa Xaa Cys Cys
1               5
```

DESIGNER ORGANISMS FOR PHOTOSYNTHETIC PRODUCTION OF ETHANOL FROM CARBON DIOXIDE AND WATER

CROSS-REFERENCE TO RELATED APPLICATION

This Application claims the benefit of U.S. Provisional Application No. 60/826,806, filed on Sep. 25, 2006.

STATEMENT REGARDING FEDERALLY SPONSORED RESEARCH OR DEVELOPMENT

This invention was made with Government support under Contract No. DE-AC05-00OR22725 awarded by the United States Department of Energy. The Government has certain rights in this invention.

FIELD OF THE INVENTION

The present invention generally relates to energy production technology. More specifically, the present invention provides a revolutionary photosynthetic ethanol production methodology based on designer transgenic plants, such as transgenic algae, or plant cells that are created to use the reducing power (NADPH) and energy (ATP) acquired from the photosynthetic process for immediate synthesis of ethanol ($CH_3CH_2OH$) directly from carbon dioxide ($CO_2$) and water ($H_2O$).

BACKGROUND OF THE INVENTION

Ethanol ($CH_3CH_2OH$) can be used as a liquid fuel to run engines such as cars. A significant market for ethanol as a liquid fuel already exists in the current transportation and energy systems. In the United States, currently, ethanol is generated primarily from corn starch using a yeast-fermentation process. Therefore, the "cornstarch ethanol production" process requires a number of energy-consuming steps including agricultural corn-crop cultivation, corn-grain harvesting, corn-grain starch processing, and starch-to-sugar-to-ethanol fermentation. Independent studies have recently shown that the net energy efficiency of the "cornstarch ethanol production" process is actually negative. That is, the "cornstarch ethanol production" process costs more energy than the energy value of its product ethanol. This is not surprising, understandably because the cornstarch that the current technology can use represents only a small fraction of the corn crop biomass that includes the corn stalks, leaves and roots. The cornstovers are commonly discarded in the agricultural fields where they slowly decompose back to $CO_2$, because they represent largely lignocellulosic biomass materials that the current biorefinery industry cannot efficiently use for ethanol production. There are research efforts in trying to make ethanol from lignocellulosic plant biomass materials—a concept called "cellulosic ethanol". However, plant biomass has evolved effective mechanisms for resisting assault on its cell-wall structural sugars from the microbial and animal kingdoms. This property underlies a natural recalcitrance, creating roadblocks to the cost-effective transformation of lignocellulosic biomass to fermentable sugars. Therefore, one of its problems known as the "lignocellulosic recalcitrance" represents a formidable technical barrier to the cost-effective conversion of plant biomass to fermentable sugars. That is, because of the recalcitrance problem, lignocellulosic biomasses (such as cornstover, switchgrass, and woody plant materials) could not be readily converted to fermentable sugars to make ethanol without certain pretreatment, which is often associated with high processing cost. Despite more than 50 years of R&D efforts in lignocellulosic biomass pretreatment and fermentative ethanol-production processing, the problem of recalcitrant lignocellulosics still remains as a formidable technical barrier that has not yet been eliminated so far. Furthermore, the steps of lignocellulosic biomass cultivation, harvesting, pretreatment processing, and cellulose-to-sugar-to-ethanol fermentation all cost energy. Therefore, any new technology that could bypass these bottleneck problems of the biomass technology would be useful.

Algae (such as *Chlamydomonas reinhardtii, Platymonas subcordiformis, Chlorella fusca, Dunaliella salina, Ankistrodesmus braunii,* and *Scenedesmus obliquus*), which can perform photosynthetic assimilation of $CO_2$ with $O_2$ evolution from water in a liquid culture medium with a maximal theoretical solar-to-biomass energy conversion of about 10%, have tremendous potential to be a clean and renewable energy resource. However, the wild-type oxygenic photosynthetic green plants, such as eukaryotic algae, do not possess the ability to produce ethanol directly from $CO_2$ and $H_2O$. As shown in FIG. 1, the wild-type photosynthesis uses the reducing power (NADPH) and energy (ATP) from the photosynthetic water splitting and proton gradient-coupled electron transport process through the algal thylakoid membrane system to reduce $CO_2$ into carbohydrates $(CH_2O)_n$ such as starch with a series of enzymes collectively called the "Calvin cycle" at the stroma region in an algal or green-plant chloroplast. The net result of the wild-type photosynthetic process is the conversion of $CO_2$ and $H_2O$ into carbohydrates $(CH_2O)_n$ and $O_2$ using sunlight energy according to the following process reaction:

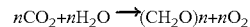

$$nCO_2 + nH_2O \rightarrow (CH_2O)n + nO_2 \qquad [1]$$

The carbohydrates $(CH_2O)n$ are then further converted to all kinds of complicated cellular (biomass) materials including proteins, lipids, and cellulose and other cell-wall materials during cell metabolism and growth.

In certain alga such as *Chlamydomonas reinhardtii*, some of the organic reserves such as starch could be slowly metabolized to ethanol through a secondary fermentative metabolic pathway. The algal fermentative metabolic pathway is similar to the yeast-fermentation process, by which starch is breakdown to smaller sugars such as glucose that is, in turn, transformed into pyruvate by a glycolysis process. Pyruvate may then be converted to formate, acetate, and ethanol by a number of additional metabolic steps (Gfeller and Gibbs (1984) "Fermentative metabolism of *Chlamydomonas reinhardtii,*" *Plant Physiol.* 75:212-218). The efficiency of this secondary metabolic process is quite limited, probably because it could use only a small fraction of the limited organic reserve such as starch in an algal cell. The maximal concentration of ethanol that can be generated by the fermentative algal metabolic process is only about 1%, which is not high enough to become a viable technology for energy production. To be an economically viable technology, the ethanol concentration in a bioreactor medium needs to be able to reach as high as about 3-5% before an ethanol-distillation process could be profitably applied. Therefore, a new ethanol-producing mechanism with a high solar-to-ethanol energy efficiency is needed.

The present invention provides revolutionary designer organisms, which are capable of directly synthesizing ethanol from $CO_2$ and $H_2O$. The ethanol production system provided by the present invention could bypass all of the bottleneck problems of the biomass technology mentioned above.

SUMMARY OF THE INVENTION

The present invention provides revolutionary photosynthetic ethanol production methods based on designer transgenic plants (such as algae) or plant cells. The designer plants and designer plant cells are created through genetic engineering such that the endogenous photosynthesis regulation mechanism is tamed, and the reducing power (NADPH) and energy (ATP) acquired from the photosynthetic water splitting and proton gradient-coupled electron transport process are used for immediate synthesis of ethanol ($CH_3CH_2OH$) directly from carbon dioxide ($CO_2$) and water ($H_2O$). The ethanol production methods of the present invention completely eliminate the problem of recalcitrant lignocellulosics by bypassing the bottleneck problem of the biomass technology. The photosynthetic ethanol-production technology of the present invention is expected to have a much higher solar-to-ethanol energy-conversion efficiency than the current technology.

A fundamental feature of the present photosynthetic ethanol production methodology is to create designer plants (such as algae) or plant cells that contain transgenes coding for a set of enzymes that can act on an intermediate product of the Calvin cycle and convert the intermediate product immediately into ethanol, instead of making starch and other complex biomass materials. Accordingly, the present invention provides, inter alia, methods for producing ethanol based on a designer plant or plant cells, DNA constructs encoding genes of a designer ethanol production pathway, as well as the designer plants and designer plant cells created.

In one aspect, the present invention provides a method for photosynthetic production of ethanol by growing a designer plant (such as a designer alga) or plant cells in a liquid culture medium, wherein the plant or plant cells are genetically engineered to express a set of enzymes in the chloroplast that act on an intermediate product of the Calvin cycle and convert the intermediate product into ethanol.

According to the present invention, a designer plant, such as a designer alga, or designer plant cell for use in the photosynthetic ethanol production can be created utilizing essentially any plant, plant tissue, or plant cells as host, so long as such plant, plant tissue and cells have a photosynthetic capability and can be cultured in a liquid medium. In a preferred embodiment, an aquatic plant (hydrophytes) is utilized to create a designer plant, which includes, but not limited to, submersed aquatic herbs (such as *Hydrilla verticillata, Elodea densa, Aponogeton Boivinianus, Hygrophila Difformmis*), duckweeds (such as *Spirodela polyrrhiza, Wolffia globosa, Landoltia punctata*), water cabbage (*Pistia stratiotes*), buttercups (*Ranunculus*), water caltrop (*Trapa natans* and *Trapa bicornis*), water lily (such as *Nymphaea lotus*), water hyacinth (*Eichhornia crassipes*), seagrasses (such as *Heteranthera Zosterifolia*), and algae.

In an especially preferred embodiment, algae are used as host to create designer algae for photosynthetic ethanol production. Algae suitable for use in the present invention can be either unicellular or multicellular algae (the latter including, but not limited to, seaweeds such as *Ulva latissima* (sea lettuce), *Ascophyllum nodosum*, and *Porphyra tenera*), and include green algae (Chlorophyta), red algae (Rhodophyta), brown algae (Phaeophyta), and diatoms (Bacillariophyta). A particularly preferred species of algae for use in the present invention is a species of green algae, *Chlamydomonas reinhardtii*, of which the genome has recently been sequenced.

The selection of the enzymes appropriate for use to create a designer ethanol-production pathway in a host depends on from which intermediate product of the Calvin cycle the designer pathway branches off from the Calvin cycle. In one embodiment, the designer pathway branches off from the point of glyceraldehydes 3-phosphate and converts it into ethanol by using, for example, the set of enzymes consisting of glyceraldehyde-3-phosphate dehydrogenase, phosphoglycerate kinase, phosphoglycerate mutase, enolase, pyruvate kinase, pyruvate decarboxylase, and alcohol dehydrogenase. In this designer pathway, for conversion of one molecule of glyceraldehyde-3-phosphate to ethanol, an NADH molecule is generated from $NAD^+$ at the step from glyceraldehyde-3-phosphate to 1,3-diphosphoglycerate catalyzed by glyceraldehyde-3-phosphate dehydrogenase while an NADH molecule is converted to $NAD^+$ at the terminal step from acetaldehyde to ethanol catalyzed by alcohol dehydrogenase. That is, the number of NADH molecules consumed is balanced with the number of NADH molecules generated. Therefore, this designer ethanol-production pathway can operate continuously.

In another embodiment, the designer pathway branches off from the point of 3-phosphoglycerate of the Calvin cycle, and is composed of a set of enzymes including, for example, phosphoglycerate mutase, enolase, pyruvate kinase, pyruvate decarboxylase, and alcohol dehydrogenase. In order for this ethanol-production pathway to operate, the alcohol dehydrogenase has to be able to use NADPH that can be generated by the photo-driven electron transport process. Therefore, it is a preferred practice to use an alcohol dehydrogenase that can use NADPH or both NADPH and NADH (i.e., NAD(P)H) for this particular designer ethanol-production pathway. Alternatively, when an alcohol dehydrogenase that can only use NADH is employed, it is preferably here to use an additional embodiment for an NADPH/NADH conversion mechanism in the designer organism's chloroplast to facilitate photosynthetic production of ethanol through this designer pathway.

In still another embodiment, the designer pathway branches off from the point of fructose-1,6-diphosphate and converts it into ethanol by a set of enzymes including, for example, aldolase, triose phosphate isomerase, glyceraldehyde-3-phosphate dehydrogenase, phosphoglycerate kinase, phosphoglycerate mutase, enolase, pyruvate kinase, pyruvate decarboxylase, and alcohol dehydrogenase.

In yet another embodiment, the designer pathway branches off from the point of fructose-6-phosphate and is composed of a set of enzymes including, for example, phosphofructose kinase, aldolase, triose phosphate isomerase, glyceraldehyde-3-phosphate dehydrogenase, phosphoglycerate kinase, phosphoglycerate mutase, enolase, pyruvate kinase, pyruvate decarboxylase, and alcohol dehydrogenase.

It can be noted that certain sets of designer enzymes may permit two or more designer pathways, i.e., pathways that branches off from two or more points of the Calvin cycle for the production of ethanol.

According to the present invention, nucleic acids encoding for these enzymes are genetically engineered such that the enzymes expressed are inserted into the chloroplasts of the host to achieve targeted cellular localization. The targeted insertion of designer ethanol-production-pathway enzymes can be accomplished through use of a nucleotide sequence that encodes for a stroma "signal" peptide, placed in an operable linkage to the nucleotide sequence encoding for a designer enzyme. A number of transit peptide sequences are suitable for use for the targeted insertion of the designer ethanol-production enzymes into chloroplast, including but not limited to the transit peptide sequences of the hydrogenase apoproteins (such as Hyd1), ferredoxin apoprotein (Frx1), thioredoxin m apoprotein (Trx2), glutamine synthase apoprotein (Gs2), LhcII apoproteins, PSII-T apoprotein (PsbT), PSII-S apoprotein (PsbS), PSII-W apoprotein (PsbW), $CF_0CF_1$ subunit-γ apoprotein (AtpC), $CF_0CF_1$ subunit-δ apoprotein (AtpD), $CF_0CF_1$ subunit-II apoprotein (AtpG), photosystem I (PSI) apoproteins (such as, of genes PsaD, PsaE, PsaF, PsaG, PsaH, and PsaK), and Rubisco small-subunit (SSU) apoproteins (such as RbcS2). Preferred transit peptide sequences include the Hyd1 transit peptide, the Frx1 transit peptide, and the Rubisco SSU transit peptides (such as RbcS2).

Further in accordance with the present invention, the expression of the designer ethanol-producing pathway is controlled through the use of an externally inducible promoter so that the designer transgenes are inducibly expressed under certain specific conditions. In one embodiment, the inducible promoter used to control the expression of designer genes is a promoter that is inducible by anaerobiosis, including, for example, the promoters of the hydrogenase gene (Hyd1), the Cyc6 gene encoding the apoprotein of Cytochrome $C_6$, and the Cpx1 gene encoding coprogen oxidase. Additional inducible promoters suitable for use in the present invention include the nitrate reductase (Nia1) promoter, heat-shock protein promoter HSP70A, CabII-1 promoter, Ca1 promoter, and Ca2 promoter.

In another aspect of the present invention, designer DNA constructs are provided, which contain one or more nucleotide sequences encoding one or more designer ethanol-production-pathway enzymes, each of which is placed in an operable linkage to an inducible promoter, and to a nucleotide sequence encoding for an appropriate chloroplast-targeting transit peptide. The constructs may contain additional appropriate sequences, such as a selection marker gene to facilitate the screening and identification of transformants. Nucleic acid constructs carrying designer genes can be delivered into a host alga, plant organism or plant tissue or cells using the available gene-transformation techniques, such as electroporation, PEG induced uptake, and ballistic delivery of DNA, and *Agrobacterium*-mediated transformation.

The designer plants (e.g., designer algae), plant tissues, and plant cells that have been created to contain one or more designer construct, form another embodiment of the present invention.

In a further aspect, the present invention provides additional methods for enhanced photosynthetic ethanol production, the related designer constructs and designer plants, plant tissues and cells.

In a specific embodiment, a photosynthetic ethanol-producing designer plant (for example, a designer alga), plant tissue or cell(s), as described above, has been further modified to contain additional designer transgenes to inducibly express one or more enzymes to facilitate the NADPH/NADH conversion, such as the NADPH phosphatase and NAD kinase, in the stroma region of the algal chloroplast. Alternatively, the alcohol dehydrogenase of the designer plant, plant tissue or cell(s) can be selected/modified so that it can use NADPH as well.

In another embodiment, a photosynthetic ethanol-producing designer plant or plant tissue, or cell(s) has been further modified to inactivate starch-synthesis activity. In a specific embodiment, such further modification includes introduction of a designer DNA construct that encodes and inducibly expresses an interfering RNA (iRNA) molecule that specifically inhibits the synthesis of a starch-synthesis-pathway enzyme, for example, starch synthase, glucose-1-phosphate adenylyltransferase, glucose-phosphate-isomerase and/or phosphoglucomutase for enhanced photobiological production of ethanol.

In still another embodiment, a photosynthetic ethanol-producing designer plant or plant tissue or cell(s) has been further modified to contain an additional set of designer genes that facilitate starch degradation and glycolysis in the stroma. Such additional designer genes include, for example, genes coding for amylase, starch phosphorylase, hexokinase, phosphoglucomutase, and glucose-phosphate-isomerase.

The present invention further provides a process of using a designer plant organism, in combination with a photobiological reactor system and an ethanol separation/harvesting system for photosynthetic production of ethanol and $O_2$ directly from $CO_2$ and $H_2O$ using sunlight. Both industrial $CO_2$ sources and/or atmospheric $CO_2$ from the environment may be used in the photobiological ethanol-production process.

BRIEF DESCRIPTION OF THE DRAWINGS

FIG. 2. A designer organism such as a designer alga becomes a "green machine" for production of ethanol directly from $CO_2$ and $H_2O$ when the designer photosynthetic ethanol-producing pathway(s) is turned on.

FIG. 4D illustrates an ethanol-production pathway of the present invention (shown in blue) branched from the point of fructose-1,6-diphosphate at the Calvin cycle to produce ethanol directly from $CO_2$ and $H_2O$ when the designer photosynthetic ethanol-producing pathway is expressed on under certain specific inducing conditions such as under anaerobic conditions.

FIG. 4E illustrates an ethanol-production pathway of the present invention (shown in blue) branched from the point of fructose-1,6-phosphate at the Calvin cycle to produce ethanol directly from $CO_2$ and $H_2O$ when the designer photosynthetic ethanol-producing pathway is expressed under certain inducing conditions such as under anaerobic conditions. It also illustrates the use of a starch-synthesis inhibitor gene(s) in combination of the designer ethanol-production pathway for further enhanced photosynthetic production of ethanol ($CH_3CH_2OH$) from carbon dioxide ($CO_2$) and water ($H_2O$).

FIG. 6A presents a DNA construct for designer ethanol-production-pathway gene(s).

FIG. 6B presents a DNA construct for NADPH/NADH-conversion designer gene for NADPH/NADH inter-conversion.

FIG. 6C presents a DNA construct for a designer iRNA starch-synthesis inhibitor gene.

FIG. 6D presents a DNA construct for a designer starch-synthase iRNA gene.

FIG. 6E presents a DNA construct for a designer G-1-P adenylyltransferase iRNA gene.

FIG. 6F presents a DNA construct for a designer phosphoglucomutase iRNA gene.

FIG. 6G presents a DNA construct for a designer starch-degradation-glycolysis gene(s).

FIG. 8B illustrates photobiological production of ethanol ($CH_3CH_2OH$) from both the designer 3-phosphoglycerate-branched ethanol-production pathway and the designer starch-to-ethanol pathway in the chloroplast of a designer organism such as a designer alga when both of the designer pathways are expressed.

DETAILED DESCRIPTION OF THE INVENTION

The present invention is directed to a revolutionary photosynthetic ethanol production technology based on designer transgenic plants (e.g., algae) or plant cells. The designer plants and plant cells are created using genetic engineering techniques such that the endogenous photosynthesis regulation mechanism is tamed, and the reducing power (NADPH) and energy (ATP) acquired from the photosynthetic water splitting and proton gradient-coupled electron transport process can be used for immediate synthesis of ethanol ($CH_3CH_2OH$) directly from carbon dioxide ($CO_2$) and water ($H_2O$) according to the following process reaction:

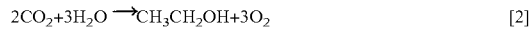

$$2CO_2 + 3H_2O \longrightarrow CH_3CH_2OH + 3O_2 \qquad [2]$$

Figure 2:
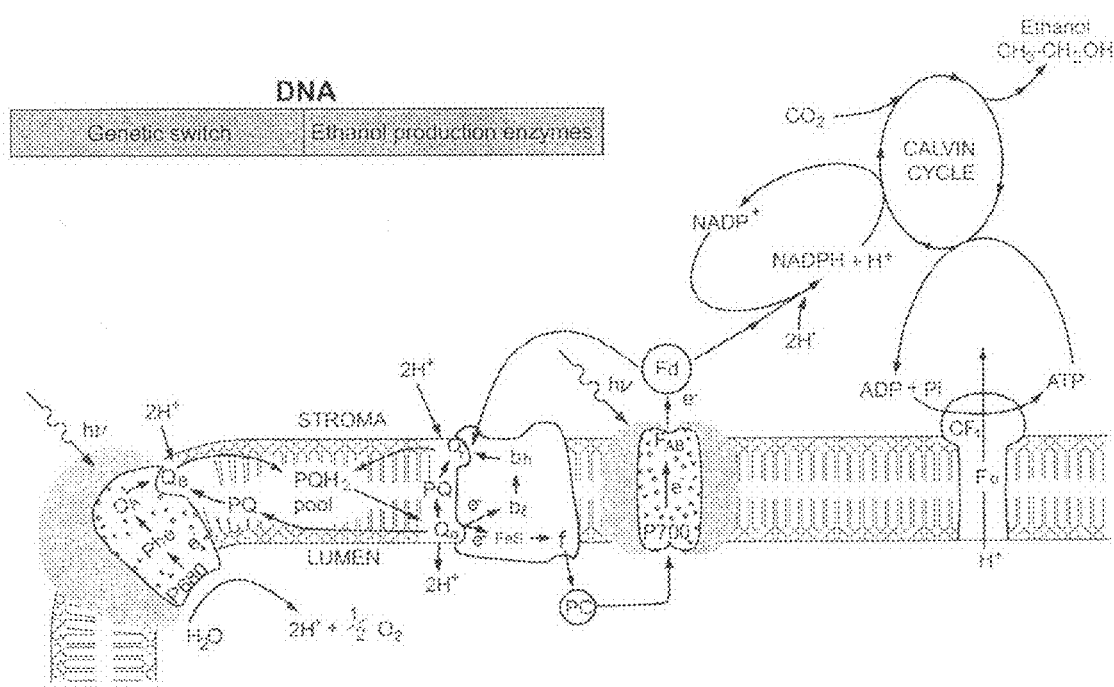

The ethanol production methods of the present invention completely eliminate the problem of recalcitrant lignocellulosics by bypassing the bottleneck problem of the biomass technology. As shown in FIG. 2, the photosynthetic process in a designer organism effectively uses the reducing power (NADPH) and energy (ATP) from the photosynthetic water splitting and proton gradient-coupled electron transport process for immediate synthesis of ethanol ($CH_3CH_2OH$) directly from carbon dioxide ($CO_2$) and water ($H_2O$) without being drained into the other pathway for synthesis of the undesirable lignocellulosic materials that are very hard and often inefficient for the biorefinery industry to use. This approach is also different from the existing "cornstarch ethanol production" process. In accordance with this invention, ethanol will be produced directly from carbon dioxide ($CO_2$) and water ($H_2O$) without having to go through many of the energy consuming steps that the cornstarch ethanol-production process has to go through, including corn crop cultivation, corn-grain harvesting, corn-grain cornstarch processing, and starch-to-sugar-to-ethanol fermentation. As a result, the photosynthetic ethanol-production technology of the present invention is expected to have a much (more than 10-times) higher solar-to-ethanol energy-conversion efficiency than the current technology. Assuming a 10% solar energy conversion efficiency for the proposed photosynthetic ethanol production process, the maximal theoretical productivity (yield) could be about 88,700 kg of ethanol per acre per year, which could support 140 cars (per year per acre). Therefore, this invention could bring a significant capability to the society in helping to ensure energy security. The present invention could also help protect the Earth's environment from the dangerous accumulation of $CO_2$ in the atmosphere, because the present methods convert $CO_2$ directly into clean ethanol energy.

Figure 1:
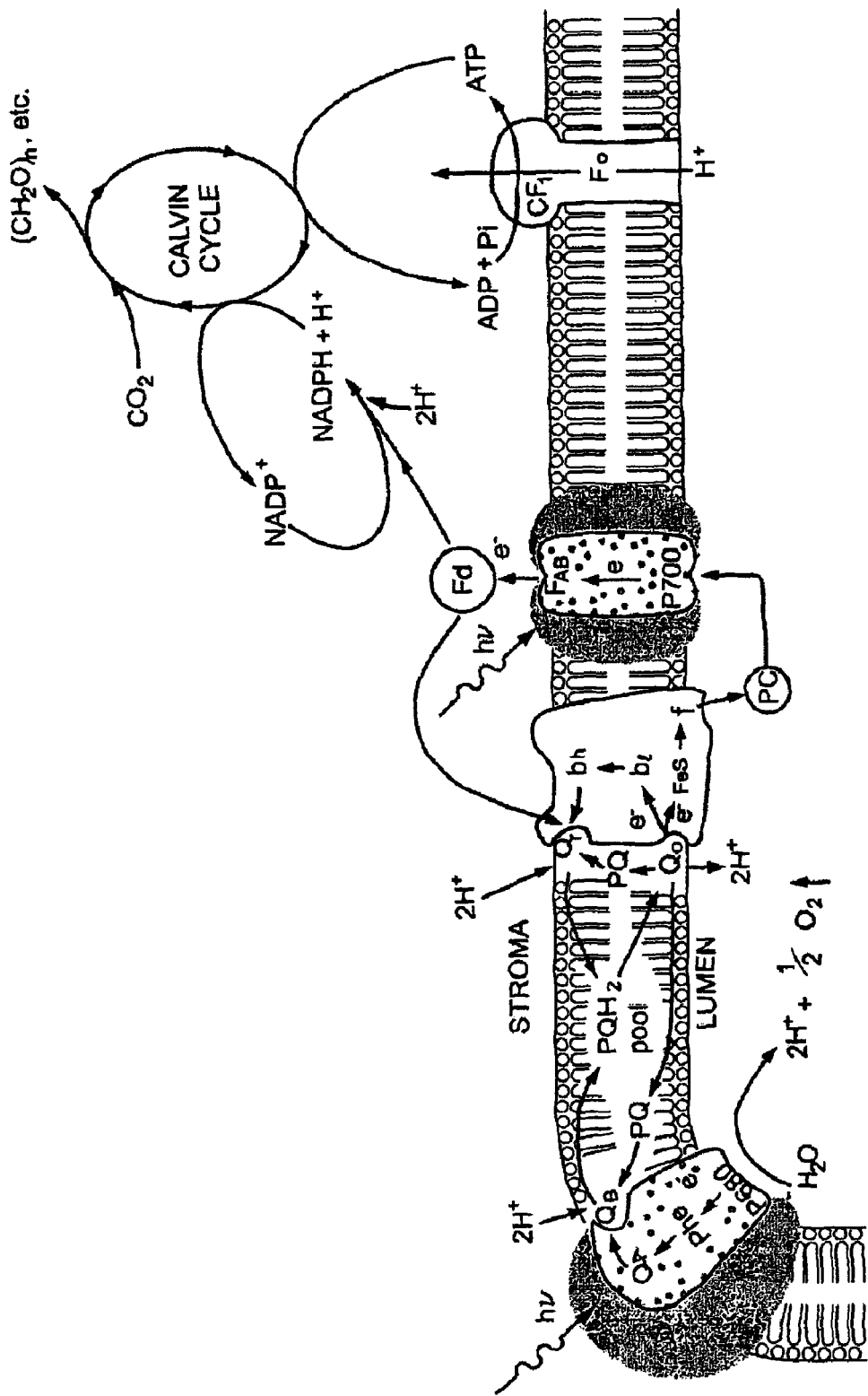
FIG. 1 presents the oxygenic autotrophic photosynthetic pathway, which uses the reducing power (NADPH) and energy (ATP) from the photosynthetic water splitting and proton gradient-coupled electron transport process through the algal thylakoid membrane system to reduce $CO_2$ into carbohydrates $(CH_2O)n$ with a series of enzymes collectively called the "Calvin cycle" in the stroma region of an algal or green-plant chloroplast.

A fundamental feature of the present methodology is utilizing a plant (e.g., an alga) or plant cells, introducing into the plant or plant cells nucleic acid molecules coding for a set of enzymes that can act on an intermediate product of the Calvin cycle and convert the intermediate product into ethanol as illustrated in FIG. 2, instead of making starch and other complicated cellular (biomass) materials as the end products by the wild-type photosynthetic pathway (FIG. 1). Accordingly, the present invention provides, inter alia, methods for producing ethanol based on a designer plant (such as a designer alga), designer plant tissue, or designer plant cells, DNA constructs encoding genes of a designer ethanol production pathway, as well as the designer algae, designer plants, designer plant tissues, and designer plant cells created. The various aspects of the present invention are described in further detail hereinbelow.

Host Plant, Plant Tissue, and Plant Cell

According to the present invention, a designer organism or cell for the photosynthetic ethanol production of the invention can be created utilizing as host, any plant (including alga), plant tissue, or plant cells that have a photosynthetic capability, i.e., an active enzymatic pathway that captures light energy through photosynthesis, using this energy to convert inorganic substances into organic matter. Preferably, the host organism should have an adequate photosynthetic $CO_2$ fixation rate, for example, to support photosynthetic ethanol production from $CO_2$ and $H_2O$ at least about 1,780 kg ethanol per acre per year, more preferably, 8,870 kg ethanol per acre per year, or even more preferably, 88,700 kg ethanol per acre per year.

In a preferred embodiment, an aquatic plant is utilized to create a designer plant. Aquatic plants, also called hydrophytic plants, are plants that live in or on aquatic environments, such as in water (including on or under the water surface) or permanently saturated soil. As used herein, aquatic plants include, for example, algae, submersed aquatic herbs (*Hydrilla verticillata, Elodea densa, Hippuris vulgaris, Aponogeton Boivinianus Aponogeton Rigidifolius, Aponogeton Longiplumulosus, Didiplis Diandra, Vesicularia Dubyana, Hygrophilia Augustifolia, Micranthemum Umbrosum, Eichhornia Azurea, Saururus Cernuus, Cryptocoryne Lingua, Hydrotriche Hottoniiflora Eustralis Stellata, Vallisneria Rubra, Hygrophila Salicifolia, Cyperus Helferi, Cryptocoryne Petchii, Vallisneria americana, Vallisneria Torta, Hydrotriche Hottoniiflora, Crassula Helmsii, Limnophila Sessiliflora, Potamogeton Perfoliatus, Rotala Wallichii, Cryptocoryne Becketii, Blyxa Aubertii, Hygrophila Difformmis*), duckweeds (*Spirodela polyrrhiza, Wolffia globosa, Lemna trisulca, Lemna gibba, Lemna minor, Landoltia punctata*), water cabbage (*Pistia stratiotes*), buttercups (*Ranunculus*), water caltrop (*Trapa natans* and *Trapa bicornis*), water lily (*Nymphaea lotus*, Nymphaeaceae and Nelumbonaceae), water hyacinth (*Eichhornia crassipes*), *Bolbitis heudelotii, Cabomba* sp., seagrasses (*Heteranthera Zosterifolia*, Posidoniaceae, Zosteraceae, Hydrocharitaceae, and Cymodoceaceae). Ethanol produced from an aquatic plant can diffuse into water, permitting normal growth of the plants and more robust production of ethanol from the plants. Liquid cultures of aquatic plant tissues (including, but not limited to, multicellular algae) or cells (including, but not limited to, unicellular algae) are also highly preferred for use, since the ethanol molecules produced from a designer ethanol-production pathway can readily diffuse out of the cells or tissues into the liquid water medium, which can serve as a large pool to store the product ethanol that can be subsequently harvested by filtration and/or distillation techniques.

Although aquatic plants or cells are preferred host organisms for use in the methods of the present invention, tissue and cells of non-aquatic plants, which are photosynthetic and can be cultured in a liquid culture medium, can also be used to create designer tissue or cells for photosynthetic ethanol production. For example, the following tissue or cells of non-aquatic plants can also be selected for use as a host organism in this invention: the photoautotrophic shoot tissue culture of wood apple tree Feronia limonia, the chlorophyllous callus-cultures of corn plant *Zea mays*, the green root cultures of Asteraceae and Solanaceae species, the tissue culture of sugarcane stalk parenchyma, the tissue culture of bryophyte *Physcomitrella patens*, the photosynthetic cell suspension cultures of soybean plant (*Glycine max*), the photoautotrophic and photomixotrophic culture of green Tobacco (*Nicofiana tabacum* L.) cells, the cell suspension culture of *Gisekia pharmaceoides* (a $C_4$ plant), the photosynthetic suspension cultured lines of *Amaranthus powellii* Wats., *Datura innoxia* Mill., *Gossypium hirsutum* L., and *Nicotiana tabacum* x *Nicotiana glutinosa* L. fusion hybrid.

By "liquid medium" is meant liquid water plus relatively small amounts of inorganic nutrients (e.g., N, P, K etc, commonly in their salt forms) for photoautotrophic cultures; and sometimes also including certain organic substrates (e.g., sucrose, glucose, or acetate) for photomixotrophic and/or photoheterotrophic cultures.

In an especially preferred embodiment, the plant utilized in the ethanol production method of the present invention is an alga. The use of algae has several advantages. They can be grown in an open pond at large amounts and low costs. Harvest and purification of ethanol from the water phase is also easily accomplished by distillation or membrane separation.

Algae suitable for use in the present invention include both unicellular algae and multi-unicellular algae. Multicellular algae that can be selected for use in this invention include, but are not limited to, seaweeds such as *Ulva latissima* (sea lettuce), *Ascophyllum nodosum, Codium fragile, Fucus vesiculosus, Eucheuma denticulatum, Gracilaria gracilis, Hydrodictyon reticulatum, Laminaria japonica, Undaria pinntifida, Saccharina japonica, Porphyra yezoensis*, and *Porphyra tenera*. Suitable algae can also be chosen from the following divisions of algae: green algae (Chlorophyta), red algae (Rhodophyta), brown algae (Phaeophyta), and diatoms (Bacillariophyta). Suitable orders of green algae include Ulvales, Ulotrichales, Volvocales, Chlorellales, Schizogoniales, Oedogoniales, Zygnematales, Cladophorales, Siphonales, and Dasycladales. Suitable genera of Rhodophyta are *Porphyra, Chondrus, Cyanidioschyzon, Porphyridium, Gracilaria, Kappaphycus, Gelidium* and *Agardhiella*. Suitable genera of Phaeophyta are *Laminaria, Undaria, Macrocystis, Sargassum* and *Dictyosiphon*. A suitable genus of Cyanophyta is *Phoridium*. Suitable genera of Bacillariophyta are *Cyclotella, Cylindrotheca, Navicula, Thalassiosira*, and *Phaeodactylum*. Preferred species of algae for use in the present invention include *Chlamydomonas reinhardtii, Platymonas subcordiformis, Chlorella fusca, Chlorella sorokiniana, Chlorella vulgaris, 'Chlorella' ellipsoidea, Chlorella* spp., *Dunaliella salina, Dunaliella viridis, Dunaliella bardowil, Haematococcus pluvialis; Parachlorella kessleri, Betaphycus gelatinum, Chondrus crispus, Cyanidioschyzon merolae, Cyanidium caldarium, Galdieria sulphuraria, Gelidiella acerosa, Gracilaria changii, Kappaphycus alvarezii, Porphyra miniata, Ostreococcus tauri, Porphyra yezoensis, Porphyridium* sp., *Palmaria palmata, Gracilaria* spp., *Isochrysis galbana, Kappaphycus* spp., *Laminaria japonica, Laminaria* spp., *Monostroma* spp., *Nannochloropsis oculata, Porphyra* spp., *Porphyridium* spp., *Undaria pinnatifida, Ulva lactuca, Ulva* spp., *Undaria* spp., *Phaeodactylum Tricornutum, Navicula saprophila, Crypthecodinium cohnii, Cylindrotheca fusiformis, Cyclotella cryptica, Euglena gracilis, Amphidinium* sp., *Symbiodinium microadriaticum, Macrocystis pyrifera, Ankistrodesmus braunii*, and *Scenedesmus obliquus*.

Figure 3:
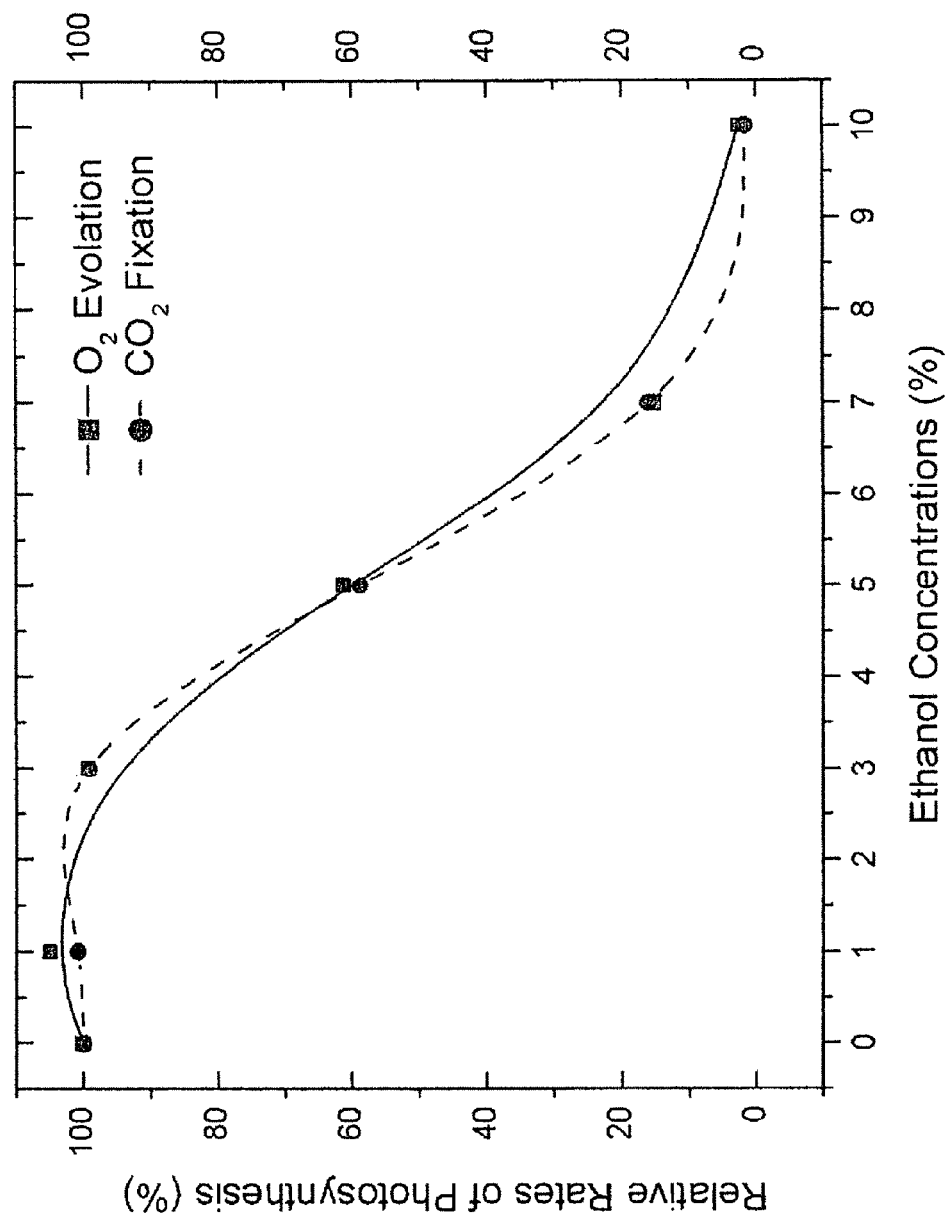
FIG. 3. Ethanol-tolerance assays demonstrated that green alga *Chlamydomonas reinhardtii* is capable of performing photosynthesis at an ethanol concentration as high as 3-5% in the culture medium under anaerobic conditions. The rates of photosynthesis were measured by both the light-dependent $O_2$ evolution and $CO_2$ fixation with various ethanol concentrations, and normalized to that (100%=90 μmol/mg chl·h) of the control culture (0% ethanol).

Proper selection of host organisms for their genetic backgrounds and certain special features is also beneficial. For example, a photosynthetic-ethanol-producing designer alga created from cryophilic algae (psychrophiles) that can grow in snow and ice, and/or from cold-tolerant host strains such as *Chlamydomonas* cold strain CCMG1619, which has been characterized as capable of performing photosynthetic water splitting as cold as 4° C. (Lee, Blankinship and Greenbaum (1995), "Temperature effect on production of hydrogen and oxygen by *Chlamydomonas* cold strain CCMP1619 and wild type 137c," *Applied Biochemistry and Biotechnology* 51/52: 379-386), permits ethanol production even in cold seasons or regions such as Canada. Meanwhile, a designer alga created from a thermophilic photosynthetic organism such as thermophilic algae *Cyanidium caldarium* and *Galdieria sulphuraria* may permit the practice of this invention to be well extended into the hot seasons or areas such as Mexico and the Southwestern region of the United States including Nevada, California, Arizona, New Mexico and Texas, where the weather can often be hot. Furthermore, a photosynthetic-ethanol-producing designer alga created from a marine alga, such as *Platymonas subcordiformis*, permits the practice of this invention using seawater, while the designer alga created from a freshwater alga such as *Chlamydomonas reinhardtii* can use freshwater. Additional optional features of a photosynthetic ethanol-producing designer alga include the benefits of reduced chlorophyll-antenna size, which has been demonstrated to provide higher photosynthetic productivity (Lee, Mets, and Greenbaum (2002). "Improvement of photosynthetic efficiency at high light intensity through reduction of chlorophyll antenna size," *Applied Biochemistry and Biotechnology*, 98-100: 37-48) and ethanol-tolerance and allows for more robust and efficient photosynthetic production of ethanol from $CO_2$ and $H_2O$. For example, it has been demonstrated that *Chlamydomonas reinhardtii*, can tolerate ethanol in the culture medium at a concentration up to about 5-7% (FIG. 3). These optional features can be incorporated into a designer alga, for example, by use of an ethanol-tolerant and/or chlorophyll antenna-deficient mutant (e.g., *Chlamydomonas reinhardtii* strain DS521) as a host organism, for gene transformation with the designer ethanol-production-pathway genes. Therefore, in one of the various embodiments, a host alga is selected from the group consisting of green algae, red algae, brown algae, diatoms, marine algae, freshwater algae, unicellular algae, multicellular algae, seaweeds, cold-tolerant algal strains, heat-tolerant algal strains, ethanol-tolerant algal strains, and combinations thereof.

Creating a Designer Ethanol-Production Pathway in a Host
Selecting Appropriate Designer Enzymes One of the key features in the present invention is the creation of a designer ethanol-production pathway to tame and work with the natural photosynthetic mechanisms to achieve the desirable synthesis of ethanol directly from $CO_2$ and $H_2O$. The natural photosynthetic mechanisms (illustrated in FIG. 1) include (1) the process of photosynthetic water splitting and proton gradient-coupled electron transport through the thylakoid membrane of the chloroplast, which produces the reducing power (NADPH) and energy (ATP), and (2) the Calvin cycle, which reduces $CO_2$ by consumption of the reducing power (NADPH) and energy (ATP).

Figure 4A:
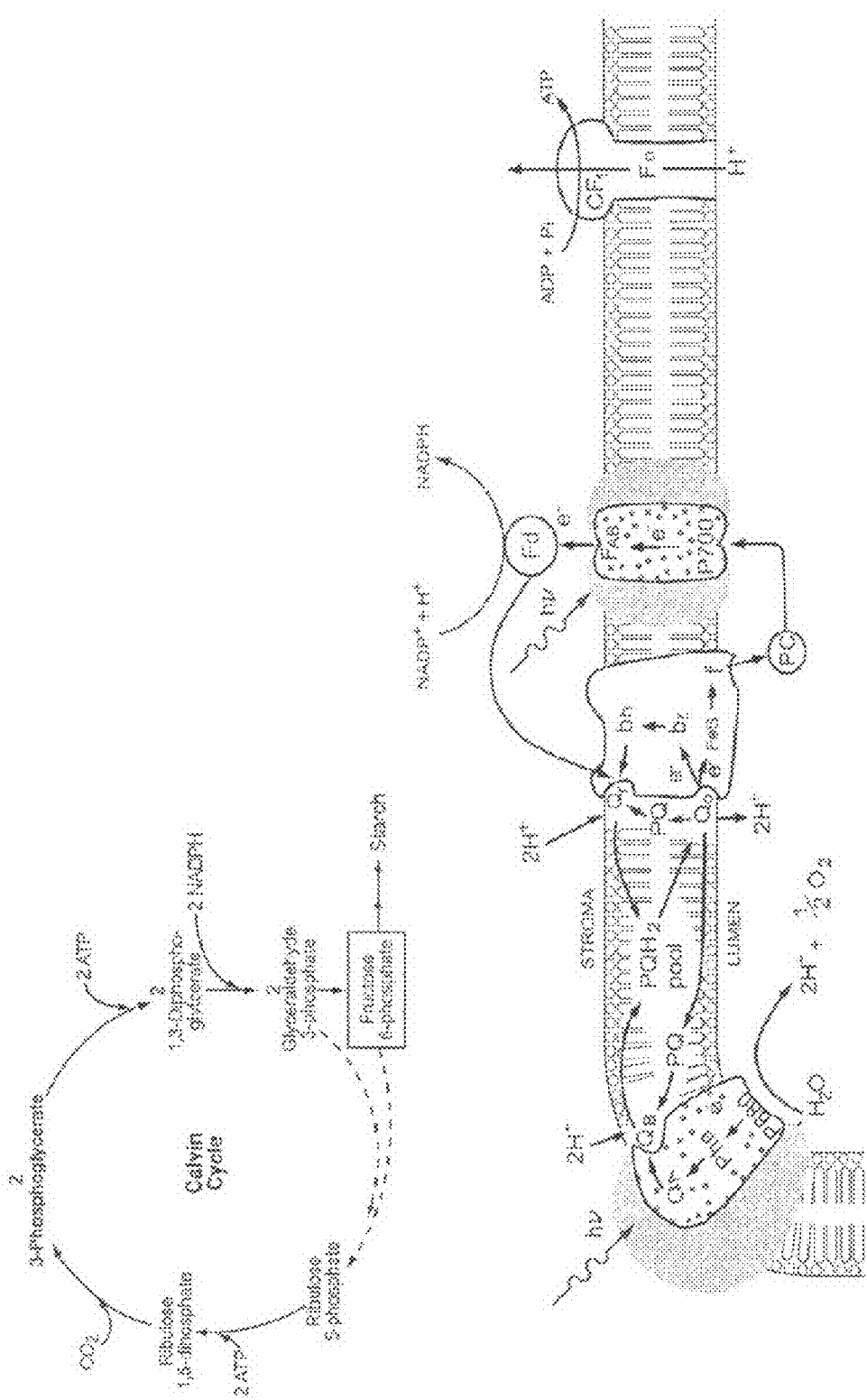
FIG. 4A depicts a designer alga using the normal Calvin cycle to perform photosynthesis for cell growth when the designer ethanol-production genes are switched off under normal aerobic conditions in the absence of an inducing factor.

In accordance with the present invention, a series of enzymes are used to create a designer ethanol-production pathway that takes an intermediate product of the Calvin cycle and converts the intermediate product into ethanol. A "designer ethanol -production-pathway enzyme" is hereby defined as an enzyme that serves as a catalyst for at least one of the steps in a designer ethanol-production pathway. The intermediate products of the Calvin cycle are shown in FIG. 4A. According to the present invention, a number of intermediate products of the Calvin cycle can be utilized to create designer ethanol-production pathway(s); and the enzymes required for a designer ethanol-production pathway are selected depending upon from which intermediate product of the Calvin cycle the designer ethanol-production pathway branches off from the Calvin cycle.

Figure 4B:
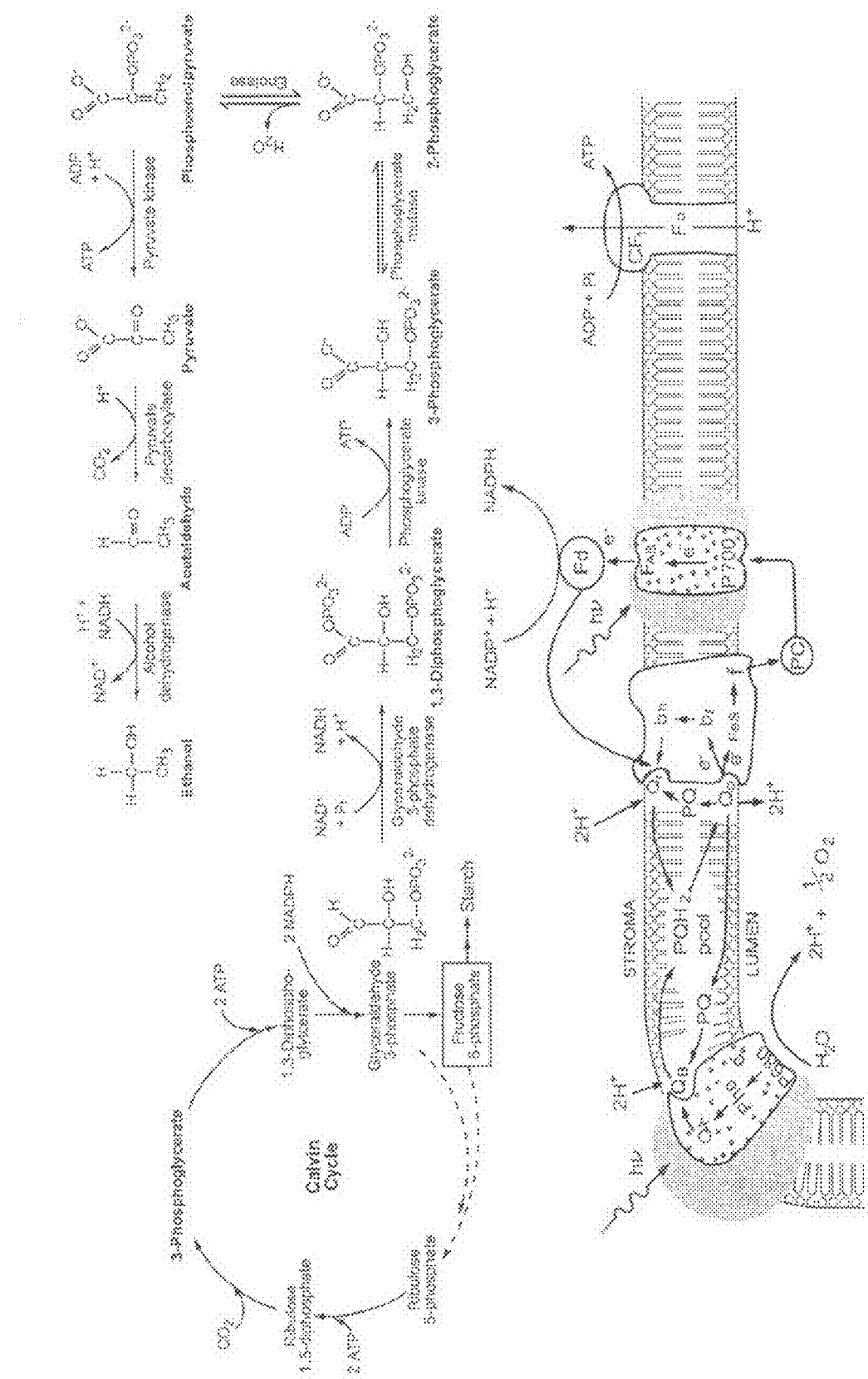
FIG. 4B illustrates an ethanol-production pathway (shown in blue) branched from the point of glyceraldehyde-3-phosphate at the Calvin cycle to produce ethanol directly from $CO_2$ and $H_2O$ when the photosynthetic ethanol-producing pathway is turned on under certain specific inducing conditions such as under anaerobic conditions.

In one example, a designer pathway is created that takes glyceraldehydes-3-phosphate and converts it into ethanol by using, for example, a set of enzymes consisting of glyceraldehyde-3-phosphate dehydrogenase, phosphoglycerate kinase, phosphoglycerate mutase, enolase, pyruvate kinase, pyruvate decarboxylase, and alcohol dehydrogenase, as shown in FIG. 4B. In this designer pathway, for conversion of one molecule of glyceraldehyde-3-phosphate to ethanol, an NADH molecule is generated from $NAD^+$ at the step from glyceraldehyde-3-phosphate to 1,3-diphosphoglycerate catalyzed by glyceraldehyde-3-phosphate dehydrogenase; meanwhile an NADH molecule is converted to $NAD^+$ at the terminal step catalyzed by alcohol dehydrogenase to reduce acetaldehyde to ethanol. Consequently, in this designer pathway (FIG. 4B), the number of NADH molecules consumed is balanced with the number of NADH molecules generated. Therefore, this designer ethanol-production pathway can operate continuously.

Figure 4C:
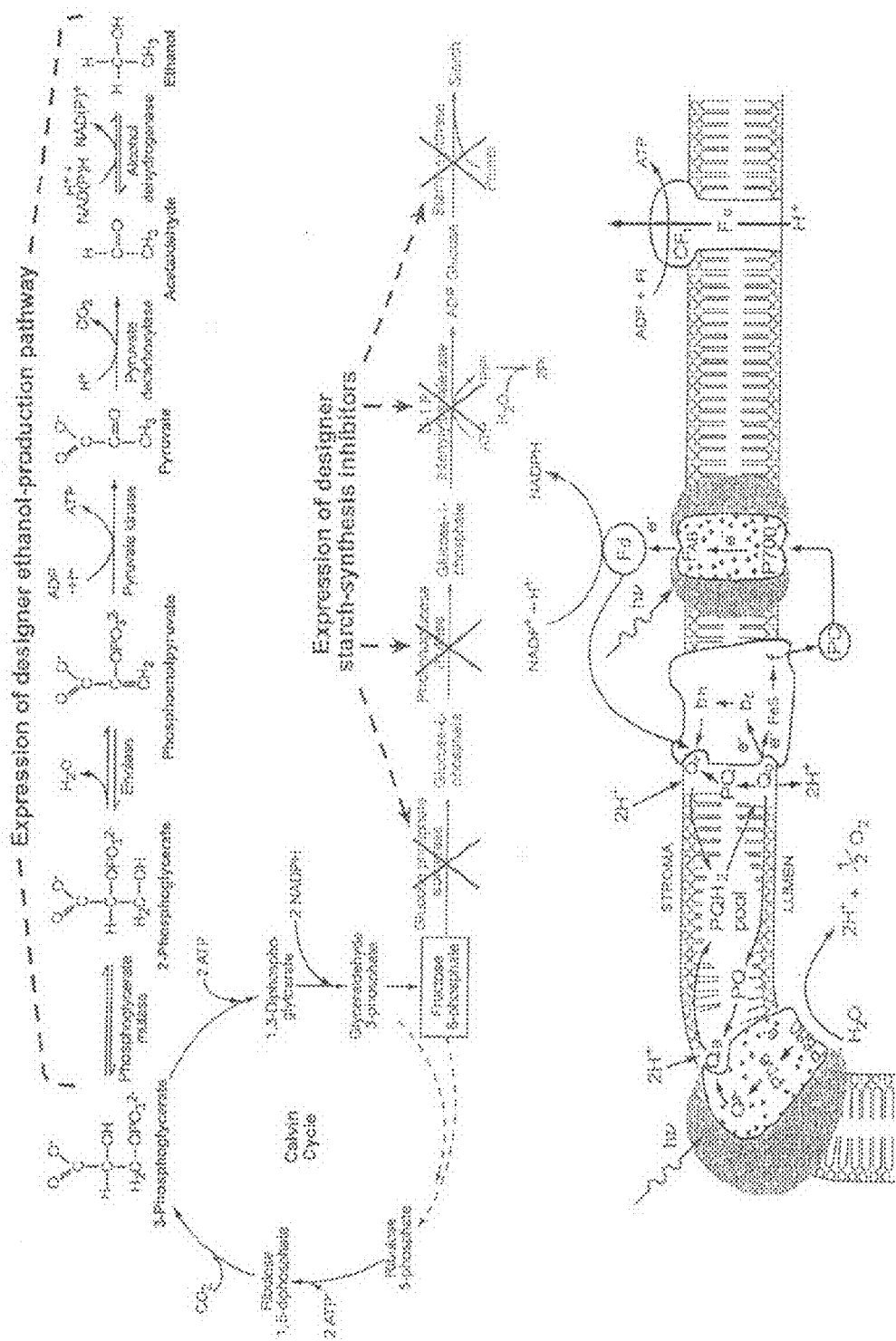
FIG. 4C illustrates an ethanol-production pathway (shown in blue) branched from the point of 3-phosphoglycerate at the Calvin cycle to produce ethanol directly from $CO_2$ and $H_2O$ when the photosynthetic ethanol-producing pathway is turned on under certain specific inducing conditions such as under anaerobic conditions. It also illustrates the use of a starch-synthesis inhibitor gene(s) in combination with the designer ethanol-production pathway for further enhanced photosynthetic production of ethanol $(CH_3CH_2OH)$ from carbon dioxide $(CO_2)$ and water $(H_2O)$ in the chloroplast of a designer organism such as a designer alga.
Figure 4B:
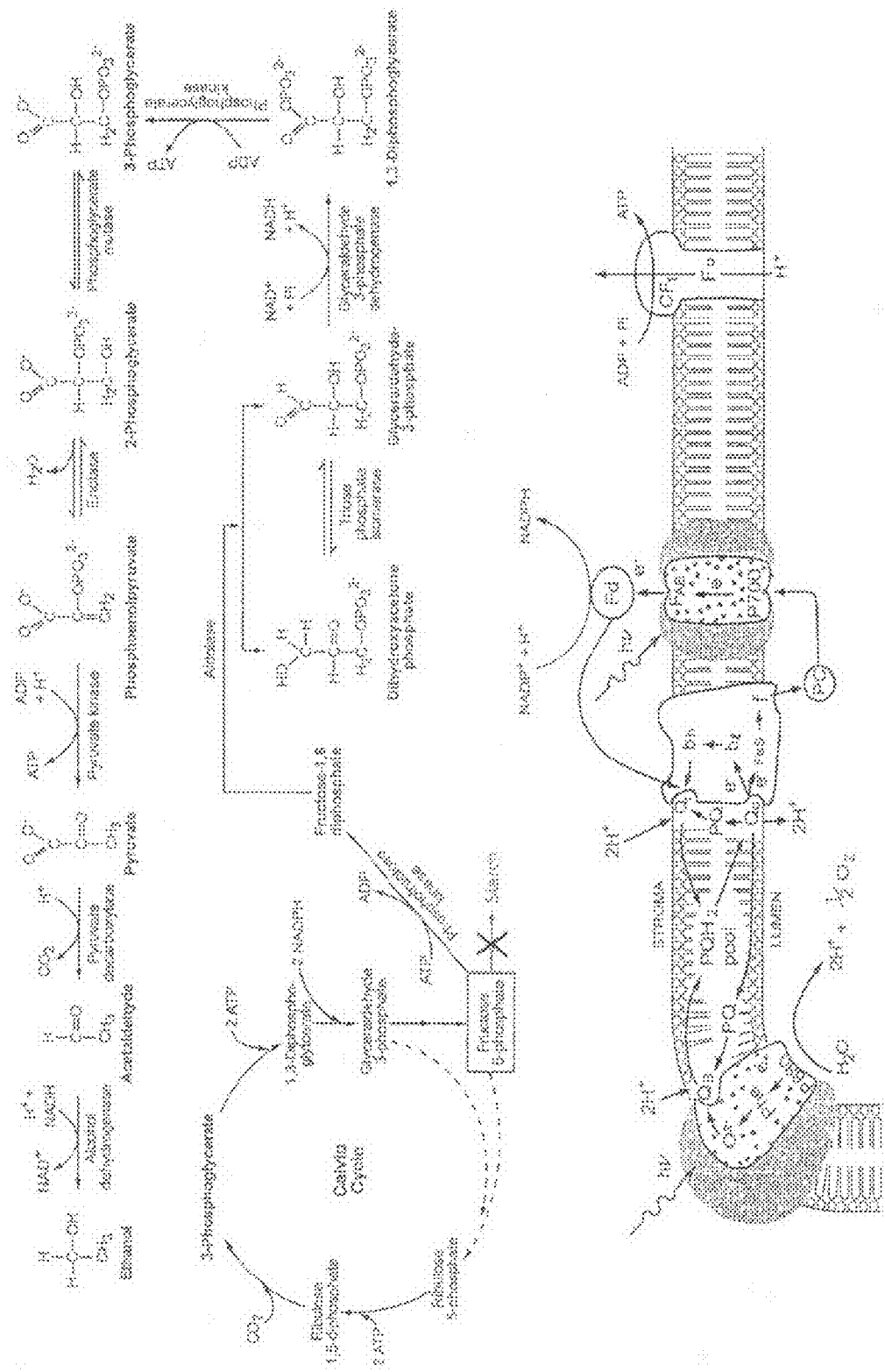

In another example, as shown in FIG. 4C, a designer pathway is created that takes the intermediate product, 3-phosphoglycerate, and converts it into ethanol by using, for example, a set of enzymes consisting of phosphoglycerate mutase, enolase, pyruvate kinase, pyruvate decarboxylase, and alcohol dehydrogenase. It can be seen that the last five enzymes of the designer pathway shown in FIG. 4B are identical with those utilized in the designer pathway shown in FIG. 4C. In other words, the designer enzymes depicted in FIG. 4B permit ethanol production from both the point of 3-phosphoglycerate and the point glyceraldehydes 3-phosphate in the Calvin cycle. These two pathways (FIGS. 4B and 4C), however, have different characteristics. Unlike the glyceraldehyde-3-phosphate-branched ethanol-production pathway (FIG. 4B), the 3-phosphoglycerate-branched pathway which consists of the activities of only five enzymes as shown in FIG. 4C could not itself generate any NADH for use in the terminal step to reduce acetaldehyde to ethanol. That is, if (or when) an alcohol dehydrogenase that can strictly use only NADH but not NADPH is employed, it would require a supply of NADH for the 3-phosphoglycerate-branched pathway to operate. Consequently, in order for the 3-phosphoglycerate-branched ethanol-production pathway (FIG. 4C) to operate, it is important to use an alcohol dehydrogenase that can use NADPH which can be supplied by the photo-driven electron transport process (FIG. 4C, bottom). Therefore, it is a preferred practice to use an alcohol dehydrogenase that can use NADPH or both NADPH and NADH (i.e., NAD(P)H) for this designer ethanol-production pathway (FIG. 4C). Alternatively, when an alcohol dehydrogenase that can use only NADH is employed, it is preferably here to use an additional embodiment that can confer an NADPH/NADH conversion mechanism (to supply NADH by converting NADPH to NADH, see more detail later in the text) in the designer organism's chloroplast to facilitate photosynthetic production of ethanol through the 3-phosphoglycerate-branched designer pathway.

In still another example, a designer pathway is created that takes fructose-1,6-diphosphate and converts it into ethanol by using, for example, a set of enzymes consisting of aldolase, triose phosphate isomerase, glyceraldehyde-3-phosphate dehydrogenase, phosphoglycerate kinase, phosphoglycerate mutase, enolase, pyruvate kinase, pyruvate decarboxylase, and alcohol dehydrogenase, as shown in FIG. 4D, with aldolase and triose phosphate isomerase being the only two additional enzymes relative to the designer pathway depicted in FIG. 4B. The addition of yet one more enzyme in the designer organism, phosphofructose kinase, permits the creation of another designer pathway which branches off from the point of fructose-6-phosphate for the production of ethanol (FIG. 4E). Like the glyceraldehyde-3-phosphate-branched ethanol-production pathway (FIG. 4B), both the fructose-1,6-diphosphate-branched pathway (FIG. 4D) and the fructose-6-phosphate-branched pathway (FIG. 4E) can themselves generate NADH for use in their terminal step to reduce acetaldehyde to ethanol. In each of these designer ethanol-production pathways, the numbers of NADH molecules consumed are balanced with the numbers of NADH molecules generated. Therefore, these designer ethanol-production pathways can operate continuously.

Table 1 lists examples of the enzymes including those identified above for construction of the designer ethanol-production pathways. Throughout this specification, when reference is made to an enzyme, such as, for example, any of the enzymes listed in Table 1, it include their isozymes, functional analogs, designer modified enzymes and combinations thereof. These enzymes can be selected for use in construction of the designer ethanol-production pathways. The "isozymes or functional analogs" refer to certain enzymes that have the same catalytic function but may or may not have exactly the same protein structures. For example, in *Saccharomyces bayanus*, there are four different genes (accession numbers: AY216992, AY216993, AY216994, and AY216995) encoding four alcohol dehydrogenases. These alcohol dehydrogenases essentially have the same function as an alcohol dehydrogenase, although there are some variations in their protein sequences. Therefore, the isozyrnes or functional analogs can also be selected and/or modified for use in construction of the designer ethanol-production pathway. The most essential feature of an enzyme is its active site that catalyzes the enzymatic reaction. Therefore, certain enzyme-protein fragment(s) or subunit(s) that contains such an active catalytic site may also be selected for use in this invention. For various reasons, some of the natural enzymes contain not only the essential catalytic structure but also other structure components that may or may not be desirable for a given application. With techniques of bioinformatics-assisted molecular design, it is possible to select the essential catalytic structure(s) for use in construction of a designer DNA construct encoding a desirable designer enzyme. Therefore, in one of the various embodiments, a designer enzyme gene is created by artificial synthesis of a DNA construct according to bioinformatics-assisted molecular sequence design. With the computer-assisted synthetic biology approach, any DNA sequence (thus its protein structure) of a designer enzyme may be selectively modified to achieve more desirable results by design. Therefore, the terms "designer modified sequences" and "designer modified enzymes" are hereby defined as the DNA sequences and the enzyme proteins that are modified with bioinformatics-assisted molecular design. For example, when a DNA construct for a designer chloroplast-targeted enzyme is designed from the sequence of a mitochondrial enzyme, it is a preferred practice to modify some of the protein structures, for example, by selectively cutting out certain structure component(s) such as its mitochondrial transit-peptide sequence that is not suitable for the given application, and/or by adding certain peptide structures such as an exogenous chloroplast transit-peptide sequence (e.g., a 135-bp Rubisco small-subunit transit peptide (RbcS2)) that is needed to confer the ability in the chloroplast-targeted insertion of the designer protein. Therefore, one of the various embodiments flexibly employs the enzymes, their isozymes, functional analogs, designer modified enzymes, and/or the combinations thereof in construction of the designer ethanol-production pathway(s).

Figure 5:
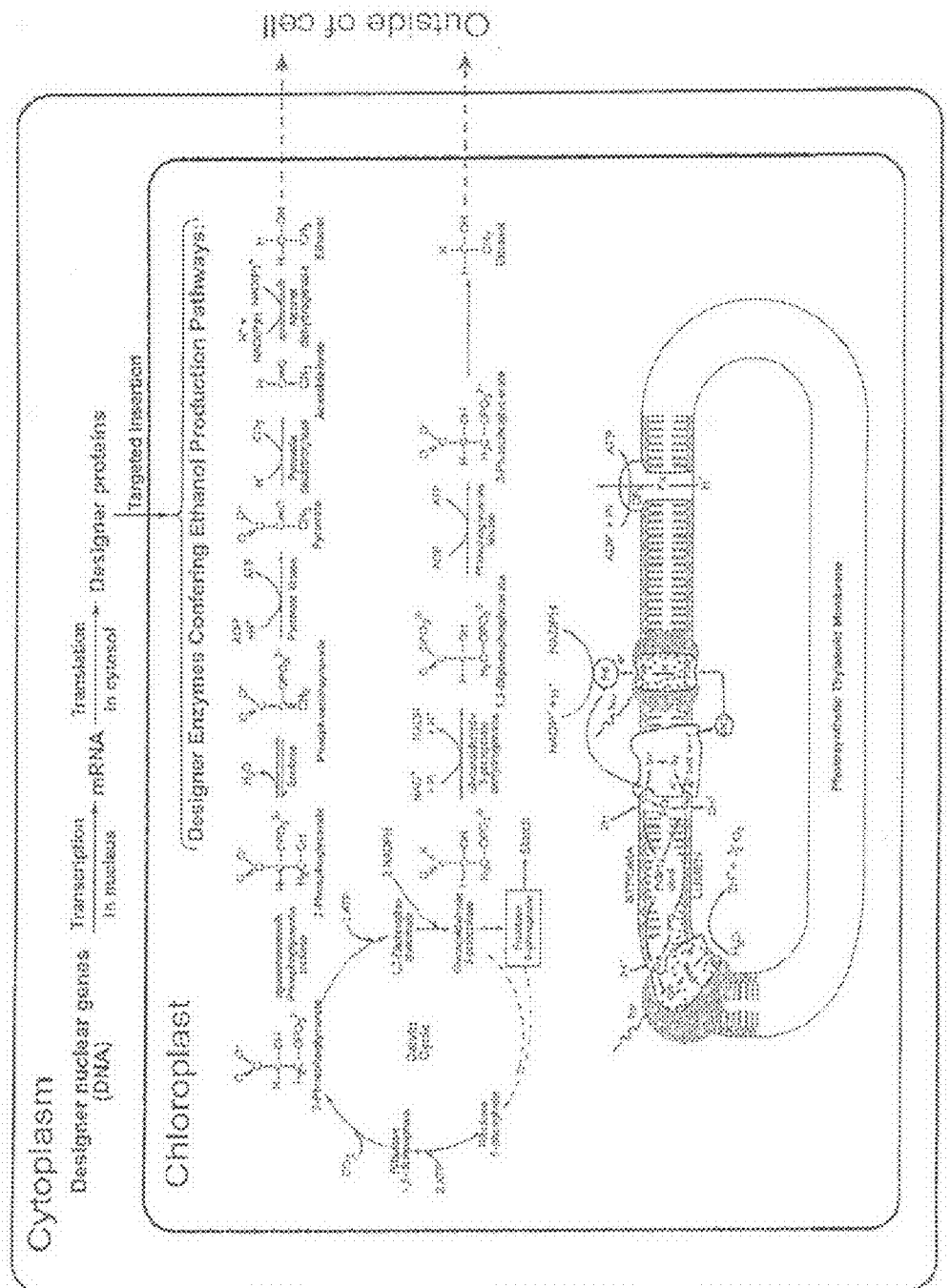
FIG. 5 illustrates how the use of designer nuclear genes including their transcription in nucleus, translation in cytosol, and targeted insertion of designer proteins into chloroplast, can form designer enzymes conferring the function of the designer ethanol-production pathway(s) for enhanced photosynthetic production of ethanol ($CH_3CH_2OH$) from carbon dioxide ($CO_2$) and water ($H_2O$) in the chloroplast of a designer organism such as a designer alga.

As shown in Table 1, many genes of the enzymes identified above have been cloned and/or sequenced from various organisms. Both genomic DNA and/or mRNA sequence data can be used in designing and synthesizing the designer DNA constructs for transformation of a host alga, plant, plant tissue or cells to create a designer organism for photobiological ethanol production (FIG. 5). However, because of possible variations often associated with various source organisms and cellular compartments with respect to a specific host organism and its chloroplast environment where the ethanol-production pathway(s) is designed to work with the Calvin cycle, certain molecular engineering art work in DNA construct design including codon-usage optimization and sequence modification is often necessary for a designer DNA construct (FIG. 6) to work well. For example, if the source sequences are from cytosolic enzymes (sequences), a functional chloroplast-targeting sequence must be added to provide the capability for a designer unclear gene-encoded enzyme to insert into a host chloroplast to confer its function for a designer ethanol-production pathway. Furthermore, to provide the switchability for a designer ethanol-production pathway, it is also important to include a functional inducible promoter sequence such as the promoter of a hydrogenase (Hyd1) or nitrate reductase (Nia1) gene in certain designer DNA construct(s) as illustrated in FIG. 6A to control the expression of the designer gene(s). In addition, as mentioned before, certain functional derivatives or fragments of these enzymes (sequences), chloroplast-targeting transit peptide sequences, and inducible promoter sequences can also be selected for use in full, in part or in combinations thereof, to create the designer organisms according to various embodiments of this invention. The arts in creating and using the designer organisms are further described hereinbelow.

Table 1 lists examples of enzymes for construction of chloroplast ethanol-production pathways.

| Enzyme | Source (Organism) | Genbank Accession Number, JGI Protein ID or Citation |
| --- | --- | --- |
| phosphoglycerate mutase (phosphoglyceromutase) | *Chlamydomonas reinhardtii* cytoplasm; *Aspergillus fumigatus*; *Coccidioides immitis*; *Leishmania braziliensis*; *Ajellomyces capsulatus*; *Monocercomonoides* sp.; *Aspergillus clavatus*; *Arabidopsis thaliana*; *Zea mays* | JGI Chlre2 protein ID 161689, Genbank: AF268078; XM_747847; XM_749597; XM_001248115; XM_001569263; XM_001539892; DQ665859; XM_001270940; NM_117020; M80912 |
| enolase | *Chlamydomonas reinhardtii* cytoplasm; *Arabidopsis thaliana*; | Genbank: X66412, P31683; AK222035; DQ221745; |

| Enzyme | Source (Organism) | Genbank Accession Number, JGI Protein ID or Citation |
|---|---|---|
| | Leishmania Mexicana; Lodderomyces elongisporus; Babesia bavis; Sclerotinia sclerotiorum; Pichia guilliermondii; Spirotrichonympha leidyi; Oryza sativa; Trimastix pyriformis; Leuconostoc mesenteroides; Davidiella tassiana; Aspergillus oryzae; Schizosaccharomyces pombe; Brassica napus; Zea mays | XM_001528071; XM_001611873; XM_001594215; XM_001483612; AB221057; EF122486, U09450; DQ845796; AB088633; U82438; D64113; U13799; AY307449; U17973 |
| pyruvate kinase | Chlamydomonas reinhardtii cytoplasm; Arabidopsis thaliana; Saccharomyces cerevisiae; Babesia bovis; Sclerotinia sclerotiorum; Trichomonas vaginalis; Pichia guilliermondii; Pichia stipitis; Lodderomyces elongisporus; Coccidioides immitis; Trimastix pyriformis; Glycine max (soybean) | JGI Chlre3 protein ID 138105; Genbank: AK229638; AY949876, AY949890, AY949888; XM_001612087; XM_001594710; XM_001329865; XM_001487289; XM_001384591; XM_001528210; XM_001240868; DQ845797; L08632 |
| pyruvate decarboxylase | Chlamydomonas reinhardtii cytoplasm; Pichia stipitis; Lodderomyces elongisporus; Arabidopsis thaliana; Lycoris aurea; Chaetomium globosum; Citrus sinensis; Petunia x hybrida; Candida glabrata; Saccharomyces kluyveri; Zea mays; Rhizopus oryzae; Lotus corniculatus; Zymomonas mobilis; Lachancea kluyveri; Oryza sativa | Chlre3 protein ID 127786, GenBank: E15259; XM_001387668; XM_001526215; NM_121744, NM_124878; DQ996286, DQ996285; XM_001219657; DQ001726; AY928611; AF545432; AY245517, AY245516, AY302469; AF370006; AF282846; AY227204; M15368; AF193853; U38199 |
| alcohol dehydrogenase | Chlamydomonas reinhardtii mitochondria; Kluyveromyces lactis; Kluyveromyces marxianus; Saccharomyces cerevisiae; Saccharomyces bayanus; Pichia stipitis; Entamoeba histolytica; Trichomonas vaginalis; Leishmania braziliensis; Botryotinia fuckeliana; Aspergillus fumigatus; Dianthus caryophyllus; Saccharomyces pastorianus; Lachancea kluyveri | Genbank: AJ620190; XM_451932, X62766, X62767; X60224; Q04894, P25377; AY216992, AY216993, AY216994, AY216995; M88600, XM_001384263; D49910; XM_001315996; XM_001565062; XM_001559311; XM_726411; AY263389; AY217000, AY217001, AY217002, AY217003; AY216997, AY216998, AY216999, AY216996, AF218309; |
| Glyceraldehyde-3-phosphate dehydrogenase | Mesostigma viride cytosol; Triticum aestivum cytosol; Chlamydomonas reinhardtii chloroplast; Botryotinia fuckeliana; Saccharomyces cerevisiae; Zymomonas mobilis; Karenia brevis; Ajellomyces capsulatus; Pichia stipitis; Pichia guilliermondii; Kluyveromyces marxianus, Triticum aestivum; Arabidopsis thaliana | Genbank: DQ873404; EF592180; L27668; XM_001549497; J01324; M18802; EU078558; XM_001539393; XM_001386423, XM_001386568; XM_001485596; DQ681075; EF592180; NM_101214 |
| phosphoglycerate kinase | Chlamydomonas reinhardtii chloroplast; Plasmodium vivax; Babesia bovis; Botryotinia fuckeliana; Monocercomonoides sp.; Lodderomyces elongisporus; Pichia guilliermondii; Arabidopsis thaliana; Helianthus annuus; Oryza sativa; Dictyostelium discoideum; Euglena gracilis; Chondrus crispus; Phaeodactylum tricornutum; Solanum tuberosum | Genbank: U14912, AF244144; XM_001614707; XM_001610679; XM_001548271; DQ665858; XM_001523843; XM_001484377; NM_179576; DQ835564; EF122488; AF316577; AY647236; AY029776; AF108452; AF073473 |
| phosphofructose kinase | Chlamydomonas reinhardtii; Arabidopsis thaliana; Ajellomyces capsulatus; Yarrowia lipolytica; Pichia stipitis; Dictyostelium discoideum; Tetrahymena thermophila; Trypanosoma brucei; Plasmodium falciparum; Spinacia oleracea; | JGI Chlre2 protein ID 159495; Genbank: NM_001037043, NM_179694, NM_119066, NM_125551; XM_001537193; AY142710; XM_001382359, XM_001383014; XM_639070; XM_001017610; XM_838827; XM_001347929; DQ437575; |

-continued

| Enzyme | Source (Organism) | Genbank Accession Number, JGI Protein ID or Citation |
|---|---|---|
| fructose-diphosphate aldolase | Chlamydomonas reinhardtii chloroplast; Fragaria × ananassa cytoplasm; Homo sapiens; Babesia bovis; Trichomonas vaginalis; Pichia stipitis; Arabidopsis thaliana | Genbank: X69969; AF308587; NM_005165; XM_001609195; XM_001312327, XM_001312338; XM_001387466; NM_120057, NM_001036644 |
| triosephosphate isomerase | Arabidopsis thaliana; Chlamydomonas reinhardtii; Sclerotinia sclerotiorum; Chlorella pyrenoidosa; Pichia guilliermondii; Euglena intermedia; Euglena longa; Spinacia oleracea; Solanum chacoense; Hordeum vulgare; Oryza sativa | Genbank: NM_127687, AF247559; AY742323; XM_001587391; AB240149; XM_001485684; DQ459379; AY742325; L36387; AY438596; U83414; EF575877; |
| glucose-1-phosphate adenylyltransferase | Arabidopsis thaliana; Zea mays; Chlamydia trachomatis; Solanum tuberosum (potato); Shigella flexneri; Lycopersicon esculentum | Genbank: NM_127730, NM_124205, NM_121927, AY059862; EF694839, EF694838; AF087165; P55242; NP_709206; T07674 |
| starch synthase | Chlamydomonas reinhardtii; Phaseolus vulgaris; Oryza sativa; Arabidopsis thaliana; Colocasia esculenta; Amaranthus cruentus; Parachlorella kessleri; Triticum aestivum; Sorghum bicolor; Astragalus membranaceus; Perilla frutescens; Zea mays; Ipomoea batatas | Genbank: AF026422, AF026421, DQ019314, AF433156; AB293998; D16202, AB115917, AY299404; AF121673, AK226881; NM_101044; AY225862, AY142712; DQ178026; AB232549; Y16340; AF168786; AF097922; AF210699; AF019297; AF068834 |
| alpha-amylase | Hordeum vulgare aleurone cells; Trichomonas vaginalis; Phanerochaete chrysosporium; Chlamydomonas reinhardtii; Arabidopsis thaliana | Genbank: J04202; XM_001319100; EF143986; AY324649; NM_129551 |
| beta-amylase | Arabidopsis thaliana; Hordeum vulgare; Musa acuminata | Genbank: NM_113297; D21349; DQ166026 |
| Starch phosphorylase | Citrus hybrid cultivar root; Solanum tuberosum chloroplast; Arabidopsis thaliana; Triticum aestivum; Ipomoea batatas | Genbank: AY098895; P53535; NM_113857, NM_114564; AF275551; M64362 |
| phosphoglucomutase | Oryza sativa plastid; Ajellomyces capsulatus; Pichia stipitis; Lodderomyces elongisporus; Aspergillus fumigatus; Arabidopsis thaliana; Populus tomentosa; Oryza sativa; Zea mays | Genbank: AC105932, AF455812; XM_001536436; XM_001383281; XM_001527445; XM_749345; NM_124561, NM_180508, AY128901; AY479974; AF455812; U89342, U89341 |
| Glucosephosphate (glucose-6-phosphate) isomerase | Chlamydomonas reinhardtii; Saccharomyces cerevisiae; Pichia stipitis; Ajellomyces capsulatus; Spinacia oleracea cytosol; Oryza sativa cytoplasm; Arabidopsis thaliana; Zea mays | JGI Chlre3 protein ID 135202; Genbank: M21696; XM_001385873; XM_001537043; T09154; P42862; NM_123638, NM_118595; U17225 |
| Hexokinase (glucokinase) | Ajellomyces capsulatus; Pichia stipitis; Pichia angusta; Thermosynechococcus elongates; Babesia bovis; Solanum chacoense; Oryza sativa; Arabidopsis thaliana | Genbank: XM_001541513; XM_001386652, AY278027; XM_001386035; NC_004113; XM_001608698; DQ177440; DQ116383; NM_112895 |
| NADP(H) phosphatase | Methanococcus jannaschii | The Journal Of Biological Chemistry 280 (47): 39200-39207 (2005) |
| NAD kinase | Babesia bovis; Trichomonas vaginalis | Genbank: XM_001609395; XM_001324239 |

Targeting the Designer Enzymes to the Stroma Region of Chloroplasts

Some of the designer enzymes discussed above, such as the alcohol dehydrogenase, pyruvate decarboxylase, phosphoglycerate mutase and enolase, are known to function in the glycolytic pathway in the cytoplasm, but chloroplasts generally do not possess these enzymes to function with the Calvin cycle. Therefore, nucleic acids encoding for these enzymes need to be genetically engineered such that the enzymes expressed are inserted into the chloroplasts to create a desirable designer organism of the present invention. Depending on the genetic background of a particular host organism, some of the designer enzymes discussed above may exist at some background levels in its native form in a wild-type chloroplast. For various reasons including often the lack of their controllability, however, some of the chloroplast background enzymes may or may not be sufficient to serve as a significant part of the designer ethanol-production pathway(s). Furthermore, a number of useful inducible promoters happen to function in the nuclear genome. For example, both the hydrogenase (Hyd1) promoter and the nitrate reductase (Nia1) promoter that can be used to control the expression of the designer ethanol-production pathways are located in the nuclear genome of *Chlamydomonas reinhardtii*, of which the genome has recently been sequenced. Therefore, it is preferred to use nuclear-genome-encodable designer genes to confer a switchable ethanol-production pathway. Consequently, nucleic acids encoding for these enzymes also need to be genetically engineered with proper sequence modification such that the enzymes are controllably expressed and are inserted into the chloroplasts to create a designer ethanol-production pathway. FIG. 5 illustrates how the use of designer nuclear genes including their transcription in nucleus, translation in cytosol, and targeted insertion of designer proteins into chloroplast, can form the designer enzymes conferring the function of the ethanol-production pathway(s) for photosynthetic production of ethanol ($CH_3CH_2OH$) from carbon dioxide ($CO_2$) and water ($H_2O$) in a designer organism.

Additionally, it is best to express the designer ethanol-producing-pathway enzymes only into chloroplasts (at the stroma region), exactly where the action of the enzymes is needed to enable photosynthetic production of ethanol. If expressed without a chloroplast-targeted insertion mechanism, the enzymes would just stay in the cytosol and not be able to directly interact with the Calvin cycle for ethanol production. Therefore, in addition to the obvious distinctive features in pathway designs and associated approaches, another significant distinction to the prior art is that the present invention innovatively employs a chloroplast-targeted mechanism for genetic insertion of many designer ethanol-production-pathway enzymes into chloroplast to directly interact with the Calvin cycle for photobiological ethanol production.

With a chloroplast stroma-targeted mechanism, the cells will not only be able to produce ethanol but also to grow and regenerate themselves when they are returned to conditions under which the designer pathway is turned off, such as under aerobic conditions when designer hydrogenase promoter-controlled ethanol-production-pathway genes are used. Designer algae, plants, or plant cells that contain normal mitochondria should be able to use the reducing power (NADH) from organic reserves (and/or some exogenous organic substrate such as acetate or sugar) to power the cells immediately after the return to aerobic conditions. Consequently, when the designer algae, plants, or plant cells are returned to aerobic conditions after use under anaerobic conditions for photosynthetic ethanol production, the cells will stop making the ethanol-producing enzymes and start to restore the normal photoautotrophic capability by synthesizing new and functional chloroplasts. Therefore, it is possible to use such genetically engineered designer alga/plant organisms for repeated cycles of photoautotrophic growth under normal aerobic conditions and efficient production of ethanol directly from $CO_2$ and $H_2O$ under certain specific designer ethanol-producing conditions such as under anaerobic conditions.

The targeted insertion of designer ethanol-production enzymes can be accomplished through use of a DNA sequence that encodes for a stroma "signal" peptide. A stroma-protein signal (transit) peptide directs the transport and insertion of a newly synthesized protein into stroma. In accordance with one of the various embodiments, a specific targeting DNA sequence is preferably placed in between the promoter and a designer ethanol-production-pathway enzyme sequence, as shown in a designer DNA construct (FIG. 6A). This targeting sequence encodes for a signal (transit) peptide that is synthesized as part of the apoprotein of an enzyme. The transit peptide guides the insertion of an apoprotein of a designer ethanol-production-pathway enzyme into the chloroplast. After the apoprotein is inserted into the chloroplast, the transit peptide is cleaved off from the apoprotein, which then becomes an active enzyme.

A number of transit peptide sequences are suitable for use for the targeted insertion of the designer ethanol-production-pathway enzymes into chloroplast, including but not limited to the transit peptide sequences of: the hydrogenase apoproteins (such as HydA1 (Hyd1) and HydA2, Genbank accession number AJ308413, AF289201, AY090770), ferredoxin apoprotein (Frx1, accession numbers L10349, P07839), thioredoxin m apoprotein (Trx2, X62335), glutamine synthase apoprotein (Gs2, Q42689), LhcII apoproteins (AB051210, AB051208, AB051205), PSII-T apoprotein (PsbT), PSII-S apoprotein (PsbS), PSII-W apoprotein (PsbW), $CF_0CF_1$ subunit-γ apoprotein (AtpC), $CF_0CF_1$ subunit-δ apoprotein (AtpD, U41442), $CF_0CF_1$ subunit-II apoprotein (AtpG), photosystem I (PSI) apoproteins (such as, of genes PsaD, PsaE, PsaF, PsaG, PsaH, and PsaK), Rubisco SSU apoproteins (such as RbcS2, X04472). Throughout this specification, when reference is made to a transit peptide sequence, such as, for example, any of the transit peptide sequence described above, it includes their functional analogs, modified designer sequences, and combinations thereof. A "functional analog" or "modified designer sequence" in this context refers to a peptide sequence derived or modified (by, e.g., conservative substitution, moderate deletion or addition of amino acids, or modification of side chains of amino acids) based on a native transit peptide sequence, such as those identified above, that has the same function as the native transit peptide sequence, i.e., effecting targeted insertion of a desired enzyme.

In certain specific embodiments, the following transit peptide sequences are used to guide the insertion of the designer ethanol-production-pathway enzymes into the stroma region of the chloroplast: the Hyd1 transit peptide (having the amino acid sequence: msalylkpca avsirgsscr arqvaprapl aastvrvala tleaparrlg nvacaa (SEQ ID NO: 23)), the RbcS2 transit peptides (having the amino acid sequence: maaviakssv saavarpars svrpmaalkp avkaapvaap aqanq (SEQ ID NO: 24)), ferredoxin transit peptide (having the amino acid sequence: mamamrs (SEQ ID NO: 25)), the $CF_0CF_1$ subunit-δ transit peptide (having the amino acid sequence: mlaaksiagp rafkasavra apkagrrtvv vma (SEQ ID NO: 26)), their analogs, functional derivatives, designer sequences, and combinations thereof.

Use of a Genetic Switch to Control the Expression of the Designer Ethanol-producing Pathway.

Another key feature of the invention is the application of a genetic switch to control the expression of the designer ethanol-producing pathway(s), as illustrated in FIG. 2. This switchability is accomplished through the use of an externally inducible promoter so that the designer transgenes are inducibly expressed under certain specific inducing conditions (FIG. 6A). Preferably, the promoter employed to control the expression of designer genes in a host is originated from the host itself or a closely related organism. The activities and inducibility of a promoter in a host cell can be tested by placing the promoter in front of a reported gene, introducing this reporter construct into the host tissue or cells by any of the known DNA delivery techniques, and assessing the expression of the reporter gene.

In a preferred embodiment, the inducible promoter used to control the expression of designer genes is a promoter that is inducible by anaerobiosis, i.e., active under anaerobic conditions but inactive under aerobic conditions. A designer alga/ plant organism can perform autotrophic photosynthesis using $CO_2$ as the carbon source under aerobic conditions (FIG. 4A), and when the designer organism culture is grown and ready for photosynthetic ethanol production, anaerobic conditions will be applied to turn on the promoter and the designer genes (FIG. 4B).

A number of promoters that become active under anaerobic conditions are suitable for use in the present invention. For example, the promoters of the hydrogenase genes (HydA1 (Hyd1) and HydA2, GenBank accession number: AJ308413, AF289201, AY090770) of *Chlamydomonas reinhardtii*, which is active under anaerobic conditions but inactive under aerobic conditions, can be used as an effective genetic switch to control the expression of the designer genes in a host alga, such as *Chlamydomonas reinhardtii*. In fact, *Chlamydomonas* cells contain several nuclear genes that are coordinately induced under anaerobic conditions. These include the hydrogenase structural gene itself (Hyd1), the Cyc6 gene encoding the apoprotein of Cytochrome $C_6$, and the Cpx1 gene encoding coprogen oxidase. The regulatory regions for the latter two have been well characterized, and a region of about 100 bp proves sufficient to confer regulation by anaerobiosis in synthetic gene constructs (Quinn, Barraco, Ericksson and Merchant (2000). "Coordinate copper- and oxygen-responsive Cyc6 and Cpx1 expression in *Chlamydomonas* is mediated by the same element." *J Biol Chem* 275: 6080-6089). Although the above inducible algal promoters may be suitable for use in other plant hosts, especially in plants closely related to algae, the promoters of the homologous genes from these other plants, including higher plants, can be obtained and employed to control the expression of designer genes in those plants.

In another embodiment, the inducible promoter used in the present invention is an algal nitrate reductase (Nia1) promoter, which is inducible by growth in a medium containing nitrate and repressed in a nitrate-deficient but ammonium-containing medium (Loppes and Radoux (2002) "Two short regions of the promoter are essential for activation and repression of the nitrate reductase gene in *Chlamydomonas reinhardtii*," *Mol Genet Genomics* 268: 42-48). Therefore, the Nia1 (gene accession number AF203033) promoter can be selected for use to control the expression of the designer genes in an alga according to the concentration levels of nitrate in a culture medium. Additional inducible promoters that can also be selected for use in the present invention include, for example, the heat-shock protein promoter HSP70A (accession number: DQ059999, AY456093, M98823; Schroda, Blocker, Beek (2000) The HSP70A promoter as a tool for the improved expression of transgenes in *Chlamydomonas*. *Plant Journal* 21:121-131), the promoter of CabII-1 gene (accession number M24072), the promoter of Cal gene (accession number P20507), and the promoter of Ca2 gene (accession number P24258). Throughout this specification, when reference is made to inducible promoter, such as, for example, any of the inducible promoters described above, it includes their analogs, functional derivatives, designer sequences, and combinations thereof. A "functional analog" or "modified designer sequence" in this context refers to a promoter sequence derived or modified (by, e.g., substitution, moderate deletion or addition or modification of nucleotides) based on a native promoter sequence, such as those identified hereinabove, that retains the function of the native promoter sequence.

Dna Constructs and Transformation into Plant Cells

DNA constructs are generated in order to introduce designer ethanol-production-pathway genes to a host alga, plant, plant tissue or plant cells. That is, a nucleotide sequence encoding a designer ethanol-production-pathway enzyme is placed in a vector, in an operable linkage to a promoter, preferably an inducible promoter, and in an operable linkage to a nucleotide sequence coding for an appropriate chloroplast-targeting transit-peptide sequence. In a preferred embodiment, nucleic acid constructs are made to have the elements placed in the following 5' (upstream) to 3' (downstream) orientation: an externally inducible promoter, a transit targeting sequence, and a nucleic acid encoding a designer ethanol-production-pathway enzyme, and preferably an appropriate transcription termination sequence. One or more designer genes (DNA constructs) can be placed into one genetic vector. An example of such a construct is depicted in FIG. 6A. As shown in the embodiment illustrated in FIG. 6A, a designer ethanol-production-pathway transgene is a nucleic acid construct comprising: a) a PCR forward primer; b) an externally inducible promoter; c) a transit targeting sequence; d) a designer ethanol-production-pathway-enzyme-encoding sequence with an appropriate transcription termination sequence; and e) a PCR reverse primer.

In accordance with various embodiments, any of the components a) through e) of this DNA construct are adjusted to suit for certain specific conditions. In practice, any of the components a) through e) of this DNA construct are applied in full or in part, and/or in any adjusted combination to achieve more desirable results. For example, when an algal hydrogenase promoter is used as an inducible promoter in the designer ethanol-production-pathway DNA construct, a transgenic designer alga that contains this DNA construct will be able to perform autotrophic photosynthesis (FIG. 4A) using ambient-air $CO_2$ as the carbon source and grows normally under aerobic conditions, such as in an open pond. When the algal culture is grown and ready for ethanol production, the designer transgene(s) can then be expressed by induction under anaerobic conditions because of the use of the hydrogenase promoter. The expression of the designer gene(s) produces a set of designer ethanol-production-pathway enzymes such as those illustrated in FIG. 4B to work with the Calvin cycle in the chloroplast for photobiological ethanol production.

The two PCR primers are a PCR forward primer (PCR FD primer) located at the beginning (the 5' end) of the DNA construct and a PCR reverse primer (PCR RE primer) located at the other end (the 3' end) as shown in FIG. 6A. This pair of PCR primers is designed to provide certain convenience when needed for relatively easy PCR amplification of the designer DNA construct, which is helpful not only during and after the designer DNA construct is synthesized in preparation for gene transformation, but also after the designer DNA construct is delivered into the genome of a host alga for verification of the designer gene in the transformants. For example, after the transformation of the designer gene is accomplished in a *Chlamydomonas reinhardtii*-arg7 host cell using the techniques of electroporation and argininosuccinate lyase (arg7) complementation screening, the resulted transformants can be then analyzed by a PCR DNA assay of their nuclear DNA using this pair of PCR primers to verify whether the entire designer ethanol-production-pathway gene (the DNA construct) is successfully incorporated into the genome of a given transformant. When the nuclear DNA PCR assay of a transformant can generate a PCR product that matches with the predicted DNA size and sequence according to the designer DNA construct, the successful incorporation of the designer proton-channel gene into the genome of the transformant is verified.

Therefore, the various embodiments also teach the associated method to effectively create the designer transgenic algae, plants, or plant cells for photobiological ethanol production. This method, in one embodiment, includes the following steps: a) Selecting an appropriate host alga, plant, plant tissue, or plant cells with respect to their genetic backgrounds and special features in relation to ethanol production; b) Introducing the nucleic acid constructs of the designer proton-channel genes into the genome of said host alga, plant, plant tissue, or plant cells; c) Verifying the incorporation of the designer genes in the transformed alga, plant, plant tissue, or plant cells with DNA PCR assays using the said PCR primers of the designer DNA construct; d) Measuring and verifying the designer organism features such as the inducible expression of the designer ethanol-pathway genes for photosynthetic ethanol production from carbon dioxide and water by assays of mRNA, protein, and ethanol-production characteristics according to the specific designer features of the DNA construct(s) (FIG. 6A).

The above embodiment of the method for creating the designer transgenic organism for photobiological ethanol production can also be repeatedly applied for a plurality of operational cycles to achieve more desirable results. In various embodiments, any of the steps a) through d) of this method described above are adjusted to suit for certain specific conditions. In various embodiments, any of the steps a) through d) of the method are applied in full or in part, and/or in any adjusted combination.

Examples of designer ethanol-production-pathway genes (DNA constructs) are shown in the sequence listings. SEQ ID NO: 1 presents a detailed DNA construct of a designer Glyceraldehyde-3-Phosphate-Dehydrogenase gene including: a PCR FD primer (sequence 1-20), a 262-bp nitrate reductase (Nia1) promoter (21-282), a 135-bp RbcS2 transit peptide (283-417), an enzyme-encoding sequence (418-1434) selected and modified from a *Mesostigma viride* cytosolic glyceraldehyde-3-phosphate dehydrogenase (mRNA) sequence (GenBank accession number DQ873404), a 223-bp RbcS2 terminator (1435-1657), and a PCR RE primer (1658-1677). The 262-bp Nia1 promoter (DNA sequence 21-282) is used as an example of an inducible promoter to control the expression of a designer ethanol-production-pathway Glyceraldehyde-3-Phosphate-Dehydrogenase gene (DNA sequence 418-1434). The 135-bp RbcS2 transit peptide (DNA sequence 283-417) is used as an example to guide the insertion of the designer enzyme (DNA sequence 382-1398) into the chloroplast of the host organism. The RbcS2 terminator (DNA sequence 1435-1657) is employed so that the transcription and translation of the designer gene is properly terminated to produce the designer apoprotein (RbcS2 transit peptide-Glyceraldehyde-3-Phosphate Dehydrogenase) as desired. Because the Nia1 promoter is a nuclear DNA that can control the expression only for nuclear genes, the synthetic ethanol-production-pathway gene in this example is designed according to the codon usage of *Chlamydomonas* nuclear genome. Therefore, in this case, the designer enzyme gene is transcribed in nucleus. Its mRNA is naturally translocated into cytosol, where the mRNA is translated to an apoprotein that consists of the RbcS2 transit peptide (corresponding to DNA sequence 283-417) with its C-terminal end linked together with the N-terminal end of the Glyceraldehyde-3-Phosphate Dehydrogenase protein (corresponding to DNA sequence 418-1434). The transit peptide of the apoprotein guides its transportation across the chloroplast membranes and into the stroma area, where the transit peptide is cut off from the apoprotein. The resulting Glyceraldehyde-3-Phosphate Dehydrogenase then resumes its function as an enzyme for the designer ethanol-production pathway in chloroplast.

The two PCR primers (sequences 1-20 and 1658-1677) are selected from the sequence of a Human actin gene and can be paired with each other. Blasting the sequences against *Chlamydomonas* GenBank found no homologous sequences of them. Therefore, they can be used as appropriate PCR primers in DNA PCR assays for verification of the designer gene in the transformed alga.

SEQ ID NO: 2 presents example 2 for a designer Phosphoglycerate Kinase DNA construct that includes a PCR FD primer (sequence 1-20), a 262-bp nitrate reductase (Nia1) promoter (21-282), a phosphoglycerate-kinase-encoding sequence (283-1665) selected from a *Chlamydomonas reinhardtii* chloroplast phosphoglycerate-kinase sequence including its chloroplast signal peptide and mature enzyme sequence (GenBank: U14912), a 223-bp RbcS2 terminator (1666-1888), and a PCR RE primer (1889-1908). This designer DNA construct is quite similar to example 1, SEQ ID NO: 1, except that a phosphoglycerate-kinase-encoding sequence (DNA sequence 283-1665) selected from a *Chlamydomonas reinhardtii* chloroplast phosphoglycerate-kinase sequence including its chloroplast signal peptide and mature enzyme sequence (GenBank: U14912) is used. Therefore, this is also an example where the sequence of a nuclear-encoded chloroplast enzyme such as the *Chlamydomonas reinhardtii* chloroplast phosphoglycerate kinase can also be used in design and construction of a designer ethanol-production pathway gene when appropriate with a proper inducible promoter such as the Nia1 promoter (DNA sequence 21-282).

SEQ ID NO: 3 presents example 3 for a designer Phosphoglycerate-Mutase DNA construct that includes a PCR FD primer (sequence 1-20), a 262-bp nitrate reductase (Nia1) promoter (21-282), a 9-bp Xho I NdeI site (283-291), a 135-bp RbcS2 transit peptide (292-426), a phosphoglycerate-mutase encoding sequence (427-2097) selected/modified from the sequences of a *Chlamydomonas reinhardtii* cytosolic phosphoglycerate mutase (JGI Chlre2 protein ID 161689, Genbank: AF268078), a 9-bp XbaI site (2098-2106), a 223-bp RbcS2 terminator (2107-2329), and a PCR RE primer (2330-2349). This designer DNA construct is also similar to example 1, SEQ ID NO: 1, except that a phosphoglycerate-mutase encoding sequence (427-2097) selected/modified from the sequences of a *Chlamydomonas reinhardtii* cytosolic phosphoglycerate mutase is used and restriction sites of Xho I NdeI and XbaI are added to make the key components such as the targeting sequence (292-426) and the designer enzyme sequence (427-2097) as a modular unit that can be flexible replaced when necessary to save cost of gene synthesis and enhance work productivity. Please note, the enzyme does not have to a *Chlamydomonas reinhardtii* cytosolic phosphoglycerate mutase; a number of phosphoglycerate mutase enzymes (such as those listed in Table 1) including their isozymes, designer modified enzymes, and functional analogs from other sources such as *Aspergillus fumigatus; Coccidioides immitis; Leishmania braziliensis; Ajellomyces capsulatus; Monocercomonoides* sp.; *Aspergillus clavatus; Arabidopsis thaliana; Zea mays*, can also be selected for use.

SEQ ID NO: 4 presents example 4 for a designer Enolase DNA construct that includes a PCR FD primer (sequence 1-20), a 262-bp Nia1 promoter (21-282), a 9-bp Xho I NdeI site (283-291), a 135-bp RbcS2 transit peptide (292-426), a enolase-encoding sequence (427-1542) selected/modified from the sequences of a *Chlamydomonas reinhardtii* cytosolic enolase (Genbank: X66412, P31683), a 21-bp Lumio tag (1543-1563), a 9-bp XbaI site (1564-1572), a 223-bp RbcS2 terminator (1573-1795), and a PCR RE primer (17961815) at the 3' end. This DNA construct is similar to example 3, SEQ ID NO: 3, except that an enolase-encoding sequence (427-

1542) selected/modified from the sequences of a *Chlamydomonas reinhardtii* cytosolic enolase is used and a 21-bp Lumio tag (corresponding to DNA sequence 1543-1563) is added at the C-terminal end of the enolase sequence. The 21-bp Lumio-tag sequence (1543-1563) is employed here to encode a Lumio peptide sequence Gly-Cys-Cys-Pro-Gly-Cys-Cys (SEQ ID NO: 27), which can become fluorescent when treated with a Lumio reagent that is now commercially available from Invitrogen [https://catalog.invitrogen.com]. Lumio molecular tagging technology is based on an EDT (1,2-ethanedithiol) coupled biarsenical derivative (the Lumio reagent) of fluorescein that binds to an engineered tetracysteine sequence (Keppetipola, Coffman, and et al (2003). Rapid detection of in vitro expressed proteins using Lumio™ technology, *Gene Expression,* 25.3: 7-11). The tetracysteine sequence consists of Cys-Cys-Xaa-Xaa-Cys-Cys (SEQ ID NO: 28), where Xaa is any non-cysteine amino acid such as Pro or Gly in this example. The EDT-linked Lumio reagent allows free rotation of the arsenic atoms that quenches the fluorescence of fluorescein. Covalent bond formation between the thiols of the Lumio's arsenic groups and the tetracysteines prevents free rotation of arsenic atoms that releases the fluorescence of fluorescein (Griffin, Adams, and Tsien (1998), "Specific covalent labeling of recombinant protein molecules inside live cells", *Science,* 281:269-272). This also permits the visualization of the tetracysteine-tagged proteins by fluorescent molecular imaging. Therefore, use of the Lumio tag in this manner enables monitoring and/or tracking of the designer Glyceraldehyde-3-Phosphate Dehydrogenase when expressed to verify whether the designer ethanol-production pathway enzyme is indeed delivered into the chloroplast of a host organism as designed. The Lumio tag (a short 7 amino acid peptide] that is linked to the C-terminal end of the Glyceraldehyde-3-Phosphate Dehydrogenase protein in this example should have minimal effect on the function of the designer enzyme, but enable the designer enzyme molecule to be visualized when treated with the Lumio reagent. Use of the Lumio tag is entirely optional. If the Lumio tag somehow affects the designer enzyme function, this tag can be deleted in the DNA sequence design.

SEQ ID NO: 5 presents example 5 for a designer Pyruvate Kinase DNA construct that includes a PCR FD primer (sequence 1-20), a 84-bp nitrate reductase promoter (21-104), a 9-bp Xho I NdeI site (105-113), a 135-bp RbcS2 transit peptide (114-248), a Pyruvate Kinase-encoding sequence (249-1748) selected/modified from a *Saccharomyces cerevisiae* strain Pyruvate Kinase sequence (GenBank: AY949876), a 21-bp Lumio-tag sequence (1749-1769), a 9-bp XbaI site (1770-1778), a 223-bp RbcS2 terminator (1779-2001), and a PCR RE primer (2002-2021) at the 3' end. This DNA construct is similar to example 4, SEQ ID NO: 4, except that an 84-bp nitrate reductase promoter (21-104) and a Pyruvate Kinase-encoding sequence (249-1748) selected/modified from a *Saccharomyces cerevisiae* strain Pyruvate Kinase sequence are used. The 84-bp nitrate-reductase promoter is artificially created by joining two partially homologous sequence regions (−231 to −201 and −77 to −25 with respect to the start site of transcription) of the native *Chlamydomonas reinhardtii* Nia1 promoter. Experimental studies have demonstrated that the 84-bp sequence is more active than the native Nia1 promoter (Loppes and Radoux (2002) "Two short regions of the promoter are essential for activation and repression of the nitrate reductase gene in *Chlamydomonas reinhardtii,*" *Mol Genet Genomics* 268: 42-48). Therefore, this is also an example where functional synthetic sequences, analogs, functional derivatives and/or designer modified sequences such as the synthetic 84-bp sequence can be selected for use according to various embodiments in this invention.

SEQ ID NO: 6 presents example 6 for a designer Pyruvate Decarboxylase DNA construct that includes a PCR FD primer (sequence 1-20), a 84-bp nitrate reductase (Nia1) promoter (21-104), a 9-bp Xho I NdeI site (105-113), a 135-bp RbcS2 transit peptide (114-248), a Pyruvate Decarboxylase-encoding sequence (249-1958) selected/modified from the sequences of a *Pichia stipitis* pyruvate decarboxylase sequence (GenBank: XM_001387668), a 21-bp Lumio-tag sequence (1959-1979), a 9-bp XbaI site (1980-1988), a 223-bp RbcS2 terminator (1989-2311), and a PCR RE primer (2312-2231) at the 3' end. This DNA construct is also similar to example 4, SEQ ID NO: 4, except that a Pyruvate Decarboxylase-encoding sequence (249-1958) and an 84-bp synthetic Nia1 promoter (21-104) are used. This is another example that functional synthetic sequences can also be selected for use in designer DNA constructs.

SEQ ID NO: 7 presents example 7 for a designer Alcohol Dehydrogenase DNA construct that includes a PCR FD primer (sequence 1-20), a 2×84-bp nitrate reductase (Nia1) promoter (21-188), a 9-bp Xho I NdeI site (189-197), a 135-bp RbcS2 transit peptide (198-332), an Alcohol Dehydrogenase-encoding sequence (333-1376) selected/modified from a *Saccharomyces bayanus* alcohol dehydrogenase sequence (GenBank AY216992), a 21-bp Lumio-tag sequence (1377-1397), a 9-bp XbaI site (1398-1406), a 223-bp RbcS2 terminator (1407-1629), and a PCR RE primer (1630-1649) at the 3' end. This DNA construct is also similar to example 4, SEQ ID NO: 4, except a designer 2×84-bp Nia1 promoter and an Alcohol Dehydrogenase-encoding sequence (333-1376) selected/modified from a *Saccharomyces bayanus* alcohol dehydrogenase sequence are used. The 2×84-bp Nia1 promoter is constructed as a tandem duplication of the 84-bp synthetic Nia1 promoter sequence presented in SEQ ID NO: 6 above. Experimental tests have shown that the 2×84-bp synthetic Nia1 promoter is even more powerful than the 84-bp sequence which is more active than the native Nia1 promoter (Loppes and Radoux (2002) "Two short regions of the promoter are essential for activation and repression of the nitrate reductase gene in *Chlamydomonas reinhardtii,*" *Mol Genet Genomics* 268: 42-48). Use of this type of inducible promoter sequences with various promoter strengths can also help in adjusting the expression levels of the designer enzymes for the ethanol-production pathway(s).

SEQ ID NO: 8 presents example 8 for a designer HydA1-promoter-controlled Phosphoglycerate-Mutase DNA construct that includes a PCR FD primer (sequence 1-20), a 282-bp HydA1 promoter (21-302), a 135-bp RbcS2 transit peptide (303-437), a phosphoglycerate-mutase encoding sequence (438-2108) selected/modified from the sequences of a *Chlamydomonas reinhardtii* cytosolic phosphoglycerate mutase (JGI Chlre2 protein ID 161689, Genbank: AF268078), a 223-bp RbcS2 terminator (2109-2331), and a PCR RE primer (2332-2351). This designer DNA construct is quite similar to example 1, SEQ ID NO:1, except that a 282-bp HydA1 promoter (21-302) and a phosphoglycerate-mutase encoding sequence (438-2108) selected/modified from the sequences of a *Chlamydomonas reinhardtii* cytosolic phosphoglycerate mutase are used. The 282-bp HydA1 promoter (21-302) has been proven active by experimental assays at the inventor's laboratory. Use of the HydA1 promoter (21-302) enables activation of designer enzyme expression by using anaerobic culture-medium conditions.

With the same principle of using an inducible anaerobic promoter and a chloroplast-targeting sequence as that shown in SEQ ID NO: 8 (example 8), SEQ ID NOS: 9-12 show designer-gene examples 9-12. Briefly, SEQ ID NO: 9 presents example 9 for a designer HydA1-promoter-controlled Enolase DNA construct that includes a PCR FD primer (sequence 1-20), a 282-bp HydA1 promoter (21-302), a 135-bp RbcS2 transit peptide (303-437), a Enolase-encoding sequence (438-1553) selected/modified from the sequences of a *Chlamydomonas reinhardtii* cytosolic enolase (Genbank: X66412, P31683), a 223-bp RbcS2 terminator (1554-1776), and a PCR RE primer. (1777-1796). SEQ ID NO: 10 presents example 10 for a designer HydA1-promoter-controlled Pyruvate-Kinase DNA construct that includes a PCR FD primer (sequence 1-20), a 282-bp HydA1 promoter (21-302), a 135-bp RbcS2 transit peptide (303-437), a Pyruvate Kinase-encoding sequence (438-1589) selected/modified from a *Chlamydomonas reinhardtii* cytosolic pyruvate kinase sequence (JGI Chlre3 protein ID 138105), a 223-bp RbcS2 terminator (1590-1812), and a PCR RE primer (1813-1832). SEQ ID NO:11 presents example 11 for a designer HydA1-promoter-controlled Pyruvate-Decarboxylase DNA construct that includes a PCR FD primer (sequence 1-20), a 282-bp HydA1 promoter (21-302), a 135-bp RbcS2 transit peptide (303-437), a Pyruvate Decarboxylase-encoding sequence (438-2147) selected/modified from a *Chlamydomonas reinhardtii* cytosolic Pyruvate Decarboxylase sequence (Chlre3 protein ID 127786), a 223-bp RbcS2 terminator (2148-2370), and a PCR RE primer (2371-2390). SEQ ID NO: 12 presents example 12 for a designer HydA1-promoter-controlled Alcohol-Dehydrogenase DNA construct that includes a PCR FD primer (sequence 1-20), a 282-bp HydA1 promoter (21-302), a 135-bp RbcS2 transit peptide (303-437), an Alcohol Dehydrogenase-encoding sequence (438-3098) selected/modified from the sequences of a *Chlamydomonas reinhardtii* mitochondria alcohol dehydrogenase (GenBank AJ620190), a 223-bp RbcS2 terminator (3099-3321), and a PCR RE primer (3322-3341).

With the same principle of using a 2×84 synthetic Nia1 promoter and a chloroplast-targeting mechanism as mentioned previously, SEQ ID NOS:13-15 show more examples of designer-enzyme DNA-constructs. Briefly, SEQ ID NO: 13 presents example 13 for a designer Fructose-Diphosphate-Aldolase DNA construct that includes a PCR FD primer (sequence 1-20), a 2×84-bp NR promoter (21-188), a Fructose-Diphosphate Aldolase-encoding sequence (189-1313) selected/modified from a C. reinhardtii chloroplast fructose-1,6-bisphosphate aldolase sequence (GenBank: X69969), a 223-bp RbcS2 terminator (1314-1536), and a PCR RE primer (1537-1556). SEQ ID NO: 14 presents example 14 for a designer Triose-Phosphate-Isomerase DNA construct that includes a PCR FD primer (sequence 1-20), a 2×84-bp NR promoter (21-188), a Triose-Phosphate Isomerase-encoding sequence (189-1136) selected and modified from a *Arabidopsis thaliana* chloroplast triosephosphate-isomerase sequence (GenBank: AF247559), a 223-bp RbcS2 terminator (1137-1359), and a PCR RE primer (1360-1379).

SEQ ID NO: 15 presents example 15 for a designer Phosphofructose-Kinase DNA construct that includes a PCR FD primer (sequence 1-20), a 2×84-bp NR promoter (21-188), a 135-bp RbcS2 transit peptide (189-323), a Phosphofructose Kinase-encoding sequence (324-1913) selected/modified from *Arabidopsis thaliana* 6-phosphofructokinase sequence (GenBank: NM_001037043), a 223-bp RbcS2 terminator (1914-2136), and a PCR RE primer (2137-2156).

The nucleic acid constructs, such as those presented in the examples above, may include additional appropriate sequences, for example, a selection marker gene, and an optional biomolecular tag sequence (such as the Lumio tag described in example 4, SEQ ID NO: 4). Selectable markers that can be selected for use in the constructs include markers conferring resistances to kanamycin, hygromycin, spectinomycin, streptomycin, sulfonyl urea, among others, all of which have been cloned and are available to those skilled in the art. Alternatively, the selective marker is a nutrition marker gene that can complement a deficiency in the host organism. For example, the gene encoding argininosuccinate lyase (arg7) can be used as a selection marker gene in the designer construct, which permits identification of transformants when *Chlamydomonas reinhardtii* arg7-(minus) cells are used as host cells.

Nucleic acid constructs carrying designer genes can be delivered into a host alga, plant, or plant tissue or cells using the available gene-transformation techniques, such as electroporation, PEG induced uptake, and ballistic delivery of DNA, and *Agrobacterium*-mediated transformation. For the purpose of delivering a designer construct into algal cells, the techniques of electroporation, glass bead, and biolistic gene-gun can be selected for use as preferred methods; and an alga with single cells or simple thallus structure is preferred for use in transformation. Transformants can be identified and tested based on routine techniques.

The various designer genes can be introduced into host cells sequentially in a step-wise manner, or simultaneously using one construct or in one transformation. For example, the five DNA constructs shown in SEQ ID NO: 8-12 for the five-enzyme ethanol-production pathway of FIG. 4C can be placed into one genetic vector such as p389-Arg7 with a single selection marker (Arg7). Therefore, by use of a plasmid in this manner, it is possible to deliver all the five DNA constructs (designer genes) into an arginine-requiring *Chlamydomonas reinhardtii*-arg7 host (CC-48) in one transformation for expression of the 3-phosphoglycerate-branched ethanol-production pathway (FIG. 4C). When necessary, a transformant containing the five DNA constructs can be further transformed to get more designer genes into its genomic DNA with an additional selection marker such as streptomycin. By using combinations of various designer-enzymes DNA constructs such as those presented in SEQ ID NO: 1-15 in gene transformation with an appropriate host organism, various ethanol-production pathways can be constructed. For example, the designer DNA constructs of SEQ ID NO: 1-7 can be selected for construction of the glyceraldehydes-3-phosphate-branched ethanol-production pathway illustrated in FIG. 4B; The designer DNA constructs of SEQ ID NO: 1-7, 13, and 14 can be selected for construction of the fructose-1,6-diphosphate-branched ethanol-production pathway illustrated in FIG. 4D; and the designer DNA constructs of SEQ ID NO: 1-7 and 13-15 can be selected for construction of the fructose-1,6-phosphate-branched ethanol-production pathway shown in FIG. 4E.

Figure 7:
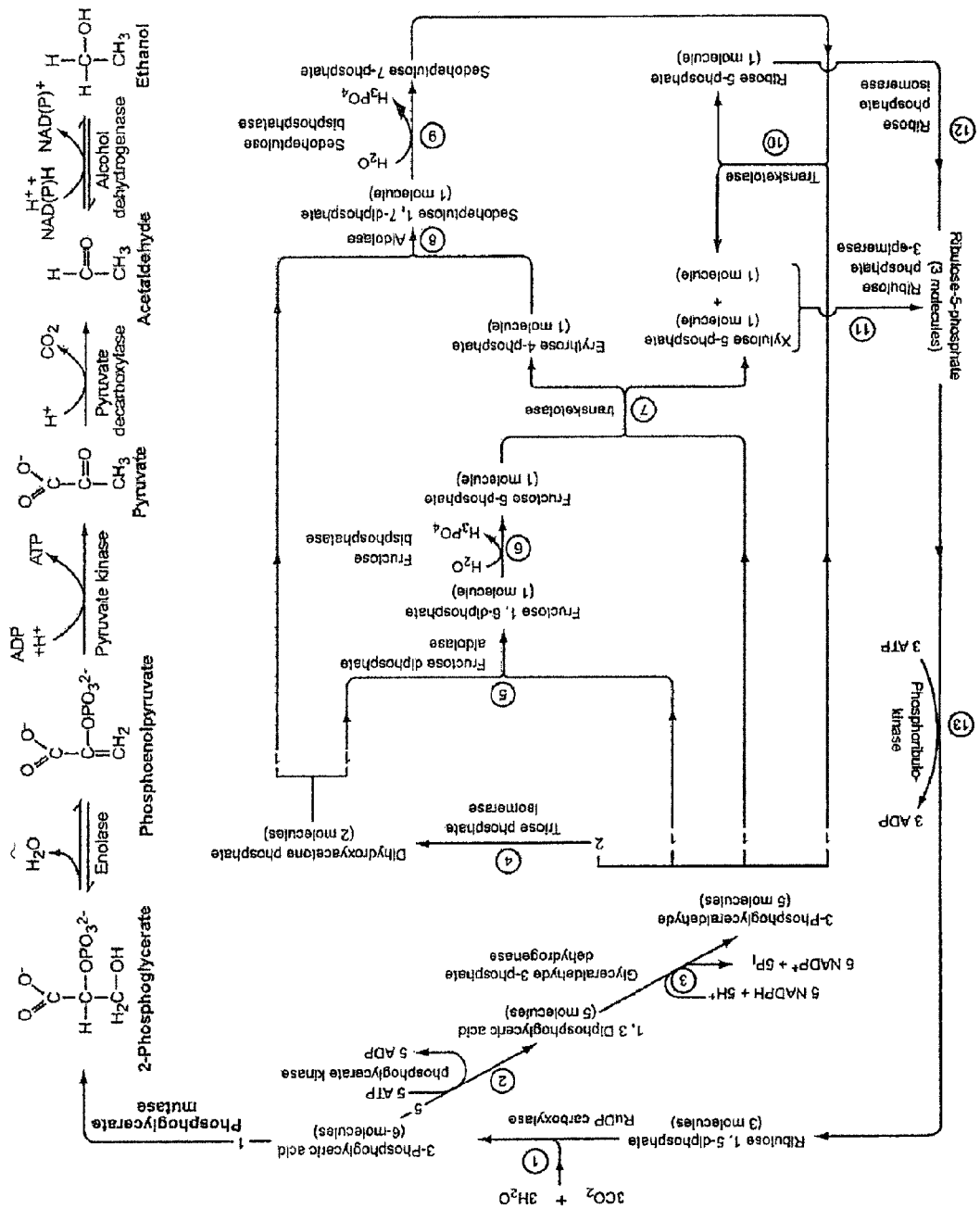
FIG. 7 provides a more-detailed illustration showing how an ethanol-production pathway of the present invention (blue) may work with the Calvin cycle with material (C, H, O) balance for continuous production of ethanol from $CO_2$ and $H_2O$ directly by photosynthesis.

Additional Host Modifications to Enhance Photosynthetic Ethanol Production
An NADPH/NADH Conversion Mechanism According to the photosynthetic ethanol production pathway illustrated in FIG. 4C and FIG. 7, to produce one molecule of ethanol from $2CO_2$ and $3H_2O$ is likely to require 8 ATP and 6 NADPH, both of which are generated by photosynthetic water splitting and photophosphorylation across the thylakoid membrane. In order for the 3-phosphoglycerate-branched ethanol-production pathway (FIG. 4C) to operate, it is a preferred practice to use an alcohol dehydrogenase that can use NADPH that is generated by the photo-driven electron transport process (FIG. 4C, bottom). The NADP(H)-dependent alcohol dehydrogenases (NCBI accession numbers: M88600, Q04894 and P25377) are examples of an alcohol dehydrogenase that can use NADPH. The *Kluyveromyces lactis* mitochondrial KlADH III enzyme (GenBank accession number: XM_451932) is an example of an alcohol dehydrogenase that is capable of accepting either NADP(H) or NAD(H). Such an alcohol dehydrogenase that can use both NADPH and NADH (i.e., NAD(P)H) can also be selected for use in this 3-phosphoglycerate-branched (FIG. 4C) and any of the other designer ethanol-production pathway(s) (FIGS. 4B, 4D, and 4E) as well. When an alcohol dehydrogenase that can only use NADH is employed, it may require an NADPH/NADH conversion mechanism in order for this 3-phosphoglycerate-branched ethanol-production pathway (FIG. 4C) to operate. However, depending on the genetic backgrounds of a host organism, a conversion mechanism between NADPH and NADH may exist in the host so that NADPH and NADH may be interchangeably used in the chloroplast. In addition, it is known that NADPH could be converted into NADH by a NADPH-phosphatase activity (Pattanayak and Chatterjee (1998) "Nicotinamide adenine dinucleotide phosphate phosphatase facilitates dark reduction of nitrate: regulation by nitrate and ammonia," *Biologia Plantarium* 41(1):75-84) and that NAD can be converted to NADP by a NAD kinase activity (Muto, Miyachi, Usuda, Edwards and Bassham (1981) "Light-induced conversion of nicotinamide adenine dinucleotide to nicotinamide adenine dinucleotide phosphate in higher plant leaves," *Plant Physiology* 68(2):324-328; Matsumura-Kadota, Muto, Miyachi (1982) "Light-induced conversion of NAD$^+$ to NADP$^+$ in *Chlorella* cells," *Biochimica Biophysica Acta* 679(2):300-300). Therefore, when enhanced NADPH/NADH conversion is desirable, the host may be genetically modified to enhance the NADPH phosphatase and NAD kinase activities. Thus, in one of the various embodiments, the photosynthetic ethanol-producing designer plant, designer alga or plant cell further contains additional designer transgenes (FIG. 6B) to inducibly express one or more enzymes to facilitate the NADPH/NADH interconversion, such as the NADPH phosphatase and NAD kinase (GenBank: XM_001609395, XM_001324239), in the stroma region of the algal chloroplast.

Another embodiment that can provide an NADPH/NADH conversion mechanism is by properly selecting an appropriate branching point at the Calvin cycle for a designer ethanol-production pathway to branch from. To confer this NADPH/NADH conversion mechanism by pathway design according to this embodiment, it is a preferred practice to branch a designer ethanol-production pathway at or after the point of glyceraldehydes-3-phosphate of the Calvin cycle as shown in FIGS. 4B, 4D, and 4E, and FIG. 8A. In these pathway designs, the NADPH/NADH conversion is achieved essentially by a two-step mechanism: 1) Use of the step with the Calvin-cycle's glyceraldehyde-3-phosphate dehydrogenase, which uses NADPH in reducing 1,3-diphosphoglycerate to glyceraldehydes-3-phosphate; and 2) use of the step with the designer pathway's NAD$^+$-dependent glyceraldehyde-3-phosphate dehydrogenase, which produces NADH in oxidizing glyceraldehyde-3-phosphate to 1,3-diphosphoglycerate. The net result of the two steps described above is the conversion of NADPH to NADH, which can supply the needed reducing power in the form of NADH for the designer ethanol-production pathway(s). For step 1), use of the Calvin-cycle's glyceraldehyde-3-phosphate dehydrogenase naturally in the host organism is usually sufficient. To confer this two-step NADPH/NADH conversion mechanism, it is important to use a NAD$^+$-dependent glyceraldehyde-3-phosphate dehydrogenase in the designer ethanol-production pathway(s). Therefore, in one of the various embodiments, it is a preferred practice to use a NAD$^+$-dependent glyceraldehyde-3-phosphate dehydrogenase, its isozymes, functional derivatives, analogs, designer modified enzymes and/or combinations thereof in the designer ethanol-production pathway(s) as illustrated in FIGS. 4B, 4D, and 4E, and FIG. 8A.

iRNA Techniques to Further Tame Photosynthesis Regulation Mechanism

In another embodiment of the present invention, the host plant or cell is further modified to tame the Calvin cycle so that the host can directly produce liquid fuel ethanol instead of synthesizing starch, celluloses and lignocelluloses that are often inefficient and hard for the biorefinery industry to use. According to the present invention, inactivation of starch-synthesis activity is achieved by suppressing the expression of any of the key enzymes, such as, starch synthase, glucose-1-phosphate (G-1-P) adenylyltransferase, phosphoglucomutase, and hexose-phosphate-isomerase of the starch-synthesis pathway which connects with the Calvin cycle (FIG. 4C).

Introduction of a genetically transmittable factor that can inhibit the starch-synthesis activity that is in competition with designer ethanol-production pathway(s) for the Calvin-cycle products can further enhance photosynthetic ethanol production. In a specific embodiment, a genetically encoded-able inhibitor (FIG. 6C) to the competitive starch-synthesis pathway is an interfering RNA (iRNA) molecule that specifically inhibits the synthesis of a starch-synthesis-pathway enzyme, for example, starch synthase, glucose-1-phosphate (G-1-P) adenylyltransferase, phosphoglucomutase, and/or hexose-phosphate-isomerase. FIGS. 6D-6F depict examples of a designer iRNA gene. The DNA sequences encoding starch synthase iRNA, glucose-1-phosphate (G-1-P) adenylyltransferase iRNA, a phosphoglucomutase iRNA and/or a G-P-isomerase iRNA, respectively, can be designed and synthesized based on RNA interference techniques known to those skilled in the art (Liszewski (Jun. 1, 2003) Progress in RNA interference, *Genetic Engineering News*, Vol. 23, number 11, pp. 1-59). Generally speaking, an interfering RNA (iRNA) molecule is anti-sense but complementary to a normal mRNA of a particular protein (gene) so that such iRNA molecule can specifically bind with the normal mRNA of the particular gene, thus inhibiting (blocking) the translation of the gene-specific mRNA to protein (Fire, Xu, Montgomery, Kostas, Driver, Mello (1998) "Potent and specific genetic interference by double-stranded RNA in *Caenorhabditis elegans*". *Nature* 391(6669):806-11; Dykxhoorn, Novina, Sharp (2003) "Killing the messenger: short RNAs that silence gene expression", *Nat Rev Mol Cell Biol.* 4(6):457-67).

Examples of a designer starch-synthesis iRNA DNA construct (FIG. 6D) are shown in SEQ ID NO: 16 and 17 listed. Briefly, SEQ ID NO: 16 presents example 16 for a designer Nia1-promoter-controlled Starch-Synthase-iRNA DNA construct that includes a PCR FD primer (sequence 1-20), a 262-bp Nia1 promoter (21-282), a Starch-Synthase iRNA sequence (283-617) consisting of start codon atg and a reverse complement sequence of two unique sequence fragments of a *Chlamydomonas reinhardtii* starch-synthase-mRNA sequence (GenBank: AF026422), a 223-bp RbcS2 terminator (618-850), and a PCR RE primer (851-860). Because of the use of a Nia1 promoter (21-282), this designer starch-synthesis iRNA gene is designed to be expressed only when needed to enhance photobiological ethanol production in the presence of its specific inducer, nitrate (NO$_3^-$), which can be added into the culture medium as a fertilizer for induction of the designer organisms. The Starch-Synthase iRNA sequence (283-617) is designed to bind with the normal mRNA of the starch synthase gene, thus blocking its translation into a functional starch synthase. The inhibition of the starch synthase activity in this manner is to channel more photosynthetic products of the Calvin cycle into the ethanol-production pathway(s) as illustrated in FIGS. 4C and 4E.

SEQ ID NO: 17 presents example 17 for a designer HydA1-promoter-controlled Starch-Synthase-iRNA DNA construct that includes a PCR FD primer (sequence 1-20), a 282-bp HydA1 promoter (21-302), a designer Starch-Synthase iRNA sequence (303-1085), a 223-bp RbcS2 terminator (1086-1308), and a PCR RE primer (1309-1328). The designer Starch-Synthase-iRNA sequence (303-1085) comprises of: a 300-bp sense fragment (303-602) selected from the first 300-bp unique coding sequence of a *Chlamydomonas reinhardtii* starch synthase mRNA sequence (GenBank: AF026422), a 183-bp designer intron-like loop (603-785), and a 300-bp antisense sequence (786-1085) complement to the first 300-bp coding sequence of a *Chlamydomonas reinhardtii* starch-synthase-mRNA sequence (GenBank: AF026422). This designer Starch-Synthase-iRNA sequence (303-1085) is designed to inhibit the synthesis of starch synthase by the following two mechanisms. First, the 300-bp antisense complement iRNA sequence (corresponding to DNA sequence 786-1085) binds with the normal mRNA of the starch synthase gene, thus blocking its translation into a functional starch synthase. Second, the 300-bp antisense complement iRNA sequence (corresponding to DNA sequence 786-1085) can also bind with the 300-bp sense counterpart (corresponding to DNA sequence 303-602) in the same designer iRNA molecule, forming a hairpin-like double-stranded RNA structure with the 183-bp designer intron-like sequence (603-785) as a loop. Experimental studies have shown that this type of hairpin-like double-stranded RNA can also trigger post-transcriptional gene silencing (Fuhrmann, Stahlberg, Govorunova, Rank and Hegemann (2001) *Journal of Cell Science* 114:3857-3863). Because of the use of a HydA1 promoter (21-302), this designer starch-synthesis-iRNA gene is designed to be expressed only under anaerobic conditions when needed to enhance photobiological ethanol production by channeling more photosynthetic products of the Calvin cycle into the ethanol-production pathway(s) as illustrated in FIGS. 4C and 4E.

Designer Starch-degradation and Glycolysis Genes

Figure 8A:
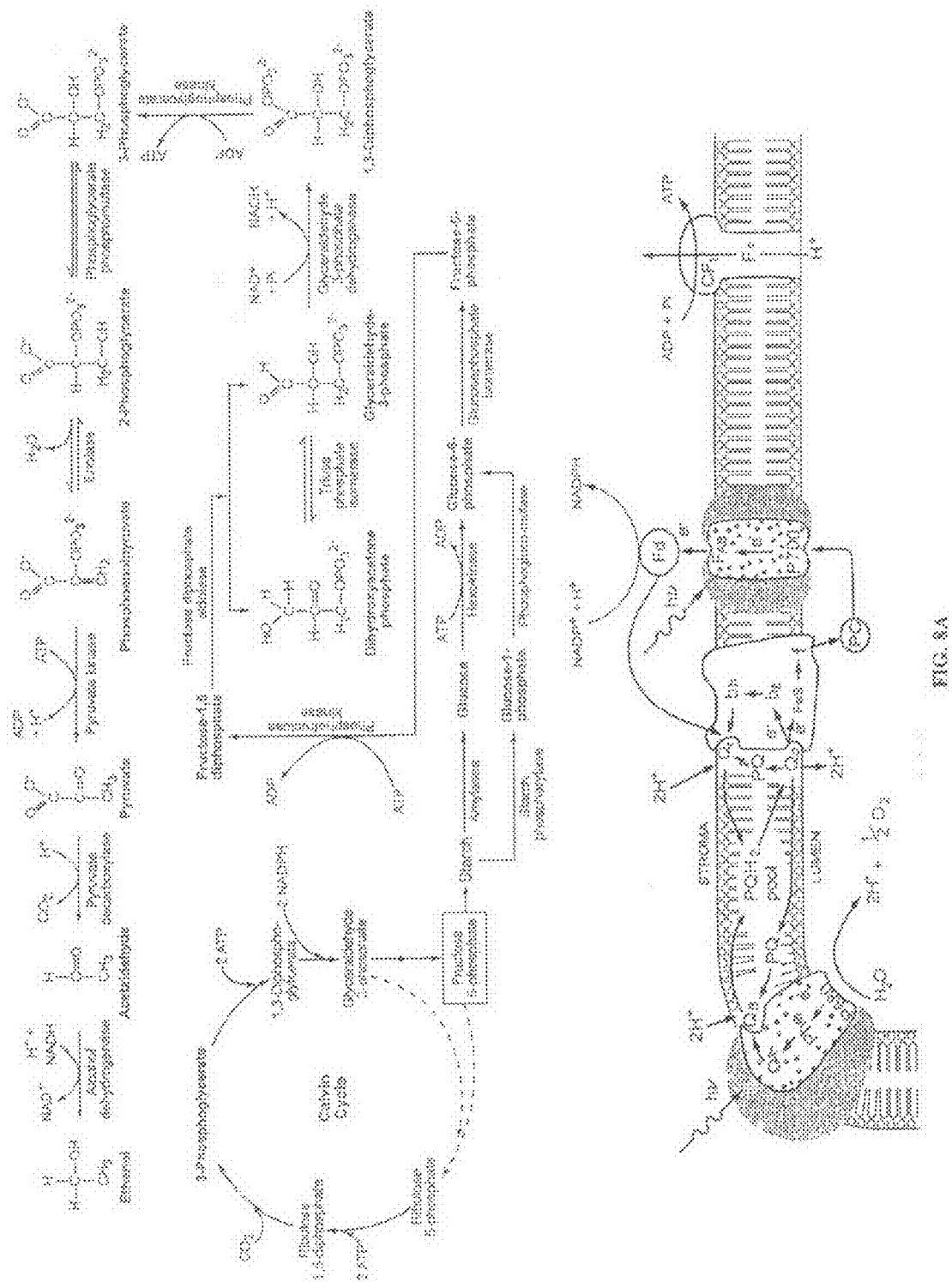
FIG. 8A illustrates an ethanol-production pathway (shown in blue) branched from the point of chloroplast starch to produce ethanol directly from $CO_2$ and $H_2O$ when the designer photosynthetic ethanol-producing pathway is expressed on under certain specific inducing conditions such as under anaerobic conditions.

In yet another embodiment of the present invention, the photobiological ethanol production is enhanced by incorporating an additional set of designer genes (FIG. 6G and FIG. 8A) that can facilitate starch degradation and glycolysis in combination with the designer ethanol-production gene(s) (FIG. 6A) in the chloroplast. Such additional designer genes for starch degradation include, for example, genes coding for amylase, starch phosphorylase, hexokinase, phosphoglucomutase, and glucose-phosphate-isomerase (G-P-isomerase). The designer glycolysis genes encode chloroplast-targeted glycolysis enzymes: glucosephosphate isomerase, phosphofructose kinase, aldolase, triose phosphate isomerase, glyceraldehyde-3-phosphate dehydrogenase, phosphoglycerate kinase, phosphoglycerate mutase, enolase, and pyruvate kinase. The designer starch-degradation and glycolysis genes in combination with any of the ethanol-production pathways shown in FIGS. 4B-4E can form additional pathway(s) from starch to ethanol. Consequently, co-expression of the designer starch-degradation and glycolysis genes with the ethanol-production-pathway genes can enhance photobiological production of ethanol as well. Therefore, this embodiment represents another approach to tame the Calvin cycle for enhanced photobiological production of ethanol. FIG. 8A presents a full designer starch-to-ethanol production pathway. In this case, some of the Calvin-cycle products flow through the starch synthesis pathway followed by the starch-to-ethanol pathway (FIG. 8A). In this case, starch acts as a transient storage pool of the Calvin-cycle products before they can be converted to ethanol. This mechanism can be quite useful in maximizing the ethanol-production yield in certain cases. For example, at high sunlight intensity such as around noon, the rate of Calvin-cycle photosynthetic $CO_2$ fixation can be so high that may exceed the maximal rate capacity of an ethanol-production pathway(s); use of the starch-synthesis mechanism allows temporary storage of the excess photosynthetic products to be used later for ethanol production as well.

Similar to the benefits of using the Calvin-cycle-branched designer ethanol-production pathways (FIGS. 4B-4E), the use of the designer starch-to-ethanol pathway (FIG. 8A) can also help to convert the photosynthetic products to ethanol before the sugars could be converted into other complicated biomolecules such as lignocellulosic biomasses which cannot be readily used by the biorefinery industries. Therefore, appropriate use of the Calvin-cycle-branched designer ethanol-production pathway(s) (FIGS. 4B-4E) and/or the designer starch-to-ethanol pathway (FIG. 8A) may represent revolutionary inter alia technologies that can effectively bypass the bottleneck problems of the current biomass technology including the "lignocellulosic recalcitrance" problem. FIG. 8B illustrates the use of a designer starch-to-ethanol pathway in combination with a Calvin-cycle-branched designer ethanol-production pathway for enhanced photobiological ethanol production.

Another feature is that a Calvin-cycle-branched designer ethanol-production pathway activity (FIGS. 4B-4E) can occur predominantly during the days when there is light because it uses an intermediate product of the Calvin cycle which requires supplies of reducing power (NADPH) and energy (ATP) generated by the photosynthetic water splitting and the light-driven proton-translocation-coupled electron transport process through the thylakoid membrane system. The designer starch-to-ethanol pathway (FIG. 8A) which can use the surplus sugar that has been stored as starch during photosynthesis, can operate not only during the days, but also at nights. Consequently, the use of a Calvin-cycle-branched designer ethanol-production pathway together with a designer starch-to-ethanol pathway as illustrated in FIG. 8B enables production of ethanol both during the days and at nights.

Because the expression for both the designer starch-to-ethanol pathway(s) and the Calvin-cycle-branched designer ethanol-production pathway(s) is controlled by the use of an inducible promoter such as an anaerobic hydrogenase promoter, this type of designer alga, plant or plant cells is also able to grow photoautotrophically under aerobic (normal) conditions. When the designer plant (e.g., designer alga) or plant cells are grown and ready for photobiological ethanol production, the cells are then placed under the specific inducing conditions such as under anaerobic conditions [or an ammonium-to-nitrate fertilizer use shift, if designer Nia1 promoter-controlled ethanol-production pathway(s) is used] for enhanced ethanol production, as shown in FIG. 8B.

Examples of designer starch-degradation genes are shown in SEQ ID NO: 18-22 listed. Briefly, SEQ ID NO:18 presents example 18 for a designer Amylase DNA construct that includes a PCR FD primer (sequence 1-20), a 2×84-bp NR promoter (21-188), a 9-bp Xho I NdeI site (189-197), a 135-bp RbcS2 transit peptide (198-332), an Amylase-encoding sequence (333-1616) selected and modified from a *Barley alpha-amylase* (GenBank: J04202A my46 expression tested in aleurone cells), a 21-bp Lumio-tag sequence (1617-1637), a 9-bp XbaI site (1638-1646), a 223-bp RbcS2 terminator (1647-1869), and a PCR RE primer (1870-1889).

SEQ ID NO: 19 presents example 19 for a designer Starch-Phosphorylase DNA construct that includes a PCR FD primer (sequence 1-20), a 2×84-bp NR promoter (21-188), a 135-bp RbcS2 transit peptide (189-323), a Starch Phosphorylase-encoding sequence (324-2846) selected and modified from a *Citrus* root starch-phosphorylase sequence (GenBank: AY098895, expression tested in *citrus* root), a 223-bp RbcS2 terminator (2847-3069), and a PCR RE primer (3070-3089).

SEQ ID NO: 20 presents example 20 for a designer Hexose-Kinase DNA construct that includes a PCR FD primer (sequence 1-20), a 2×84-bp NR promoter (21-188), a 135-bp RbcS2 transit peptide (189-323), a Hexose Kinase-encoding sequence (324-1706) selected and modified from *Ajellomyces capsulatus* hexokinase mRNA sequence (Genbank: XM_001541513), a 223-bp RbcS2 terminator (1707-1929), and a PCR RE primer (1930-1949).

SEQ ID NO: 21 presents example 21 for a designer Phosphoglucomutase DNA construct that includes a PCR FD primer (sequence 1-20), a 2×84-bp NR promoter (21-188), a 135-bp RbcS2 transit peptide (189-323), a Phosphoglucomutase-encoding sequence (324-2006) selected and modified from *Pichia stipitis* phosphoglucomutase sequence (GenBank: XM_001383281), a 223-bp RbcS2 terminator (2007-2229), and a PCR RE primer (22302249).

SEQ ID NO: 22 presents example 22 for a designer Glucosephosphate-Isomerase DNA construct that includes a PCR FD primer (sequence 1-20), a 2×84-bp NR promoter (21-188), a 135-bp RbcS2 transit peptide (189-323), a Glucosephosphate Isomerase-encoding sequence (324-1988) selected and modified from a *S. cerevisiae* phosphoglucoisomerase sequence (GenBank: M21696), a 223-bp RbcS2 terminator (1989-2211), and a PCR RE primer (2212-2231).

The designer starch-degradation genes such as those shown in SEQ ID NO: 18-22 can be selected for use in combination with various designer ethanol-production-pathway genes for construction of various designer starch-degradation ethanol-production pathways such as the pathways shown in FIGS. 8A and 8B. For example, the designer genes shown in SEQ ID NOS: 1-7 and 18-22 can be selected for construction of a Nia1 promoter-controlled starch-to-ethanol production pathway (FIG. 8A) that comprises of the following designer enzymes: amylase, starch phosphorylase, hexokinase, phosphoglucomutase, glucosephosphate isomerase, phosphofructose kinase, fructose diphosphate aldolase, triose phosphate isomerase, glyceraldehyde-3-phosphate dehydrogenase, phosphoglycerate kinase, phosphoglycerate mutase, enolase, pyruvate kinase, pyruvate decarboxylase, and alcohol dehydrogenase. This starch-to-ethanol pathway (FIG. 8A) may be used alone and/or in combinations with other ethanol-production pathway(s) such as the 3-phosphoglycerate-branched ethanol-production pathway as illustrated in FIG. 8B.

Figure 9:
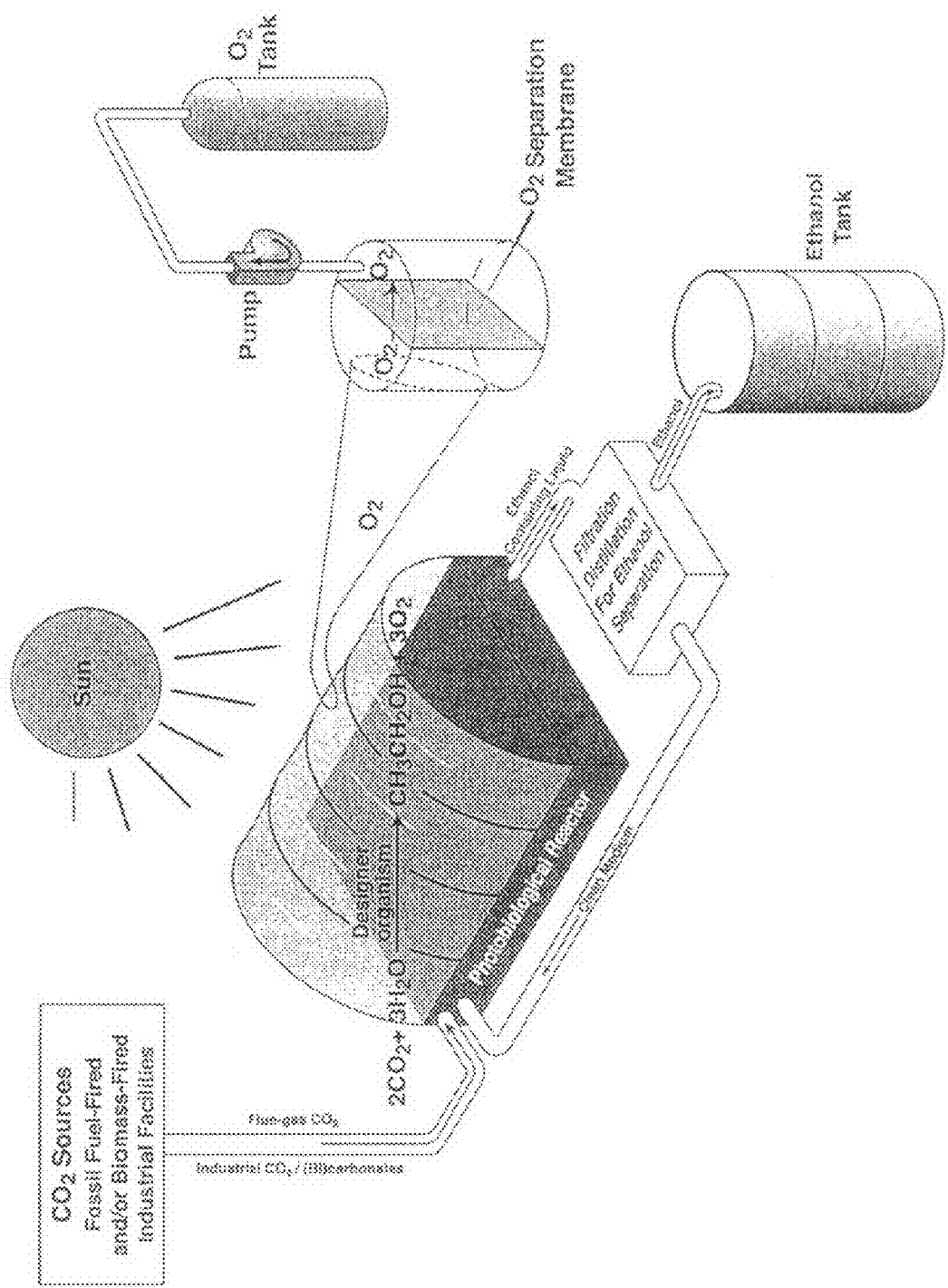
FIG. 9 illustrates an operational process how the use of a designer organism such as designer alga may be coupled with industrial $CO_2$ sources through a pipeline, a photobioreactor (sealed), and ethanol-oxygen-harvesting system for photosynthetic production of ethanol and $O_2$ directly from $CO_2$ and $H_2O$ using sunlight.
Figure 10:
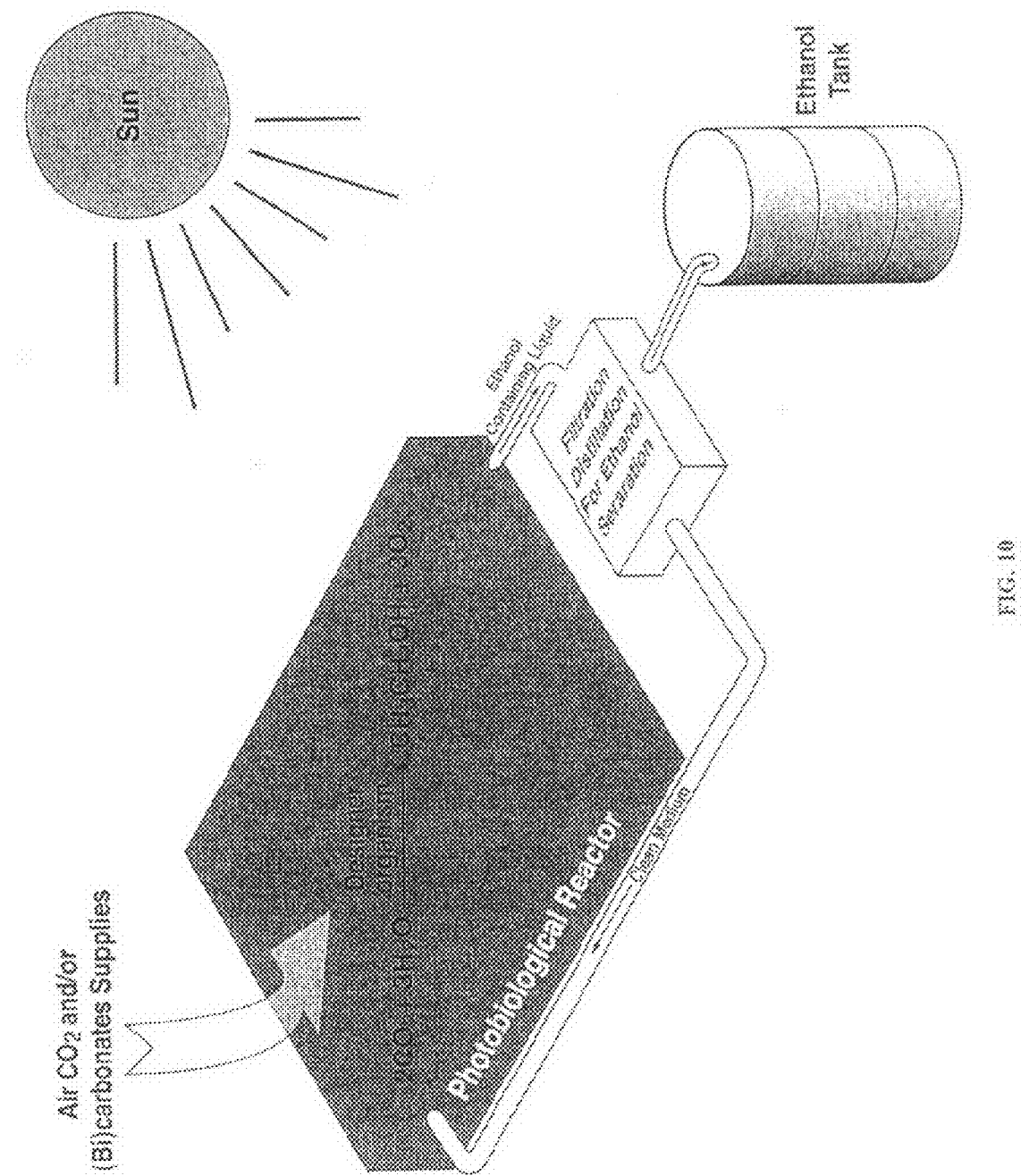
FIG. 10 illustrates an operational process how a designer organism such as designer alga may be used through a photobioreactor and ethanol-separation/harvesting system with supplies of air $CO_2$ and/or (bi)carbonates for photosynthetic production of ethanol and $O_2$ directly from $CO_2$ and $H_2O$ using sunlight.
Figure 11:
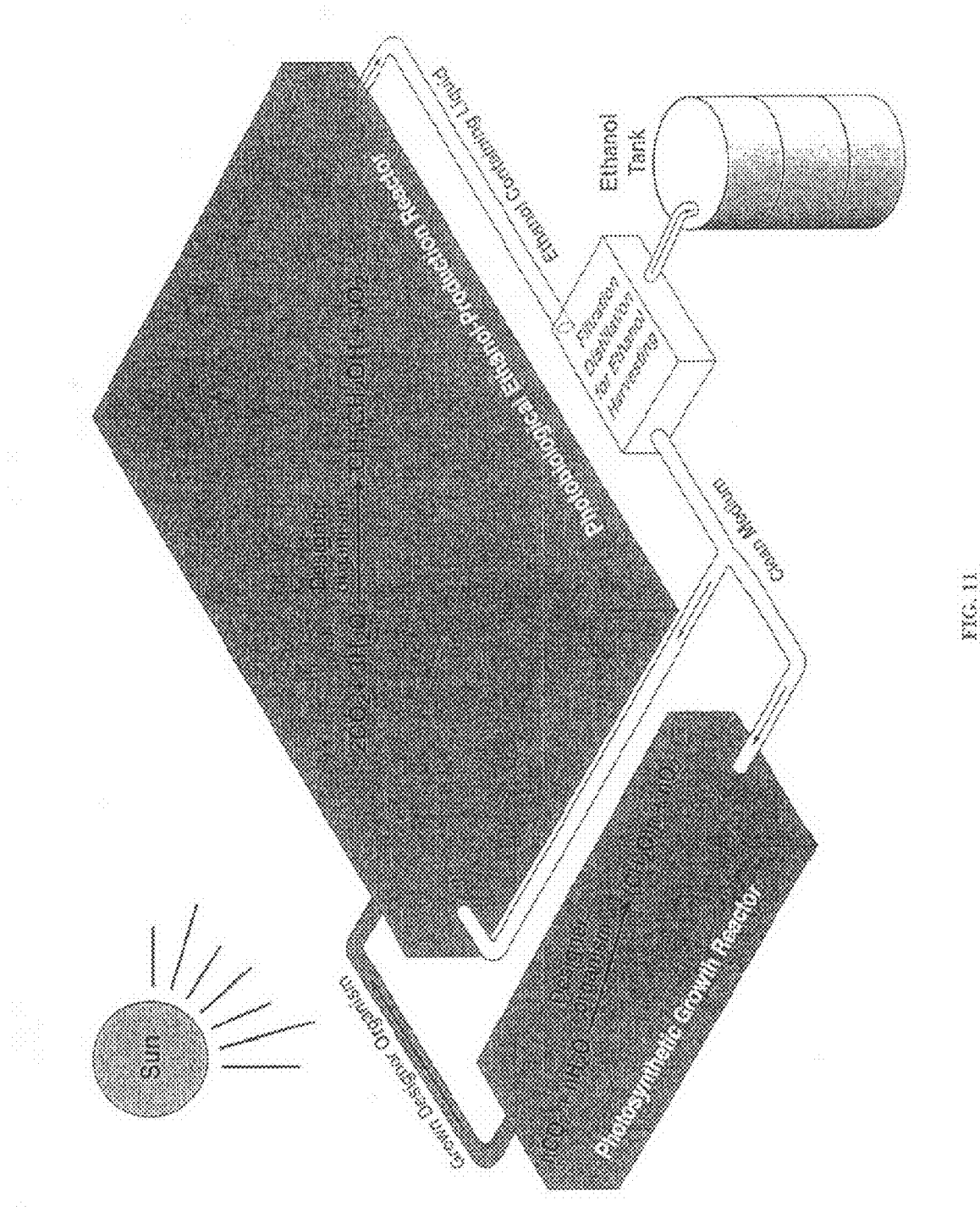
FIG. 11 illustrates an operational process how a designer organism such as designer alga may be used with a photosynthetic culture-growth reactor, a photobiological ethanol-production reactor, and an ethanol-harvesting system for photosynthetic production of ethanol and $O_2$ directly from $CO_2$ and $H_2O$ using sunlight.

Use of Photosynthetic Ethanol-Producing Designer Organisms with Photobioreactor -Ethanol-Harvesting (Distillation) Systems The various embodiments further teach how the designer organisms may be used with a photobioreactor and an ethanol-separation-harvesting system for photosynthetic production of ethanol ($CH_3CH_2OH$) and $O_2$ directly from $CO_2$ and $H_2O$ using sunlight (FIGS. 9-11). There are a number of embodiments on how the designer organisms may be used for photobiological ethanol production. One of the preferred embodiments is to use the designer organisms for direct photosynthetic ethanol production from $CO_2$ and $H_2O$ with a photobiological reactor and ethanol-harvesting (distillation) system (FIG. 9), which includes a specific operational process described as a series of the following steps: a) Growing a designer transgenic organism photoautotrophically in minimal culture medium using air $CO_2$ as the carbon source under aerobic (normal) conditions before inducing the expression of the designer ethanol-production-pathway genes; b) When the designer organism culture is grown and ready for ethanol production, sealing or placing the culture into a specific condition, such as an anaerobic condition that can be generated by removal of $O_2$ from the photobiological reactor, to induce the expression of designer ethanol-production genes; c) When the designer ethanol-production-pathway enzymes are expressed and inserted into the stroma region of the designer organism's chloroplast, supplying visible light energy such as sunlight for the designer-genes-expressed cells to work as the catalysts for photosynthetic ethanol production from $CO_2$ and $H_2O$; d) Harvesting the ethanol product by any method known to those skilled in the art. For example, harvesting the ethanol product from the photobiological reactor by a combination of membrane filtration and ethanol-distillation techniques and flexibly collecting the $O_2$ gas product from the reactor.

The above process to use the designer organisms for photosynthetic $CH_3CH_2OH$ and $O_2$ production from $CO_2$ and $H_2O$ with a biological reactor and ethanol-harvesting (distillation) and gas product separation and collection system can be repeated for a plurality of operational cycles to achieve more desirable results. Any of the steps a) through d) of this process described above can also be adjusted in accordance of the invention to suit for certain specific conditions. In practice, any of the steps a) through d) of the process can be applied in full or in part, and/or in any adjusted combination as well for enhanced photobiological ethanol production in accordance of this invention.

The sources of $CO_2$ that can be used in this process include, but not limited to, industrial $CO_2$, (bi)carbonates, and atmospheric $CO_2$. For an example, flue-gas $CO_2$ from fossil fuel-fired and/or biomass-fired industrial facilities can be fed through a pipeline into a photobiological reactor in this process as illustrated in FIG. 9. The industrial facilities that can generate $CO_2$ supplies for the designer photosynthetic ethanol-production process include (but not limited to): coal-fired power plants, iron and steelmaking industries, cement-manufacturing plants, petroleum refinery facilities, chemical fertilizer production factories, biomass-fired and/or fossil fuel-fired ethanol distillation/separation facilities, biomass-pyrolysis processes, smokestacks, fermentation bioreactors, biofuel-refinery facilities, and combinations thereof.

Alternatively, this designer photobiological ethanol-production process can also use the $CO_2$ in the environment and from the atmosphere (FIGS. 10 and 11) as well. Gaseous $CO_2$, dissolved $CO_2$, bicarbonate, and carbonates can all be used by the designer-organism photobiological ethanol production technology.

This embodiment is illustrated in more details here using designer algae as an example. As described above, designer algae of the present invention, such as the one that contains a set of designer HydA1 promoter-controlled designer ethanol-production-pathway genes (for examples, the DNA constructs of SEQ ID NO: 8-12), can grow normally under aerobic conditions by autotrophic photosynthesis using air $CO_2$ in a manner similar to that of a wild-type alga. The designer algae can grow also photoheterotrophically using an organic substrate as well.

In a preferred embodiment, a designer alga is grown photoautotrophically using air $CO_2$ as the carbon source under the aerobic conditions as shown in FIG. 4A in a minimal medium that contains the essential mineral (inorganic) nutrients. No organic substrate such as acetate is required to grow a designer alga under the normal conditions before the designer photosynthetic ethanol-production genes are expressed. Most of the algae can grow rapidly in water through autotrophic photosynthesis using air $CO_2$ as long as there are sufficient mineral nutrients. The nutrient elements that are commonly required for algal growth are: N, F, and K at the concentrations of about 1-10 mM, and Mg, Ca, S, and Cl at the concentrations of about 0.5 to 1.0 mM, plus some trace elements Mn, Fe, Cu, Zn, B, Co, Mo among others at μM concentration levels. All of the mineral nutrients can be supplied in an aqueous minimal medium that can be made with well-established recipes of algal culture media using water and relatively small of inexpensive fertilizers and mineral salts such as ammonium bicarbonate ($NH_4HCO_3$) (or ammonium nitrate, urea, ammonium chloride), potassium phosphates ($K_2HPO_4$ and $KH_2PO_4$), magnesium sulfate heptahydrate ($MgSO_4 \cdot 7H_2O$), calcium chloride ($CaCl_2$), zinc sulfate heptahydrate ($ZnSO_4 \cdot 7H_2O$), iron (II) sulfate heptahydrate ($FeSO_4 \cdot 7H_2O$), and boric acid ($H_3BO_3$), among others. That is, large amounts of designer algae cells can be inexpensively grown in a short period of time because, under aerobic conditions such as in an open pond, the designer algae can photoautotrophically grow by themselves using air $CO_2$ as rapidly as their wild-type parental strains. This is a significant feature (benefit) of the invention that could provide a cost-effective solution in generation of photoactive biocatalysts (the designer photosynthetic ethanol-producing algae) for renewable solar energy production.

When the algal culture is grown and ready for ethanol production, the grown algal culture is sealed or placed into certain specific conditions, such as anaerobic conditions that can be generated by removal of $O_2$ from the sealed photobiological reactor (FIG. 9), to induce the expression of designer photosynthetic ethanol-production-pathway genes. When the designer ethanol-production-pathway enzymes are expressed and inserted into the stroma region of algal chloroplast, visible light energy such as sunlight is supplied for the designer-genes-expressing algal cells to work as the catalysts for photosynthetic ethanol production from $CO_2$ and $H_2O$. When the designer genes are expressed, the algal cells can essentially become efficient and robust "green machines" that are perfect for photosynthetic production of ethanol ($CH_3CH_2OH$) and $O_2$ from $CO_2$ and $H_2O$. The ethanol product from the algal photobiological rector can be harvested by a combination of membrane filtration and ethanol-distillation techniques.

Photosynthetic production of $CH_3CH_2OH$ and $O_2$ directly from $CO_2$ and $H_2O$ in accordance with the present invention can, in principle, have high quantum yield. Theoretically, it requires only 24 photons to produce a $CH_3CH_2OH$ and $3O_2$ from water and carbon dioxide by this mechanism. The maximal theoretical sunlight-to-ethanol energy efficiency by the process of direct photosynthetic ethanol production from $CO_2$ and $H_2O$ is about 10%, which is the highest possible among all the biological approaches. Consequently, this approach has great potential when implemented properly with an algal reactor and ethanol-oxygen-harvesting system (FIG. 9).

The above process to use the designer algae for photosynthetic production of $CH_3CH_2OH$ and $O_2$ from $CO_2$ and $H_2O$ with an algal reactor and an ethanol-harvesting (distillation) and gas product separation and collection system (FIG. 9) can be repeated for a plurality of operational cycles to achieve more desirable results.

Another feature is that the designer switchable ethanol-production organism provides the capability for repeated cycles of photoautotrophic culture growth under normal aerobic conditions with a manner similar to that of a wild type (FIG. 1) and efficient photobiological production of ethanol (FIG. 2) when the designer ethanol-production pathway is switched on by an inducible promoter (such as hydrogenase promoter) at certain specific inducing conditions (such as under anaerobic conditions) in a bioreactor (FIG. 9). For example, the switchable designer alga with designer hydrogenase promoter-controlled ethanol-production genes contains normal mitochondria, which uses the reducing power (NADH) from organic reserves (and/or exogenous substrates, such as acetate) to power the cell immediately after its return to aerobic conditions. Therefore, when the algal cell is returned to aerobic conditions after its use under anaerobic conditions for production of ethanol, the cell will stop producing ethanol-production-pathway enzymes and start to restore its normal photoautotrophic capability by synthesizing normal functional chloroplast. Consequently, it is possible to use this type of genetically transformed organism for repeated cycles of photoautotrophic culture growth under normal aerobic conditions (FIG. 1) and efficient production of ethanol under anaerobic conditions (FIG. 2) in an anaerobic reactor (FIG. 9). That is, this photobiological ethanol-production technology can be operated for a plurality of operational cycles by rejuvenating the used culture under aerobic conditions and recyclably using the rejuvenated algal culture under ethanol-producing conditions to achieve more desirable results. Optionally, this photobiological ethanol-production technology is operated continuously by circulating rejuvenated algal culture from an aerobic reactor into the anaerobic reactor while circulating the used algal culture from the anaerobic reactor (after its use for ethanol production) into the aerobic reactor for rejuvenation by synthesizing normal functional chloroplasts through photosynthetic $CO_2$ fixation and photoautotrophic growth.

Some of the designer organisms could grow photoautotrophically even with the ethanol-production pathway(s) switched on. Whether or how fast a designer organism could grow under the ethanol-producing conditions may depend on its genetic background and how much of the Calvin cycle products are still available for cell growth after use by the designer ethanol-production pathway(s). Designer organisms that can, under the ethanol-producing conditions, maintain essential cellular functions with an appropriate growth rate can also be used for continuous photobiological production of $CH_3CH_2OH$ and $O_2$ from $CO_2$ and $H_2O$ with a bioreactor and an ethanol-harvesting (distillation) system (FIGS. 9 and 10).

There are additional ways that the switchable designer organisms can be used. For example, the used designer algal culture from a photobiological ethanol-production reactor does not have to be circulated back to a culture-growth reactor. Instead, the used algal culture is taken out to be used as fertilizers or biomass feed stocks for other processing because the photoautotrophic growth of the switchable designer alga in a culture-growth reactor (FIG. 11, left) is capable of continuously supplying algal cells to a photobiological ethanol-production reactor for the biofuel production (FIG. 11, right). This embodiment is, especially, helpful to using some of the designer organisms that can grow photoautotrophically only before but not after the ethanol-production-pathway(s) is switched on. For example, as illustrated in FIG. 11, by keeping a continuously growing culture of a designer alga (that can grow photoautotrophically only before the ethanol-production-pathway(s) is switched on) in a culture-growth reactor, it can provide continuous supplies of grown algal cells for use in a photobiological ethanol-production reactor. This approach makes it possible to use those designer organisms that can grow only before the ethanol-production-pathway(s) is switched on for photobiological ethanol production as well.

Because of various reasons, some of the designer ethanol-production organisms could grow only photohetrotrophically or photomixotrophically but not photoautotrophically. Use of a culture-growth reactor as illustrated in FIG. 11 can also grow this type of designer ethanol-production organisms photohetrotrophically or photomixotrophically using organic substrates including, but not limited to, sucrose, glucose, acetate, ethanol, methanol, propanol, butanol, acetone, starch, hemicellulose, cellulose, lipids, proteins, organic acids, biomass materials and combination thereof. The so-grown culture can also be supplied to a photobiological ethanol-production reactor for induction of the designer pathways for ethanol production as illustrated in FIG. 11. This modified embodiment on culture growth makes it possible to use those designer organisms that can grow only photohetrotrophically, or photomixotrophically also for photobiological ethanol production as well.

For certain specific designer organisms with designer nitrate reductase (Nia1) promoter-controlled ethanol-production-pathway genes, the above photobiological reactor process may be further adjusted to achieve more beneficial results. For example, a designer alga that contains Nia1 promoter-controlled ethanol-production-pathway genes such as the ones shown in DNA sequence design examples 1-7 (SEQ ID NO: 1-7), can grow normally in a culture medium with ammonium (but no nitrate) by autotrophic photosynthesis using air $CO_2$ in a manner similar to that of a wild-type alga. This is because the expression of the ethanol-production-pathway genes in this designer organism will be turned on only in the presence of nitrate as desired owning to the use of nitrate reductase (Nia1) promoter in controlling the designer pathway expression. A significant feature of the designer organisms with Nia1 promoter-controlled ethanol-production-pathway genes is that the expression of the designer ethanol-production pathways can be induced by manipulating the concentration levels of nitrate ($NO_3^-$) relative to that of ammonium ($NH_4^+$) in the culture medium without requiring any anaerobic conditions. That is, the expression of the designer ethanol-production pathway(s) can be induced under both aerobic and anaerobic conditions. This enables the designer photobiological ethanol-production process to operate even under aerobic conditions using atmospheric $CO_2$ (FIG. 10). Likewise, this type of designer organisms with Nia1 promoter-controlled ethanol-production-pathway genes can grow photoautotrophically both under aerobic and anaerobic conditions as well. Therefore, as a further embodiment, the operational process of using designer organism with nitrate reductase (Nia1) promoter-controlled ethanol-production-pathway genes is adjusted to the following: a) Growing a designer transgenic organism photoautotrophically in minimal culture medium in the presence of ammonium ($NH_4^+$) but no nitrate ($NO_3^-$) before inducing the expression of the designer ethanol-production-pathway genes; b) When the designer organism culture is grown and ready for ethanol production, adding nitrate ($NO_3^-$) fertilizer into the culture medium to raise the concentration of nitrate ($NO_3^-$) relative to that of ammonium ($NH_4^+$) to induce the expression of designer ethanol-production-pathway genes; c) When the designer ethanol-production-pathway enzymes are expressed and inserted into the stroma region of the designer organism's chloroplast, supplying visible light energy such as sunlight for the designer-genes-expressed cells to work as the catalysts for photosynthetic ethanol production from $CO_2$ and $H_2O$; d) Harvesting the ethanol product from the photobiological reactor by a combination of membrane filtration and ethanol-distillation techniques.

In addition to ethanol production, it is also possible to use a designer organism or part of its designer ethanol-production pathway(s) to produce certain intermediate products including: acetaldehyde, pyruvate, phosphoenolpyruvate, 2-phosphoglycerate, 1,3-diphosphoglycerate, glyceraldehye-3-phosphate, dihydroxyacetone phosphate, fructose-1,6-diphosphate, fructose-6-phosphate, glucose-6-phosphate, and glucose-1-phosphate. Therefore, a further embodiment comprises an additional step of harvesting the intermediate products that can be produced also from an induced transgenic designer organism. The production of an intermediate product can be selectively enhanced by switching off a designer-enzyme activity that catalyzes its consumption in the designer pathways. The production of a said intermediate product can be enhanced also by using a designer organism with one or some of designer enzymes omitted from the designer ethanol-production pathways. For example, a designer organism with the alcohol dehydrogenase or pyruvate decarboxylase omitted from the designer pathway of FIG. 4B may be used to produce acetaldehyde or pyruvate, respectively.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

DNA SEQUENCE LISTING

```
Sequence No. 1
Example 1: a designer Glyceraldehyde-3-Phosphate-Dehydrogenase
DNA construct (1677 bp)
    1 AGAAAATCTG GCACCACACC tatatggtag ggtgcgagtg accccgcgcg acttggagct 61 cgatggcccc gggttgtttg gggcgtccgc ctctcgcgct attctgagct ggagaccgag 121 gcgcatgaaa atgcattcgc ttccatagga cgctgcattg tggcttgaag gttcaaggga 181 agggttcaaa cgaccccgcc gtacgaactt ttgtcggggg gcgctcccgg cccgggctc 241 ttgtgcgcgc attagggctt cgggtcgcaa gcaagacgat acATGGCCGC CGTCATTGCC

301 AAGTCCTCCG TCTCCGCGGC CGTGGCTCGC CCGGCCCGCT CCAGCGTGCG CCCCATGGCC
```

```
 361 GCGCTGAAGC CCGCCGTCAA GGCTGCCCCC GTGGCTGCCC CGGCTCAGGC CAACCAGatg 421 gctcccatca agatcggcat caatggtttt ggtcgtattg ccgcctcgt gtggcgtgcc 481 actcttaacc gtgacgatgt cgaggtcgtc gccatcaatg atccattcat tgatgtgcca 541 tacatggtct acatggccaa gtatgactcg gtccacggca acctgaccca cgacgttcag 601 caaggcgacg gcaagctgat ggtcaatggc aagtcaatca ccatcttcgg caagatggat 661 gccaaggaga tcccatggaa ggaggccggc gcgaccttcg tcgttgagtc gactggtgtg 721 ttcaccaccc tggagggcgc cagctctcac ctggtcggcg gtgctgagac cgtcgtcatc 781 tccgccccat caaacgatgc cccatgttc gtcatgggtg tcaacgagga gggctacaag 841 ccagacatga agtggtgtc caacgcgtct tgcaccacca actgcctggg ccccctggcc 901 aaggtcatcc accttaagtt cggcatcctg gagggcctga tgaccaccgt ccacgcgacc 961 accgccaccc agaagaccgt cgacgggccg tccaagaagg actggcgcgg cgggcgcggc 1021 atcctggaca acatcatccc ctcggcgact ggtgccgcca aggccgtcgg caaggtgctg 1081 cctgccctga cggcaagct caccggcatg gccttccgcg tgcccacccc cgatgtctcg 1141 gtcgtcgatc tgaccgtgcg cctggagaag ggtgcgtcgt acgacgccat caaggccgag 1201 atcaagcgcg cgagcgagaa cgagctcaag ggcatcctgg cctacaccga ggatgccgtg 1261 gtctccaccg acttcatcgg caacaagcac agctccatct tcgacgccga ggccggcatc 1321 gccctcaacg acaactttgt caagctggtc tcctggtacg acaacgagtg gggctactcc 1381 aaccgtgtcg tcgacctgat cgcgcacatg gccaaggtca aggccgccag ccacTAAATG

1441 GAGGCGCTCG TTGATCTGAG CCTTGCCCCC TGACGAACGG CGGTGGATGG AAGATACTGC

1501 TCTCAAGTGC TGAAGCGGTA GCTTAGCTCC CCGTTTCGTG CTGATCAGTC TTTTTCAACA

1561 CGTAAAAAGC GGAGGAGTTT TGCAATTTTG TTGGTTGTAA CGATCCTCCG TTGATTTTGG

1621 CCTCTTTCTC CATGGGCGGG CTGGGCGTAT TTGAAGCggt tctctcttct gccgtta
//

Sequence No. 2
Example 2: a designer Phosphoglycerate-Kinase DNA construct (1908 bp)
   1 agaaaatctg gcaccacacc TATATGGTAG GGTGCGAGTG ACCCCGCGCG ACTTGGAGCT

61 CGATGGCCCC GGGTTGTTTG GGGCGTCCGC CTCTCGCGCT ATTCTGAGCT GGAGACCGAG

121 GCGCATGAAA ATGCATTCGC TTCCATAGGA CGCTGCATTG TGGCTTGAAG GTTCAAGGGA

181 AGGGTTCAAA CGACCCCGCC GTACGAACTT TTGTCGGGGG GCGCTCCCGG CCCCGGGCTC

241 TTGTGCGCGC ATTAGGGCTT CGGGTCGCAA GCAAGACGAT ACatggccct ctctatgaag 301 atgcgcgcca acgcgcgcgt gtccggtcgc cgcgtcgccg ctgtggcccc ccgcgtggtg 361 cccttctcgt cggcctccag ctccgtgctg cgctctggct tcgcgctgag gtgtctgtgg 421 acatccgccg cgtgggccgc tctcgcatcc gtcgtcgagg cggtgaagaa gtcggttggc 481 gacctgcaca aggctgacct ggagggcaag cgcgtgttcg tccgcgcgga cctgaacgtg 541 cctcttgaca aggccaccct ggccatcacc gacgacaccc gcattcgcgc ggccgtcccc 601 accctgaagt acctgctgga caacggtgct aaggtcctgc tgacctcgca cctgggtcgc 661 ccgaagggcg gtcccgagga caagtaccgc ctgacccccg tggtggcccg cctgtcggag 721 ctgctgggca agcccgtgac caaggtcgat gactgcatcg gcccgaggt ggagaaggcg 781 gtgggcgcca tgaagaacgg cgagctgctg ctgctggaga actgccgctt ctacaaggag 841 gaggagaaga acgagcccga gttcgccaag aagctggccg ccaacgccga cctgtacgtg
```

-continued

```
 901 aacgacgcgt tcggcactgc ccaccgcgcc cacgcctcca ccgagggtgt gaccaagttc
 961 ctgaagccct ccgtggccgg cttcctgctg cagaaggagc tggactacct tgatggcgcc
1021 gtgtccaacc ccaagcgccc cttcgtggcc attgtgggcg ctccaaggt gtcctccaag
1081 atcaccgtca ttgaggcgct gatggagaag tgcgacaaga tcatcatcgg cggtggcatg
1141 atcttcacct tctacaaggc ccgcgcgctg aaggtgggct cctcgctggt tgaggacgac
1201 aagatcgagc tggccaagaa gctggaggag atggccaagg ccaagggtgt gcagctgctg
1261 ctgcccaccg acgtggtggt ggccgacaag ttcgacgcca acgccaacac ccagaccgtg
1321 cccatcaccg ccatccccga tggctggatg ggtctggaca ttggcccgga ctccgtcaag
1381 accttcaacg acgccctggc cgacgccaag accgttgtgt ggaacggccc catgggtgtg
1441 ttcgagtttc cccaagttcg ccaacgcacc gtgtcgatcg ccaacaccct ggccggcctg
1501 acgcccaagg gctgcatcac catcattggt ggcggtgact ccgtggctgc cgtcgagcag
1561 gccggcgttg ccgagaagat gagccacatc tccaccggcg cggtgcctc cctggagctg
1621 ctggagggca aggtcctgcc cggcgtggcc gccctggacg agaagTAAAT GGAGGCGCTC
1681 GTTGATCTGA GCCTTGCCCC CTGACGAACG GCGGTGGATG GAAGATACTG CTCTCAAGTG
1741 CTGAAGCGGT AGCTTAGCTC CCCGTTTCGT GCTGATCAGT CTTTTTCAAC ACGTAAAAAG
1801 CGGAGGAGTT TTGCAATTTT GTTGGTTGTA ACGATCCTCC GTTGATTTTG GCCTCTTTCT
1861 CCATGGGCGG GCTGGGCGTA TTTGAAGCgg ttctctcttc tgccgtta
//

Sequence No. 3
Example 3: a designer Phosphoglycerate-Mutase DNA construct (2349 bp)
   1 agaaaatctg gcaccacacc TATATGGTAG GGTGCGAGTG ACCCCGCGCG ACTTGGAGCT
  61 CGATGGCCCC GGGTTGTTTG GGGCGTCCGC CTCTCGCGCT ATTCTGAGCT GGAGACCGAG
 121 GCGCATGAAA ATGCATTCGC TTCCATAGGA CGCTGCATTG TGGCTTGAAG GTTCAAGGGA
 181 AGGGTTCAAA CGACCCCGCC GTACGAACTT TTGTCGGGGG GCGCTCCCGG CCCCGGGCTC
 241 TTGTGCGCGC ATTAGGGCTT CGGGTCGCAA GCAAGACGAT ACctcgagca tATGGCCGCC
 301 GTCATTGCCA AGTCCTCCGT CTCCGCGGCC GTGGCTCGCC CGGCCCGCTC CAGCGTGCGC
 361 CCCATGGCCG CGCTGAAGCC CGCCGTCAAG GCTGCCCCG TGGCTGCCCC GGCTCAGGCC
 421 AACCAGatgg cgcacgacta caagctgaag gcccaccccg cgattcctgc gcccgagggc
 481 ccgctgctgg tctgcattct ggacggcttc ggcgagaacg agtacaagga tgagttcaac
 541 gccgtgcacg tggctaagac gcccactgtg gacgcgctgc gcgctgtgcc ccatcgcttc
 601 cgttccatca aggcgcacgg aaaggctgtg ggcctgccca gcgatgccga catgggcaac
 661 agcgaggtgg ggcacaacgc cctgggctcg gccaggtgg tggaccaagg cgcgcgcctg
 721 gtggacctgg cgctggagac cggccgtatg ttctcggacc ccggctggaa gctcatcagc
 781 gaggccttcc cctcccacac cgtccacttc atcggcctgc tgtccgacgg cggcgtgcac
 841 tcgcgcgccg atcagctgca cggctgcctg cgcggcgccg tggagcgcgg cgccaagcgc
 901 gtgcgcgtgc acatcctgac tgacggccgc gacgtgccgg acggcagcag catccggttc
 961 gtggaggagc tggaggcggt gctggcggag ctgcgcggca agggctgcga catcgccatc
1021 gcctcgggcg gcggccgcat gcaggtcacc atggaccgct acgaggcgga ctggagcatg
1081 gtgaagcgcg gctgggacgc gcacgtgctg ggcaaggcgc cccactactt caaggacgcc
1141 aagaccgcgg tcaccaccct gcgcggctcc gaggacgcgc cggtgtctga ccagtacgtg
```

-continued

```
1201 gcccccttgg tgattgtgga cgaggcggac aagccggtgg gcaccattga ggacggcgac 1261 gcggtggtgc tgttcaactt ccgcgcggac cgcatggtgg agatcagcaa ggccttcgag 1321 tacgaggacg gcttcaccgc ctttgagcgc gagcgcttcc ccaagggcct gcgcttcgtg 1381 ggcatgatgc agtacgacgg cgacctgaag ctgcccgcca acttcctggt gccgccgccc 1441 ctgattgagc acgtgtcggg cgagtacctg tgcaagaacg ggctgagcac cttcgcctgc 1501 tccgagactc agaagttcgg gcacgtgacg ttcttctgga cggcaaccg ctccggctac 1561 ctggacgcca agcaggagca gtacctggag atcccgtcgg acaagatcga gttcaacaag 1621 gctccggaca tgaaggcgcg cgagatcacc gccgccggca ttgaggcgct caagagcggc 1681 aagtacaagg tggtgcgcat caactacgcc aacccggaca tggtcggcca caccggcgac 1741 atggctgcca ccgtccgcgc tgcgagacc gtggacgggt cgtgaagga gctgctggag 1801 gtggtggaca gcctgaacgg ccgctggatc gtcacgtccg accacggcaa cgccgacgac 1861 atggtgcagc gcgacaagaa gggcaagccc ctgctgggcg aggacggcaa gccgctgccc 1921 ctgaccagcc acacgctggc gcccgtgccg ttcttcatcg gcggcaaggg cctgccggac 1981 ggcgtggtgc tgcgcgacga cctgccggac gccgggctgg ccaacgtggc cgccaccacc 2041 ttcaacctgc tgggcttcga ggcgcccggc atctacaagc ccagcatggt caaggcgTAA 2101 TCTAGAtaaa tggaggcgct cgttgatctg agccttgccc cctgacgaac ggcggtggat 2161 ggaagatact gctctcaagt gctgaagcgg tagcttagct ccccgtttcg tgctgatcag 2221 tcttttcaa cacgtaaaaa gcggaggagt tttgcaattt tgttggttgt aacgatcctc 2281 cgttgatttt ggcctctttc tccatgggcg ggctgggcgt atttgaagcG GTTCTCTCTT

2341 CTGCCGTTA
//
```

Sequence No. 4
Example 4: a designer Enolase DNA construct (1815 bp) that includes
a PCR FD primer

```
   1 agaaaatctg gcaccacacc TATATGGTAG GGTGCGAGTG ACCCCGCGCG ACTTGGAGCT

61 CGATGGCCCC GGGTTGTTTG GGGCGTCCGC CTCTCGCGCT ATTCTGAGCT GGAGACCGAG

121 GCGCATGAAA ATGCATTCGC TTCCATAGGA CGCTGCATTG TGGCTTGAAG GTTCAAGGGA

181 AGGGTTCAAA CGACCCCGCC GTACGAACTT TTGTCGGGGG GCGCTCCCGG CCCCGGGCTC

241 TTGTGCGCGC ATTAGGGCTT CGGGTCGCAA GCAAGACGAT ACctcgagca tATGGCCGCC

301 GTCATTGCCA AGTCCTCCGT CTCCGCGGCC GTGGCTCGCC CGGCCCGCTC CAGCGTGCGC

361 CCCATGGCCG CGCTGAAGCC CGCCGTCAAG CTGCCCCCG TGGCTGCCCC GGCTCAGGCC

421 AACCAGgtga ccaaggctgt tgagaacatc aacgctatta ttgccccgc cctgaagggc 481 atggaccccg tcaagcaggc ggagattgac cagaagatga aggacctgga cggcactgac 541 aacaagggca agctgggtgc caacgccatc ctggccgtct ccatggccgt gtgcaaggcc 601 ggtgccgctg agaagggcgt gcccctgtac aagcacattg cggacctggc cggcaacagc 661 aagctgatcc tgcccgtgcc ctcgttcaac atcatcaacg cggcagcca cgccggcaac 721 gccctggcta tgcaggagtt catgatcctg cccgttggcg cctcgagctt ctctgaggcc 781 atgcgcatgg gctgcgaggt gtaccacgcc ctgaagggcc tgatcaaggc caagtacggc 841 caggacgcct gcaacgtggg tgatgagggt ggcttcgccc caacatcgg ctccaacgat 901 gagggcctga acttggtgaa cgaggccatc gagaaggccg gctacaccgg caaggtgaag 961 atcggcatgg acgtggcctc gtcggagttc tacaccgagg acggcatgta cgacctggac
```

-continued

```
1021 ttcaagaacc agcccaacga tggctcgcag aagaagacca aggagcagat gctggagctg 1081 tacaacgagt tctgcaagaa gtacccggtc atctccatcg aggacccctt cgagcaggac 1141 gactgggagc cctgcgccaa gctgaccacc gagaacatct gccaggtggt cggcgacgac 1201 atcctggtga ccaacccccgt gcgcgtgaag aaggccatcg acgccaaggc cgtcaacgct 1261 ctgctgctca aggtcaacca gatcggtacc attaccgagt ccattgaggc cgtgcgcatg 1321 gccaaggagg ccggctgggg tgtcatgacc agccaccgct cgggtgagac tgaggactct 1381 ttcatcgccg acctggcggt gggcctggcc tccggccaga tcaagaccgg cgcccctgc 1441 cgctcggagc gcaatgccaa gtacaaccag ctgctgcgca tcgaggagga gctgggcgag 1501 aacgctgtgt acgctggcga gagctggcgc cacatcggct ggGGCTGCTG CCCCGGCTGC 1561 TGCtaatcta gaTAAATGGA GGCGCTCGTT GATCTGAGCC TTGCCCCCTG ACGAACGGCG

1621 GTGGATGGAA GATACTGCTC TCAAGTGCTG AAGCGGTAGC TTAGCTCCCC GTTTCGTGCT

1681 GATCAGTCTT TTTCAACACG TAAAAAGCGG AGGAGTTTTG CAATTTTGTT GGTTGTAACG

1741 ATCCTCCGTT GATTTTGGCC TCTTTCTCCA TGGGCGGGCT GGGCGTATTT GAAGCggttc 1801 tctcttctgc cgtta
//

Sequence No. 5
Example 5: a designer Pyruvate-Kinase DNA construct (2021 bp)
   1 agaaaatctg gcaccacacc ATGGTAGGGT GCGAGTGACC CCGCGCGACT TGGAAGGGTT 61 CAAACGACCC CGCCGTACGA ACTTTTGTCG GGGGGCGCTC CCGGctcgag catATGGCCG

121 CCGTCATTGC CAAGTCCTCC GTCTCCGCGG CCGTGGCTCG CCCGGCCCGC TCCAGCGTGC

181 GCCCCATGGC CGCGCTGAAG CCCGCCGTCA AGGCTGCCCC CGTGGCTGCC CCGGCTCAGG

241 CCAACCAGat gtctagatta gaaagattga cctcattaaa cgttgttgct ggttctgact 301 tgagaagaac ctccatcatt ggtaccatcg gtccaaagac caacaaccca gaaaccttgg 361 ttgctttgag aaaggctggt ttgaacattg tccgtatgaa cttctctcac ggttcttacg 421 aataccacaa gtctgtcatt gacaacgcca gaaagtccga agaattgtac ccaggtagac 481 cattggccat tgctttggac accaagggtc cagaaatcag aactggtacc accaccaacg 541 atgttgacta cccaatccca ccaaaccacg aaatgatctt caccaccgat gacaagtacg 601 ctaaggcttg tgacgacaag atcatgtacg ttgactacaa gaacatcacc aaggtcatct 661 ccgctggtag aatcatctac gttgatgatg gtgttttgtc tttccaagtt ttggaagtcg 721 ttgacgacaa gactttgaag gtcaaggctt tgaacgccgg taagatctgt tcccacaagg 781 gtgtcaactt accaggtacc gatgtcgatt tgccagcttt gtctgaaaag acaaggaag 841 atttgagatt cggtgtcaag aacggtgtcc acatggtctt cgcttctttc atcagaaccg 901 ccaacgatgt tttgaccatc agagaagtct ggggtgaaca aggtaaggac gtcaagatca 961 ttgtcaagat tgaaaaccaa caaggtgtta caacttcga cgaaatcttg aaggtcactg 1021 acggtgttat ggttgccaga ggtgacttgg gtattgaaat cccagcccca gaagtcttgg 1081 ctgtccaaaa gaaattgatt gctaagtcta acttggctgg taagccagtt atctgtgcta 1141 cccaaatgtt ggaatccatg acttacaacc caagaccaac cagagctgaa gtttccgatg 1201 tcggtaacgc tatcttggat ggtgctgact gtgttatgtt gtctggtgaa accgccaagg 1261 gtaactaccc aatcaacgcc gttaccacta tggctgaaac cgctgtcatt gctgaacaag 1321 ctatcgctta cttgccaaac tacgatgaca tgagaaactg tactccaaag ccaacctcca
```

-continued

```
1381 ccaccgaaac cgtcgctgcc tccgctgtcg ctgctgtttt cgaacaaaag gccaaggcta 1441 tcattgtctt gtccacttcc ggtaccaccc caagattggt ttccaagtac agaccaaact 1501 gtccaatcat cttggttacc agatgcccaa gagctgctag attctctcac ttgtacagag 1561 gtgtcttccc attcgttttc gaaaaggaac ctgtctctga ctggactgat gatgttgaag 1621 cccgtatcaa cttcggtatt gaaaaggcta aggaattcgg tatcttgaag aagggtgaca 1681 cttacgtttc catccaaggt ttcaaggccg gtgctggtca ctccaacact ttgcaagtct 1741 ctaccgttGG CTGCTGCCCC GGCTGCTGCt aatctagaTA AATGGAGGCG CTCGTTGATC

1801 TGAGCCTTGC CCCCTGACGA ACGGCGGTGG ATGGAAGATA CTGCTCTCAA GTGCTGAAGC

1861 GGTAGCTTAG CTCCCCGTTT CGTGCTGATC AGTCTTTTTC AACACGTAAA AAGCGGAGGA

1921 GTTTTGCAAT TTTGTTGGTT GTAACGATCC TCCGTTGATT TTGGCCTCTT TCTCCATGGG

1981 CGGGCTGGGC GTATTTGAAG Cggttctctc ttctgccgtt a
//

Sequence No. 6
Example 6: a designer Pyruvate-Decarboxylase DNA construct (2231 bp)
    1 agaaaatctg gcaccacacc ATGGTAGGGT GCGAGTGACC CCGCGCGACT TGGAAGGGTT 61 CAAACGACCC CGCCGTACGA ACTTTTGTCG GGGGGCGCTC CCGGctcgag catATGGCCG

121 CCGTCATTGC CAAGTCCTCC GTCTCCGCGG CCGTGGCTCG CCCGGCCCGC TCCAGCGTGC

181 GCCCCATGGC CGCGCTGAAG CCCGCCGTCA AGGCTGCCCC CGTGGCTGCC CCGGCTCAGG

241 CCAACCAGat ggtatcaacc tacccagaat cagaggttac tctaggaagg tacctctttg 301 agcgactcca ccaattgaaa gtggacacca ttttcggctt gccgggtgac ttcaaccttt 361 ccttattgga caaagtgtat gaagttccgg atatgaggtg ggctggaaat gccaacgaat 421 tgaatgctgc ctatgctgcc gatggttact ccagaataaa gggattgtct tgcttggtca 481 caacttttgg tgttggtgaa ttgtctgctt taaacggagt tggtggtgcc tatgctgaac 541 acgtaggact tctacatgtc gttggagttc atccatatc gtcacaggct aaacagttgt 601 tgctccacca taccttgggt aatggtgact tcactgtttt tcacagaatg tccaatagca 661 tttctcaaac tacagcattt ctctcagata tctctattgc accaggtcaa atagatagat 721 gcatcagaga agcatatgtt catcagagac cagtttatgt tggtttaccg gcaaatatgg 781 ttgatctcaa ggttccttct agtctcttag aaactccaat tgatttgaaa ttgaaacaaa 841 atgatcctga agctcaggaa gaagttgttg aaacagtcct gaagttggtg tcccaagcta 901 caaacccccat tatcttggta gacgcttgtg ccctcagaca caattgcaaa gaggaagtca 961 aacaattggt tgatgccact aattttcaag tctttacaac tccaatgggt aaatctggta 1021 tctccgaatc tcatccaaga tttggcggtg tctatgtcgg acaatgtcg agtcctcaag 1081 tcaaaaaagc cgttgaaaat gccgatctta ctatctgt ggttcgttg ttatcggact 1141 tcaatacagg ttcattttca tactcctaca agacgaagaa tgttgttgaa ttccactctg 1201 actatatgaa aatcagacag gccaccttcc caggagttca atgaaagaa gccttgcaac 1261 agttgataaa aagggtctct tcttacatca atccaagcta cattcctact cgagttccta 1321 aaaggaaaca gccattgaaa gctccatcag aagctccttt gacccaagaa tatttgtggt 1381 ctaaagtatc cggctggttt agagagggtg atattatcgt aaccgaaact ggtacatctg 1441 cttttcggaat tattcaatcc cattttccca gcaacactat cggtatatcc caagtcttgt 1501 ggggctcaat tggtttcaca gtaggtgcaa cagttggtgc tgccatggca gcccaggaaa
```

-continued

```
1561 tcgaccctag caggagagta attttgttcg tcggtgatgg ttcattgcag ttgacggttc 1621 aggaaatctc tacgttgtgt aaatgggatt gtaacaatac ttatctttac gtgttgaaca 1681 atgatggtta cactatagaa aggttgatcc acggcaaaag tgccagctac aacgatatac 1741 agccttggaa ccatttatcc ttgcttcgct tattcaatgc taagaaatac caaaatgtca 1801 gagtatcgac tgctggagaa ttggactctt tgttctctga taagaaattt gcttctccag 1861 ataggataag aatgattgag gtgatgttat cgagattgga tgcaccagca aatcttgttg 1921 ctcaagcaaa gttgtctgaa cgggtaaacc ttgaaaatGG CTGCTGCCCC GGCTGCTGCt 1981 aatctagaTA AATGGAGGCG CTCGTTGATC TGAGCCTTGC CCCCTGACGA ACGGCGGTGG

2041 ATGGAAGATA CTGCTCTCAA GTGCTGAAGC GGTAGCTTAG CTCCCCGTTT CGTGCTGATC

2101 AGTCTTTTTC AACACGTAAA AAGCGGAGGA GTTTTGCAAT TTTGTTGGTT GTAACGATCC

2161 TCCGTTGATT TTGGCCTCTT TCTCCATGGG CGGGCTGGGC GTATTTGAAG Cggttctctc 2221 ttctgccgtt a
//

Sequence No. 7
Example 7: a designer Alcohol-Dehydrogenase DNA construct (1649 bp)
     1 agaaaatctg gcaccacacc ATGGTAGGGT GCGAGTGACC CCGCGCGACT TGGAAGGGTT

61 CAAACGACCC CGCCGTACGA ACTTTTGTCG GGGGGCGCTC CCGGATGGTA GGGTGCGAGT

121 GACCCCGCGC GACTTGGAAG GGTTCAAACG ACCCCGCCGT ACGAACTTTT GTCGGGGGGC

181 GCTCCCGGct cgagcatATG GCCGCCGTCA TTGCCAAGTC CTCCGTCTCC GCGGCCGTGG

241 CTCGCCCGGC CCGCTCCAGC GTGCGCCCCA TGGCCGCGCT GAAGCCCGCC GTCAAGGCTG

301 CCCCCGTGGC TGCCCCGGCT CAGGCCAACC AGatgtctat cccaaaaact caaaaaggtg 361 ttatcttcta cgaatcccac ggtaagttgg aatacaaaga tattccagtc ccaaccccaa 421 aggccaacga attgttgatc aacgtcaagt actccggtgt ctgtcacact gacttgcacg 481 cttggcacgg tgactggcct ttgccagtca agctaccatt agttggtggt cacgaaggtg 541 ccggtgtcgt tgtcgccatg ggtgaaaacg tcaagggctg gaacatcggt gactacgccg 601 gtattaagtg gttgaacggt tcttgtatgg cctgtgaata ctgtgaattg ggtaacgaat 661 ccaactgtcc tcacgctgac ttgtctggtt acacccacga cggttctttc aacaatacg 721 ctaccgctga ctccgtccaa gccgctcaca ttccaaaggg tactgacttg gctgaatgtg 781 ctccagtctt gtgtgctggt atcactgtct acaaggcttt gaagtccgct aacttgtctg 841 ccggccaatg ggttgccatt tccggtgctg ctggtggtct aggttctttg gctgtccaat 901 acgccaaggc catgggttac agagtcgtcg gtattgacgg tggtgaaggt aaggaagaat 961 tattcagatc cattggtggt gaagttttca tcgatttcac tactgaaaag gacattgtcg 1021 gtgccgtcat caaggccact gacggtggtg ctcacggtat cattaacgtt tccgtttccg 1081 aagccgccat cgaagcttct accagatact gtagagctaa cggtaccact gttttggtcg 1141 gtatgccagc cggtgctaag tgttgttctg atgtcttcaa ccaagtcgtc aagtccatct 1201 ccattgtcgg ttcttacgtc ggtaacagag ctgacaccag agaagctttg gacttcttcg 1261 ccagaggttt ggtcaagtct ccaatcaagg ttgtcggttt gtctaccttg ccagaaattt 1321 acgaaaagat ggaaaagggt caaatcgtcg gtagatacgt tgttgacact tctaaaGGCT 1381 GCTGCCCCGG CTGCTGCtaa tctagaTAAA TGGAGGCGCT CGTTGATCTG AGCCTTGCCC

1441 CCTGACGAAC GGCGGTGGAT GGAAGATACT GCTCTCAAGT GCTGAAGCGG TAGCTTAGCT
```

```
1501 CCCCGTTTCG TGCTGATCAG TCTTTTTCAA CACGTAAAAA GCGGAGGAGT TTTGCAATTT

1561 TGTTGGTTGT AACGATCCTC CGTTGATTTT GGCCTCTTTC TCCATGGGCG GGCTGGGCGT

1621 ATTTGAAGCg gttctctctt ctgccgtta
//

Sequence No. 8
Example 8: a designer HydA1-promoter-linked Phosphoglycerate-Mutase
DNA construct (2351 bp)
   1 AGAAAATCTG GCACCACACC gagctgtcat gcgttgttcc gttatgtgtc gtcaaacgcc 61 ttcgagcgct gcccggaaca atgcgtacta gtataggagc catgaggcaa gtgaacagaa 121 gcgggctgac tggtcaaggc gcacgatagg gctgacgagc gtgctgacgg ggtgtaccgc 181 cgagtgtccg ctgcattccc gccggattgg gaaatcgcga tggtcgcgca taggcaagct 241 cgcaaatgct gtcagcttat cttacatgaa cacacaaaca ctctcgcagg cactagcctc 301 aaATGGCCGC CGTCATTGCC AAGTCCTCCG TCTCCGCGGC CGTGGCTCGC CCGGCCCGCT

361 CCAGCGTGCG CCCCATGGCC GCGCTGAAGC CCGCCGTCAA GGCTGCCCCC GTGGCTGCCC

421 CGGCTCAGGC CAACCAGatg gcgcacgact acaagctgaa ggcccacccg gcgattcctg 481 cgcccgaggg cccgctgctg gtctgcattc tggacggctt cggcgagaac gagtacaagg 541 atgagttcaa cgccgtgcac gtggctaaga cgcccactgt ggacgcgctg cgcgctgtgc 601 cccatcgctt ccgttccatc aaggcgcacg aaaggctgt gggcctgccc agcgatgccg 661 acatgggcaa cagcgaggtg gggcacaacg ccctgggctc gggccaggtg gtggaccaag 721 gcgcgcgcct ggtggacctg gcgctggaga ccggccgtat gttctcggac cccggctgga 781 agctcatcag cgaggccttc ccctcccaca ccgtccactt catcggcctg ctgtccgacg 841 gcggcgtgca ctcgcgcgcc gatcagctgc acggctgcct gcgcggcgcc gtggagcgcg 901 gcgccaagcg cgtgcgcgtg cacatcctga ctgacggccg cgacgtgccg gacggcagca 961 gcatccggtt cgtggaggag ctggaggcgg tgctggcgga gctgcgcggc aagggctgcg 1021 acatcgccat cgcctcgggc ggcggccgca tgcaggtcac catggaccgc tacgaggcgg 1081 actggagcat ggtgaagcgc ggctgggacg cgcacgtgct gggcaaggcg ccccactact 1141 tcaaggacgc caagaccgcg gtcaccaccc tgcgcggctc cgaggacgcg ccggtgtctg 1201 accagtacgt ggccccettt gtgattgtgg acgaggcgga caagccggtg gcaccattg 1261 aggacggcga cgcggtggtg ctgttcaact tccgcgcgga ccgcatggtg gagatcagca 1321 aggccttcga gtacgaggac ggcttcaccg cctttgagcg cgagcgcttc cccaagggcc 1381 tgcgcttcgt gggcatgatg cagtacgacg gcgacctgaa gctgcccgcc aacttcctgg 1441 tgccgccgcc cctgattgag cacgtgtcgg gcgagtacct gtgcaagaac gggctgagca 1501 ccttcgcctg ctccgagact cagaagttcg gcacgtgac gttcttctgg aacggcaacc 1561 gctccggcta cctggacgcc aagcaggagc agtacctgga gatcccgtcg acaagatcg 1621 agttcaacaa ggctccggac atgaaggcgc gcgagatcac cgccgccggc attgaggcgc 1681 tcaagagcgg caagtacaag gtggtgcgca tcaactacgc caacccggac atggtcggcc 1741 acaccggcga catggctgcc accgtccgcg cctgcgagac cgtggacggg tgcgtgaagg 1801 agctgctgga ggtggtggac agcctgaacg gccgctggat cgtcacgtcc gaccacggca 1861 acgccgacga catggtgcag cgcgacaaga agggcaagcc cctgctgggc gaggacggca 1921 agccgctgcc cctgaccagc cacacgctgg cgcccgtgcc gttcttcatc ggcggcaagg 1981 gcctgccgga cggcgtggtg ctgcgcgacg acctgccgga cgccgggctg gccaacgtgg
```

```
2041 ccgccaccac cttcaacctg ctgggcttcg aggcgcccgg catctacaag cccagcatgg 2101 tcaaggcgTA AATGGAGGCG CTCGTTGATC TGAGCCTTGC CCCCTGACGA ACGGCGGTGG

2161 ATGGAAGATA CTGCTCTCAA GTGCTGAAGC GGTAGCTTAG CTCCCCGTTT CGTGCTGATC

2221 AGTCTTTTTC AACACGTAAA AAGCGGAGGA GTTTTGCAAT TTTGTTGGTT GTAACGATCC

2281 TCCGTTGATT TTGGCCTCTT TCTCCATGGG CGGGCTGGGC GTATTTGAAG Cggttctctc 2341 ttctgccgtt a
//

Sequence No. 9
Example 9: a designer HydA1-promoter-linked Enolase DNA construct (1796
bp)
   1 AGAAAATCTG GCACCACACC gagctgtcat gcgttgttcc gttatgtgtc gtcaaacgcc 61 ttcgagcgct gcccggaaca atgcgtacta gtataggagc catgaggcaa gtgaacagaa 121 gcgggctgac tggtcaaggc gcacgatagg gctgacgagc gtgctgacgg ggtgtaccgc 181 cgagtgtccg ctgcattccc gccggattgg gaaatcgcga tggtcgcgca taggcaagct 241 cgcaaatgct gtcagcttat cttacatgaa cacacaaaca ctctcgcagg cactagcctc 301 aaATGGCCGC CGTCATTGCC AAGTCCTCCG TCTCCGCGGC CGTGGCTCGC CCGGCCCGCT

361 CCAGCGTGCG CCCCATGGCC GCGCTGAAGC CGCCGTCAA GGCTGCCCCC GTGGCTGCCC

421 CGGCTCAGGC CAACCAGgtg accaaggctg ttgagaacat caacgctatt attgccccg 481 ccctgaaggg catggacccc gtcaagcagg cggagattga ccagaagatg aaggacctgg 541 acggcactga caacaagggc aagctgggtg ccaacgccat cctggccgtc tccatggccg 601 tgtgcaaggc cggtgccgct gagaagggcg tgccctgta caagcacatt gcggacctgg 661 ccggcaacag caagctgatc ctgcccgtgc cctcgttcaa catcatcaac ggcggcagcc 721 acgccggcaa cgccctggct atgcaggagt tcatgatcct gccgttggc gcctcgagct 781 tctctgaggc catgcgcatg ggctgcgagg tgtaccacgc cctgaagggc ctgatcaagg 841 ccaagtacgg ccaggacgcc tgcaacgtgg gtgatgaggg tggcttcgcc cccaacatcg 901 gctccaacga tgagggcctg aacttggtga acgaggccat cgagaaggcc ggctacaccg 961 gcaaggtgaa gatcggcatg gacgtggcct cgtcggagtt ctacaccgag gacggcatgt 1021 acgacctgga cttcaagaac cagcccaacg atggctcgca gaagaagacc aaggagcaga 1081 tgctggagct gtacaacgag ttctgcaaga gtacccggt catctccatc gaggacccct 1141 tcgagcagga cgactgggag ccctgcgcca agctgaccac cgagaacatc tgccaggtgg 1201 tcggcgacga catcctggtg accaaccccg tgcgcgtgaa gaaggccatc gacgccaagg 1261 ccgtcaacgc tctgctgctc aaggtcaacc agatcggtac cattaccgag tccattgagg 1321 ccgtgcgcat ggccaaggag gccggctggg gtgtcatgac cagccaccgc tcgggtgaga 1381 ctgaggactc tttcatcgcc gacctggcgg tgggcctggc ctccggccag atcaagaccg 1441 gcgcccctg ccgctcggag cgcaatgcca agtacaacca gctgctgcgc atcgaggagg 1501 agctgggcga gaacgctgtg tacgctggcg agagctggcg ccacatcggc tggTAAATGG

1561 AGGCGCTCGT TGATCTGAGC CTTGCCCCCT GACGAACGGC GGTGGATGGA AGATACTGCT

1621 CTCAAGTGCT GAAGCGGTAG CTTAGCTCCC CGTTTCGTGC TGATCAGTCT TTTTCAACAC

1681 GTAAAAAGCG GAGGAGTTTT GCAATTTTGT TGGTTGTAAC GATCCTCCGT TGATTTTGGC
```

```
1741 CTCTTTCTCC ATGGGCGGGC TGGGCGTATT TGAAGCggtt ctctcttctg ccgtta
//
```

Sequence No. 10
Example 10: a designer HydA1-promoter-linked Pyruvate-Kinase DNA
construct (1832 bp)

```
   1 AGAAAATCTG GCACCACACC gagctgtcat gcgttgttcc gttatgtgtc gtcaaacgcc
  61 ttcgagcgct gcccggaaca atgcgtacta gtataggagc catgaggcaa gtgaacagaa
 121 gcgggctgac tggtcaaggc gcacgatagg gctgacgagc gtgctgacgg ggtgtaccgc
 181 cgagtgtccg ctgcattccc gccggattgg gaaatcgcga tggtcgcgca taggcaagct
 241 cgcaaatgct gtcagcttat cttacatgaa cacacaaaca ctctcgcagg cactagcctc
 301 aaATGGCCGC CGTCATTGCC AAGTCCTCCG TCTCCGCGGC CGTGGCTCGC CCGGCCCGCT
 361 CCAGCGTGCG CCCCATGGCC GCGCTGAAGC CGCCGTCAA GGCTGCCCCC GTGGCTGCCC
 421 CGGCTCAGGC CAACCAGatg tgcgagatgc tggacgcggg cgtggtgggc tgccgcgtgg
 481 acctgacgtg gggcccgctg gagttccacc gcaagtcgct tgccaatctg cagcaggcca
 541 tgcgcaagag ccgccgcctg tgttgcacca tggtggacac gctgggccgc gagctcatga
 601 tccgccgcca gagagggca ggctggaccc agcgccagag gggtggggtg atcatcacca
 661 cgcgcacgga cgtggacgcc agcagcaacg tgctgcccat cacttacagc aagttcacgg
 721 agatggcggt caagggcgac accatctaca tcggccgcta cctggtgtgc ggcgcagaca
 781 gcgcctcgct gtacctggag gtcatggacg tgcagggcga cgacgtgtac tgcatcgcca
 841 agaacgacgc ggtgctggac ggcctgctga cggtgttcca cgcggagcgc tccgtggagg
 901 ggctggccaa cgtgcagaac gacctgccgc tgctgtccga ctacgacaag gagtgcctgc
 961 acatcctggc gcaggacttc gagcgcgcgc cctacatctc caagctggag tccatcgcct
1021 cctccgccgt gcgcgccgcc gaccgcgtgg gcgccagcct gattgtggtg tacacgcaca
1081 ccggcaagac ggcgcagctg gtggccaagt accggccgcc catgcccatc ctgacgctgg
1141 tggtgccgca cctggtgtct gaccagctca gtggaagct ggagggcagg tccagcgcgc
1201 gccagtgcct catcagtcgc gcgctgctgc cggtgctggc cgcgccctcg cccagcggcg
1261 accagctgct gcaggaggcg gtggccatgg cgggccgcgt caagctggtc aagccgcacg
1321 accacgtggt gtgcgtgcag cgcatccacg acgacttctg cgtcaagatc atctccgtgg
1381 acgacatggg cgcgggcatc aagcgcgacg acacggtcat gtcgcacagc gtgtttggca
1441 gcagccccat ggccgtgcag ggctcgtccg gctacgactc gccgcgcgtg cacaacaacc
1501 ccatcggcaa caagttcggc cccatgccgc ccgccatcat caccaccggc aatagcttca
1561 ccctgggcgg catgggcgtg ggcgtgctgT AAATGGAGGC GCTCGTTGAT CTGAGCCTTG
1621 CCCCCTGACG AACGGCGGTG GATGGAAGAT ACTGCTCTCA AGTGCTGAAG CGGTAGCTTA
1681 GCTCCCCGTT TCGTGCTGAT CAGTCTTTTT CAACACGTAA AAGCGGAGG AGTTTTGCAA
1741 TTTTGTTGGT TGTAACGATC CTCCGTTGAT TTTGGCCTCT TTCTCCATGG GCGGGCTGGG
1801 CGTATTTGAA GCggttctct cttctgccgt ta
//
```

Sequence No. 11
Example 11: a designer HydA1-promoter-linked Pyruvate-Decarboxylase
DNA construct (2390 bp)

```
   1 AGAAAATCTG GCACCACACC gagctgtcat gcgttgttcc gttatgtgtc gtcaaacgcc
  61 ttcgagcgct gcccggaaca atgcgtacta gtataggagc catgaggcaa gtgaacagaa
```

-continued

```
 121 gcgggctgac tggtcaaggc gcacgatagg gctgacgagc gtgctgacgg ggtgtaccgc 181 cgagtgtccg ctgcattccc gccggattgg gaaatcgcga tggtcgcgca taggcaagct 241 cgcaaatgct gtcagcttat cttacatgaa cacacaaaca ctctcgcagg cactagcctc 301 aaATGGCCGC CGTCATTGCC AAGTCCTCCG TCTCCGCGGC CGTGGCTCGC CCGGCCCGCT

361 CCAGCGTGCG CCCCATGGCC GCGCTGAAGC CGCCGTCAA GGCTGCCCCC GTGGCTGCCC

421 CGGCTCAGGC CAACCAGatg ccaccaccg tgtcgcccgc agacgccaac ctcggcctgc 481 acattgccaa ccggcttgtt gagatcggct gcaccagctg cttcgcggtg cccggcgact 541 tcaacctgct gctgctggac cagctgctca agcagcccga gctgtccctg gtgtggtgct 601 gcaacgagct gaatgcgggc tacgcggcgg acggctacgc ccgcaagcgc ggcgtgggct 661 gcctgtgcgt gaccttctgt gtgggaggct ctccgccct gaacgctgtg ggcggtgcct 721 acagtgagga cctgccgctc atcgtcatca gcgggggcc caactcgcag gaccacgcct 781 ccaaccgcat cctgcaccac accacgggcg ccaacgagta cggccagcag ctgcgcgcct 841 tcagggaggt gacctgctgc caggtggtca tccagcacat cgaggacgcg cacatgctgc 901 tggatacggc catcagtgag gcgatgctga agcgcaagcc cgtgtacatc gaggtggcat 961 gtgagtgtgt cgtgacttgg tacttgttag ggggcgggt gatgggggg ccgtcgctct 1021 gggccgcggt ggaggcggcg gtggagtggc tgggcggtgg cgtgaagccg ctgctgctgg 1081 cgggcgtgcg cacgcgcccg cccgccgcgc gcaaggcgat gctggccctg gcggaggcca 1141 gccgctaccc cgtggccgtg atgccggacg ccaagggcat gttccccgag gaccacgagc 1201 agtacatcgg catgtactgg ggcccggtgt ccacgccgtg tgtgtgcgag gtggtggaga 1261 gcagcgacat cgtgctgtgc gtgggaggag tgtggacgga ctactccact gccggctact 1321 cgctgctgct caagcccgag aagatgctgc gcgtggacaa caaccgcgtc acattgggca 1381 acggaccgac gtttggctgc atcgtgatga ccgacttcct ggaggccctg gccaagcggg 1441 tggcgcccaa cgacaccggc cacgtcatct acaagcgcat ggctctgccg ccctcggagc 1501 cgccgccgca ggccgagggc gaactgctgc gcaccaacgt gctgttcaaa cacatccagc 1561 acatgctgac tccctccacc agcctcatca gcgaggtggg cgactcctgg ttcaacacac 1621 tcaagctcaa gctgcccgcc ggctgcgagt acgagctgca gatgcgctac ggctccattg 1681 gctggagtgt gggcgcggtg ctgggctacg gcgtggcgga cggcagacg gcgcccgacc 1741 gccgcgtggt ggcgtgcatc ggcgacggct ccttccagat gaccgcacag gaggtgagca 1801 ccatgctgcg ctacggcctg gaccccatca tcttcctcat caacaacggc ggctacacca 1861 tcgaggtgga gatccacgac ggcccctaca acgtgatcaa gaactgggac taccccggta 1921 tggtgcgcgc gctgcacaac ggccagggca agctgtggac cgccgaggcc cgcaccgagc 1981 ccgagctgca ggccgccgtg gccgaggctg tgcagcgcg cggcgagctg tgcttcatca 2041 tggtggtgac tcaccgtgac gactgcagca aggagctgct ggagtggggc agccgcgtgg 2101 cggcggccaa cagccgcaag ccgcccacca ccggctacgg cggccacTAA ATGGAGGCGC

2161 TCGTTGATCT GAGCCTTGCC CCCTGACGAA CGGCGGTGGA TGGAAGATAC TGCTCTCAAG

2221 TGCTGAAGCG GTAGCTTAGC TCCCCGTTTC GTGCTGATCA GTCTTTTTCA ACACGTAAAA

2281 AGCGGAGGAG TTTTGCAATT TGTTGGTTG TAACGATCCT CCGTTGATTT TGGCCTCTTT

2341 CTCCATGGGC GGGCTGGGCG TATTTGAAGC ggttctctct tctgccgtta
//
```

Sequence No. 12
Example 12: a designer HydA1-promoter-linked Alcohol-Dehydrogenase
DNA construct (3341 bp)

```
   1 AGAAAATCTG GCACCACACC gagctgtcat gcgttgttcc gttatgtgtc gtcaaacgcc 61 ttcgagcgct gcccggaaca atgcgtacta gtataggagc catgaggcaa gtgaacagaa 121 gcgggctgac tggtcaaggc gcacgatagg gctgacgagc gtgctgacgg ggtgtaccgc 181 cgagtgtccg ctgcattccc gccggattgg gaaatcgcga tggtcgcgca taggcaagct 241 cgcaaatgct gtcagcttat cttacatgaa cacacaaaca ctctcgcagg cactagcctc 301 aaATGGCCGC CGTCATTGCC AAGTCCTCCG TCTCCGCGGC CGTGGCTCGC CCGGCCCGCT

361 CCAGCGTGCG CCCCATGGCC GCGCTGAAGC CGCCGTCAA GGCTGCCCCC GTGGCTGCCC

421 CGGCTCAGGC CAACCAGcat gctgaggtga agaaggagcg cgccccagcc accgatgagg 481 cgctgacgga gctgaaggcg ctgctgaagc gcgcccagac cgcccaggcg cagtactcca 541 cctacaccca ggagcaggtg gacgagatct ccgcgccgc cgccgaggcc gccaacgccg 601 cccgtatccc cctggccaag atggccgtgg aggagacccg catgggcgtg gctgaggaca 661 aggtggtgaa gaaccacttc gcctccgagt tcatctacaa caagtacaag cacactaaga 721 cctgcggcgt catcgagcac gaccccgccg gcggcatcca gaaggtggct gagcccgtgg 781 gcgtcattgc cggtatcgtg cccaccacca accccacctc caccgccatc ttcaagtcgc 841 tgctgtcgct caagacccgc aacgcgctgg tgctgtgccc gcaccccgc gccgccaaga 901 gcgccatcgc cgccgcgcgc atcgtgcgtg acgccgccgt ggccgccggc gcgccgccca 961 acatcatcag ctgggtggag acgccctcgc tgccggtgtc ccaggcgctg atgcaggcga 1021 ctgagatcaa cctcatcctg gccaccggtg gcccggccat ggtgcgcgcc gcctactcgt 1081 ccggcaaccc gtcgctgggt gtgggcgccg caacaccccc ggccctgatt gacgagactg 1141 ccgacgtggc catggccgtg tcctccatcc tgctgtccaa gacctttgac aacggcgtca 1201 tctgcgcctc ggagcagtcg gtggtggtgg tggccaaggc ctacgacgcc gtgcgcaccg 1261 agttcgtgcg ccgcggggcc tacttcctga ccgaggacga caaggtcaag gtccgcgccg 1321 gtgtggttgt ggacggcaag ctgaacccca acattgtggg ccagtccatc cccaagctgg 1381 cggccctgtt cggcatcaag gtgccccagg cacaacggt gctcatcggc gaggtggaga 1441 agatcggccc cgaggaggcg ctgtcgcagg agaagctgtg ccccatcctg gccatgtacc 1501 gggcgcccga ctacgaccac ggcgtcaaga tggcctgcga gctcatcatg tacggcggcg 1561 ccggccacac ctcggtgctg tacaccaacc cgctcaacaa cgcccacatc cagcagtacc 1621 agagcgcggt caagaccgtg cgcatcctca tcaacacccc cgcctcgcag ggcgccattg 1681 gtgacctgta caacttccac ctggaccct ccctcaccct gggctgcggc acctggggct 1741 ccacctcggt gtccaccaac gtgggcccgc agcacctgct gaacatcaag accgtcaccg 1801 cgcgccgcga gaacatgctg tggttccgcg tgccgcccaa gatctacttc aagggcggct 1861 gcctggaggt ggcgctgacc gatctgcgtg gcaaatcgcg cgctttcatt gtcacggaca 1921 agccgctttt tgacatggga tacgccgaca aggtcaccca catcctggac agcattaacg 1981 tgcaccacca ggtgttctac cacgtgaccc ccgacccgac cctggcctgc attgaggcgg 2041 gtctgaagga gatcctggag ttcaagcccg atgtcatcat cgcgctgggt ggtggctcgc 2101 ccatggacgc cgccaagatc atgtggctga tgtacgagtg ccccgacacc cgcttcgacg 2161 gcctggccat gcgcttcatg gacatccgca gcgcgtgta cgaggtgccg gagctgggca 2221 agaaggccac catggtgtgc atccccacca ccagtggcac cggtcggag gtgacgccct 2281 ctcggtggt caccgacgag cgcctgggcg ccaagtaccc cctggccgat tacgccctga
```

-continued

```
2341 cccccagcat ggccattgtg gacccccagc tggtgctcaa catgcccaag aagctgaccg 2401 cctggggcgg cattgacgcg ctcacgcacg cgctggagag ctacgtgtcc atctgcgcca 2461 ccgactacac caagggtctg tcgcgcgagg ccatcagcct gctgttcaag tacctgcccc 2521 gcgcctacgc caacggctcc aacgactacc tggcgcgtga aaggtgcac tacgccgcca 2581 cgattgccgg catggccttc gccaacgcct tcctgggcat ctgccactcc atggcgcaca 2641 agctgggcgc cgcctaccac gtgcctcacg gcctggccaa cgccgcgctg atcagccacg 2701 tcatccgcta caacgccacc gacatgcccg ccaagcaggc cgccttcccg cagtacgagt 2761 accccaccgc caagcaggac tacgccgacc tggccaacat gctgggcctg gcggcaaca 2821 cggtggacga aaggtgatc aagctgattg aggcggtgga ggagctcaag gccaaggtgg 2881 acatcccgcc caccatcaag gagatcttca cgaccccaa ggtggacgcc gacttcctgg 2941 cgaacgtgga cgccctggcc gaggacgcct tcgacgacca gtgcacgggc gccaacccgc 3001 gctacccgct catggccgac ctgaagcagc tctacctgga cgcccacgcc gcgcccatcc 3061 tgcccgtcaa gaccctggag ttcttctcca agatcaacTA AATGGAGGCG CTCGTTGATC

3121 TGAGCCTTGC CCCCTGACGA ACGGCGGTGG ATGGAAGATA CTGCTCTCAA GTGCTGAAGC

3181 GGTAGCTTAG CTCCCCGTTT CGTGCTGATC AGTCTTTTTC AACACGTAAA AAGCGGAGGA

3241 GTTTTGCAAT TTTGTTGGTT GTAACGATCC TCCGTTGATT TTGGCCTCTT TCTCCATGGG

3301 CGGGCTGGGC GTATTTGAAG Cggttctctc ttctgccgtt a
//

Sequence No. 13
Example 13: a designer Fructose-Diphosphate-Aldolase DNA construct (1556
bp)
   1 agaaaatctg gcaccacacc ATGGTAGGGT GCGAGTGACC CCGCGCGACT TGGAAGGGTT

61 CAAACGACCC CGCCGTACGA ACTTTTGTCG GGGGCGCTC CCGGATGGTA GGGTGCGAGT

121 GACCCCGCGC GACTTGGAAG GGTTCAAACG ACCCCGCCGT ACGAACTTTT GTCGGGGGGC

181 GCTCCCGGat ggccctgatg atgaagtcgt cggccagcct gaaggctgtg tcgctggccg 241 ctctcgccgc gccgtcgttg tgcgcgccgg gcaagtacga tgaggagctg attaagaccg 301 ctggcaccgt tgcctccaag ggccgcggta tcctggccat ggacgagtca aacgccacct 361 gcggcaaacg cctggactcc atcggcgtgg agaacaccga ggagaaccgc cgcgcctacc 421 gcgagctgct ggtgaccgcc cccggcctgg ccagtacat ctccggcgct atcctgttcg 481 aggagaccct gtatcagtcc accgcctccg gcaagaagtt cgtcgatgtg atgaaggagc 541 agaacatcgt gcccggcatc aaggtcgaca agggcctggt gccctgtcca acaccaacga 601 tgagctggtg catgggcctg gacggctgga caagcgctgc tgagtactac aaggccggcg 661 ctcgcttcgc caagtggcgc tcggtcgtct cgatccccca cggcccctcg atcatgctgc 721 cgcgactggc ctacggcctg gcccgctacg ccgccatcgc cagaacgcc ggtctggtgc 781 ccattgtgga gcccgaggtc ctgctggacg gtgagcacga catcgaccgc tgcctggagg 841 tgcaggaggc catctgggcc gagaccttca gtacatggc cgacaacaag gtcatgttgc 901 agggtatcct gctgaagccc gccatggtca ccccggcgc tgactgcaag aacaaggccg 961 gccccgccaa ggttgccgag tacaccctga agatgctggc cgcgcgtgcc ccccggtcc 1021 ccggcatcat gttcctgtcg ggcggccagt ccgagctgga gtcgaccctg aacctgaacg 1081 ccatgaacca gagccccaac ccgtggcacg tgtcgttctc gtacgcccgc gctctgacga 1141 acaccgttct gaagacctgg caggcaagcc cgagaacggt ccaggcgccc aggctcgctg
```

-continued

```
1201 ctcaagcgcg caaggccaac tcggacgctc agcagggcaa gtacgacgcc accaccgagg 1261 gcaaggaggc tgcccagggc atgtacgaga agggaaaagg ctacgtctac taaTAAATGG

1321 AGGCGCTCGT TGATCTGAGC CTTGCCCCCT GACGAACGGC GGTGGATGGA AGATACTGCT

1381 CTCAAGTGCT GAAGCGGTAG CTTAGCTCCC CGTTTCGTGC TGATCAGTCT TTTTCAACAC

1441 GTAAAAAGCG GAGGAGTTTT GCAATTTTGT TGGTTGTAAC GATCCTCCGT TGATTTTGGC

1501 CTCTTTCTCC ATGGGCGGGC TGGGCGTATT TGAAGCggtt ctctcttctg ccgtta
//

Sequence No. 14
Example 14: a designer Triose-Phosphate-Isomerase DNA construct (1379
bp)
    1 agaaaatctg gcaccacacc ATGGTAGGGT GCGAGTGACC CCGCGCGACT TGGAAGGGTT

61 CAAACGACCC CGCCGTACGA ACTTTTGTCG GGGGCGCTC CCGGATGGTA GGGTGCGAGT

121 GACCCCGCGC GACTTGGAAG GGTTCAAACG ACCCCGCCGT ACGAACTTTT GTCGGGGGGC

181 GCTCCCGGat ggcagctacc tctctcactg cccctccttc tttctccggt ctccgccgca 241 tttctcccaa gctcgacgct gccgccgtct cctcccacca atccttcttc caccgcgtca 301 attcctctac ccgtctcgtt tcttcctctt cttcttctca tcgctccccc agaggtgttg 361 ttgccatggc tggatccgga aagttttcg ttggaggaaa ctggaagtgt aacgggacta 421 aggactccat cgccaagctt atctccgatc tcaacagtgc aaccttggaa gcagatgtag 481 atgttgttgt gtcacctcca tttgtctaca tcgaccaggt caaatcctcg ttgacagacc 541 gtattgacat atcaggtcag aactcttggg ttgggaaagg tggagccttc actggtgaaa 601 tcagcgtgga acagctcaaa gaccttggct gcaagtgggt cattcttggg cattccgaac 661 ggagacatgt catcggagaa aaagatgagt ttatcgggaa gaaagctgca tatgcattga 721 gtgagggtct tggagtgata gcttgtattg gggaaaagct agaagagagg gaagcaggca 781 agacgtttga tgtttgcttc gcgcaactga aggcgtttgc tgatgctgtg cctagctggg 841 acaatatagt tgttgcatac gagcctgtat gggcaattgg aactggtaaa gttgcatctc 901 ctcagcaagc acaagaagtc catgtagctg tccgcggttg gctaaagaag aatgtctctg 961 aggaagttgc ttccaaaacg agaatcatat atggaggttc tgtcaatgga ggcaacagtg 1021 cagagcttgc caaagaagaa gacattgatg gatttcttgt tggtggtgcc tccttgaagg 1081 gtcctgagtt tgcaaccatt gtgaactcag tcacgtcgaa gaaagttgct gcttgaTAAA

1141 TGGAGGCGCT CGTTGATCTG AGCCTTGCCC CCTGACGAAC GGCGGTGGAT GGAAGATACT

1201 GCTCTCAAGT GCTGAAGCGG TAGCTTAGCT CCCCGTTTCG TGCTGATCAG TCTTTTTCAA

1261 CACGTAAAAA GCGGAGGAGT TTTGCAATTT TGTTGGTTGT AACGATCCTC CGTTGATTTT

1321 GGCCTCTTTC TCCATGGGCG GCTGGGCGT ATTTGAAGCg ttctctcttc tgccgtta
//

Sequence No. 15
Example 15: a designer Phosphofructose-Kinase DNA construct (2156 bp)
    1 AGAAAATCTG GCACCACACC atggtagggt gcgagtgacc ccgcgcgact tggaagggtt 61 caaacgaccc cgccgtacga acttttgtcg ggggcgctc ccggatggta gggtgcgagt 121 gaccccgcgc gacttggaag ggttcaaacg accccgccgt acgaactttt gtcggggggc 181 gctcccggAT GGCCGCCGTC ATTGCCAAGT CCTCCGTCTC CGCGGCCGTG GCTCGCCCGG

241 CCCGCTCCAG CGTGCGCCCC ATGGCCGCGC TGAAGCCCGC CGTCAAGGCT GCCCCCGTGG

301 CTGCCCCGGC TCAGGCCAAC CAGatggaag cttcgatttc gtttctgggg tcaacaaaac
```

```
 361 ccaatatttc cttgtttaac ccttcttcaa acgtccttcc tcgtagagat ttccctcttc 421 ctgctttgaa attgaagaaa gtttcagtgc tgcctcgaat cttgcaccag aaacgactca 481 tcagagctca gtgctctgat ggattcaaac cagaggaaga cgatgggttt gtcctagaag 541 acgttcctca cttgaccaaa tttctccctg atttaccgtc atatccaaat ccattgaaag 601 aaagccaagc atatgccatt gttaagcgaa cttttgtcag ttccgaagat gtggttgcgc 661 aaaatattgt agtccagaag ggaagtaagc gaggagtaca ctttaggcga gcagggcctc 721 gagaaagagt gtacttcaga tcagatgaag taaaagcttg catagtgact tgtggggct 781 tgtgcccggg aatcaatact gttatacggg aaattgtatg tggattgaac aatatgtatg 841 gtgttaataa cattctcggc attcagggag gatatagagg cttttactcc aaaaacacta 901 tgaacctgac acctaaagta gttaacgata ttcataaacg cggtggcact tttcttcaaa 961 cctcaagagg aggacatgat acagcgaaga ttgttgataa tattcaagat agaggaataa 1021 atcaggtata tattattgga ggtggtggga cgcaaaaggg tgcagagaag atatacgagg 1081 aagttgagag gcgtggtctt caagtggcgg tttctggcat tcctaagaca attgataatg 1141 atattgctgt gattgacaaa tcatttggct ttgatacggc ggttgaggaa gcacaacgag 1201 ctattaatgc tgcacatgta gaggtcgaga gcgtggaaaa tggagttggt atcgttaaac 1261 tcatgggcag atacagtggg tttattgcca tgattgcaac tttagcgaat cgtgatgtgg 1321 attgttgctt gattccagag tctccatttt tccttgaagg aaagggtggg ctctttgagt 1381 ttattgaaga acgactcaaa gagaataggc acatggttat tgtgatagct gaaggagctg 1441 gacaggatta tgttgctcaa agcatgcgtg catctgaaac taaagacgcc tcaggaaata 1501 gactcttgct tgatgttggt ctatggttga ctcaacagat aaaggatcac tttacaaatg 1561 ttcggaaaat gatgataaat atgaagtaca tagacccaac gtatatgata agagcaatac 1621 cgagtaacgc atcagacaat gtctattgca ctcttcttgc ccaaagtgca gttcatggag 1681 caatggctgg gtactcaggt ttcactgtag gaccagttaa cagtagacat gcttacatcc 1741 caatttctgt gacggaagtg acaaatacgg tgaagttaac tgataggatg tgggctagac 1801 tccttgcatc gacaaatcaa ccgagtttct tgactggtga aggagcattg cagaatgtga 1861 tcgacatgga aactcaagaa aagatcgata acatgaagat ctcttctatc taaTAAATGG

1921 AGGCGCTCGT TGATCTGAGC CTTGCCCCCT GACGAACGGG GTGGATGGA AGATACTGCT

1981 CTCAAGTGCT GAAGCGGTAG CTTAGCTCCC CGTTTCGTGC TGATCAGTCT TTTTCAACAC

2041 GTAAAAAGCG GAGGAGTTTT GCAATTTTGT TGGTTGTAAC GATCCTCCGT TGATTTTGGC

2101 CTCTTTCTCC ATGGGCGGGC TGGGCGTATT TGAAGCggtt ctctcttctg ccgtta
//

Sequence No. 16
Example 16: a designer Nia1-promoter-linked Starch-Synthase-iRNA
DNA construct (860 bp)
   1 agaaaatctg gcaccacacc TATATGGTAG GGTGCGAGTG ACCCCGCGCG ACTTGGAGCT

61 CGATGGCCCC GGGTTGTTTG GGGCGTCCGC CTCTCGCGCT ATTCTGAGCT GGAGACCGAG

121 GCGCATGAAA ATGCATTCGC TTCCATAGGA CGCTGCATTG TGGCTTGAAG GTTCAAGGGA

181 AGGGTTCAAA CGACCCCGCC GTACGAACTT TTGTCGGGGG GCGCTCCCGG CCCCGGGCTC

241 TTGTGCGCGC ATTAGGGCTT CGGGTCGCAA GCAAGACGAT ACatgccagc cggctcacca 301 ccgccaccag cggcttgcgg gggtccacct ccaggcccag accttctgc agaaactcct 361 tgcacagcgc cttcccggcg gggcggtcgg cgtcgaagtt ggctggcagc agcgcgtcag
```

```
421 tggccgggtt ccactcctca cagtcaatgc cgttcaggat gccgtggaac ttggagcgca 481 gctcggggcg cgcgaaggtg gatctcgccg tcccagcggt agcccttggg cacctcgatg 541 tcgcattcgt gcttgaggcc ctcaatctgg tccttgggca ggcactcgta gaacggcagc 601 atgaccgtca cgaagtgTAA ATGGAGGCGC TCGTTGATCT GAGCCTTGCC CCCTGACGAA

661 CGGCGGTGGA TGGAAGATAC TGCTCTCAAG TGCTGAAGCG GTAGCTTAGC TCCCCGTTTC

721 GTGCTGATCA GTCTTTTTCA ACACGTAAAA AGCGGAGGAG TTTTGCAATT TTGTTGGTTG

781 TAACGATCCT CCGTTGATTT TGGCCTCTTT CTCCATGGGC GGGCTGGGCG TATTTGAAGC 841 ggttctctct tctgccgtta
//

Sequence No. 17
Example 17: a designer HydA1-promoter-linked Starch-Synthase-iRNA
DNA construct (1328 bp)
    1 AGAAAATCTG GCACCACACC gagctgtcat gcgttgttcc gttatgtgtc gtcaaacgcc 61 ttcgagcgct gcccggaaca atgcgtacta gtataggagc catgaggcaa gtgaacagaa 121 gcgggctgac tggtcaaggc gcacgatagg gctgacgagc gtgctgacgg ggtgtaccgc 181 cgagtgtccg ctgcattccc gccggattgg gaaatcgcga tggtcgcgca taggcaagct 241 cgcaaatgct gtcagcttat cttacatgaa cacacaaaca ctctcgcagg cactagcctc 301 aaATGAAGAG CTTCATGCGG AGGGATGCGC TCGGCGCGGG GCTCCGCGGT GCAGCCAGCA

361 CAAAGCCCGT CTCAAGGGTC GCCAGCGTGA GGCCTGCGCC TACCGCCTAC CGCACTGCCT

421 GCCAAGTTGC GAAGGTGGAT GAAATGGTGT CGGTGGATGA GGAGCTTACT CGTCTCCGCA

481 AGGAGAACGA GCTCCTGCGC GCCCAACTGG CGCTGTACCA GCAGAACCAG CAGCCGTCCG

541 TGGGTGCCGC TGCCGTTGCC CCGCCTGCTG CCGCCACGAA GGTGCTGGAG AAGCCGGCGC

601 CGtaagtaac ctaaCGGTGA GCAGCATGCA ATATTTTAGC GTCGATACTC GGAAACTATA

661 GGAGCGCATC AGCCGACCGA TGTTCGCGTT GCTGTCGCAG GCCCAACCGT GCCACCGCCG

721 TGGTGTGCAA GGCGCAGAAG GCGGCCAGGC CGCCGCTGCC GCTGCTCTGG CCAtaagtaa 781 cctaaCGGCG CCGGCTTCTC CAGCACCTTC GTGGCGGCAG CAGGCGGGGC AACGGCAGCG

841 GCACCCACGG ACGGCTGCTG GTTCTGCTGG TACAGCGCCA GTTGGGCGCG CAGGAGCTCG

901 TTCTCCTTGC GGAGACGAGT AAGCTCCTCA TCCACCGACA CCATTTCATC CACCTTCGCA

961 ACTTGGCAGG CAGTGCGGTA GGCGGTAGGC GCAGGCCTCA CGCTGGCGAC CCTTGAGACG

1021 GGCTTTGTGC TGGCTGCACC GCGGAGCCCC GCGCCGAGCG CATCCCTCCG CATCAAGCTC

1081 TTCATtaaat ggaggcgctc gttgatctga gccttgcccc ctgacgaacg gcggtggatg 1141 gaagatactg ctctcaagtg ctgaagcggt agcttagctc ccgtttcgt gctgatcagt 1201 cttttcaac acgtaaaaag cggaggagtt ttgcaatttt gttggttgta acgatcctcc 1261 gttgattttg gcctctttct ccatgggcgg gctgggcgta tttgaagcGG TTCTCTCTTC

1321 TGCCGTTA
//

Sequence No. 18
Example 18: a designer Amylase DNA construct (1889 bp)
    1 agaaaatctg gcaccacacc ATGGTAGGGT GCGAGTGACC CCGCGCGACT TGGAAGGGTT

61 CAAACGACCC CGCCGTACGA ACTTTTGTCG GGGGCGCTC CCGGATGGTA GGGTGCGAGT

121 GACCCCGCGC GACTTGGAAG GGTTCAAACG ACCCCGCCGT ACGAACTTTT GTCGGGGGGC
```

```
 181 GCTCCCGGct cgagcatATG GCCGCCGTCA TTGCCAAGTC CTCCGTCTCC GCGGCCGTGG

241 CTCGCCCGGC CCGCTCCAGC GTGCGCCCCA TGGCCGCGCT GAAGCCCGCC GTCAAGGCTG

301 CCCCCGTGGC TGCCCCGGCT CAGGCCAACC AGatggcgaa caaacacatg tccctttctc 361 tcttcatcgt cctccttggc ctctcgtgca gcttggcctc cgggcaagtc ctgtttcagg 421 gttttaactg ggagtcgtgg aagcacaatg gcgggtggta caacttcctg atgggcaagg 481 tggacgacat cgccgccgct ggcgtcacgc acgtgtggcc cccccggcg tcgcagtccg 541 tcgccgagca agggtacatg ccgggccggc tctacgacct ggacgcctcc aagtacggca 601 acaaggcgca gctcaagtcc ctcatcggcg cgctccacgg caagggcgtc aaggccatcg 661 ccgacatcgt catcaaccac cgcacggcgg agcgcaagga cggccgggc atctactgca 721 tcttcgaggg cggcaccccg gacgcgcgcc tcgactgggg cccccacatg atctgccgcg 781 acgaccggcc ctacgccgac ggcaccggca acccggacac cggcgccgac ttcggggccg 841 cgccggacat cgaccacctc aacccgcgcg tccagaagga gctcgtcgag tggctcaact 901 ggctcaggac cgacgtcggc ttcgacggct ggcgcttcga cttcgccaag ggctactccg 961 cggacgtggc caagatctac gtcgaccgct ccgagcccag cttcgccgtc gccgagatat 1021 ggacgtcgct ggcgtacggc ggggacggca agccgaacct caaccaggac ccgcaccggc 1081 aggagctggt gaactgggtg aacaaggtgg gcggctccgg ccccgccacc acgttcgact 1141 tcaccaccaa gggcatcctc aacgtggccg tggagggcga gctgtggcgc ctgcgcggca 1201 ccgacggcaa ggcgccgggc atgatcgggt ggtggccggc caaggcggtg accttcgtcg 1261 acaaccacga caccggctcc acgcagcaca tgtggccctt cccttccgac agggtcatgc 1321 agggatatgc ctacatcctc acgcacccag ggaccccatg catcttctac gatcatttct 1381 tcgactgggg cttgaaggag gagatcgatc gtctggtgtc aatcaggacc cgacagggga 1441 tacacagtga gagcaagctg cagatcatgg aggccgacgc cgacctttac cttgccgaga 1501 tcgacggcaa ggtcatcgtc aagctcgggc aagatacga tgtcggacac ctcattcctg 1561 aaggcttcaa ggtggtcgcg catggcaatg actatgccgt atgggagaaa gtataaGGCT 1621 GCTGCCCCGG CTGCTGCtaa tctagaTAAA TGGAGGCGCT CGTTGATCTG AGCCTTGCCC

1681 CCTGACGAAC GGCGGTGGAT GGAAGATACT GCTCTCAAGT GCTGAAGCGG TAGCTTAGCT

1741 CCCCGTTTCG TGCTGATCAG TCTTTTTCAA CACGTAAAAA GCGGAGGAGT TTTGCAATTT

1801 TGTTGGTTGT AACGATCCTC CGTTGATTTT GGCCTCTTTC TCCATGGGCG GGCTGGGCGT

1861 ATTTGAAGCg gttctctctt ctgccgtta
//

Sequence No. 19
Example 19: a designer Starch-Phosphorylase DNA construct (3089 bp)
   1 AGAAAATCTG GCACCACACC atggtagggt gcgagtgacc ccgcgcgact tggaagggtt 61 caaacgaccc cgccgtacga acttttgtcg gggggcgctc ccggatggta gggtgcgagt 121 gaccccgcgc gacttggaag ggttcaaacg accccgccgt acgaactttt gtcggggggc 181 gctcccggAT GGCCGCCGTC ATTGCCAAGT CCTCCGTCTC CGCGGCCGTG GCTCGCCCGG

241 CCCGCTCCAG CGTGCGCCCC ATGGCCGCGC TGAAGCCCGC CGTCAAGGCT GCCCCCGTGG

301 CTGCCCCGGC TCAGGCCAAC CAGatggcgg atgcgaaagc aaacggaaag aatgaggcgg 361 ccaaactggc gaaaattccg gcggctgcga atccattggc taatgaacca tcggcgattg 421 catcaaatat aagttaccac gtgcagtaca gtcctcattt ctcgccgact aagttcgagc
```

-continued

```
 481 cggagcaagc tttctttgcc acggcggagg ttgtccgcga tcgtcttatt caacaatgga
 541 atgagacata ccaccatttt aataaagttg atccgaagca aacatactac ctatcaatgg
 601 aatttcttca aggaaggact ttgactaatg caattggcag tttggacatt cagaatgcat
 661 atgctgatgc tttaaataat ttggggcatg tccttgagga gatagctgaa caggaaaaag
 721 atgctgcact aggaaatggt gggctgggca ggctagcttc atgcttctta gactccatgg
 781 caacattgaa tttgcctgca tggggttatg gtttgagata ccggtatggg ctgttcaagc
 841 agaagatcac caagcagggt caagaagaag ttgctgaaga ttggcttgag aaatttagtc
 901 cttgggaagt tgtcaggcat gatgtggtat ttccggtcag atttttggg agtgttatgg
 961 ttaatccaaa tggaacgaga aaatggggttg ggggtgaagt tgtccaagcc gtagcttatg
1021 atataccaat tccagggtac aaaaccaaga acactatcag tcttcgtctc tgggacgcta
1081 aagctagcgc tgaggatttc aatttatttc agtttaatga tggacaatac gaatctgctg
1141 cacagcttca ttctcgagct caacagattt gtgctgtgct ctaccccggg gattctactg
1201 aagaagggaa gcttttaagg ctgaaacaac aattctttct ctgcagtgct tcacttcagg
1261 atatgattct tagattcaag gagaggaaaa gtggaaggca gtggtctgaa tttcccagca
1321 aggtagctgt acaactgaat gatactcatc caacacttgc aattccagag ttgatgcgat
1381 tgctaatgga tgaggaagga cttggatggg atgaagcatg ggatataaca acaaggactg
1441 ttgcttatac caatcacaca gtacttcctg aagcacttga gaagtggtca caagcagtaa
1501 tgtggaagct tcttcctcgc catatggaaa taattgaaga gattgacaag agattcattg
1561 caatggtccg ctccacaagg agtgaccttg agagtaagat tcccagcatg tgcatcttgg
1621 ataataatcc caaaaagccg gttgttagga tggcaaactt atgtgtagta tctgcgcata
1681 cggtaaatgg tgttgctcag ttgcacagtg atatcttaaa ggccgacttg ttcgctgact
1741 atgtttctct atggccaaac aaactccaaa ataaaactaa tggcattact cctcgtcgat
1801 ggctccggtt ttgcaatcct gagctcagca aaattatcac aaaatggtta aaaaccgatc
1861 agtgggttac gaaccttgac ctgcttgtag gtcttcgtca gtttgctgac aacacagaac
1921 tccaagctga atgggaatct gctaagatgg ccagtaagaa acatttggca gactacatat
1981 ggcgagtaac cggtgtaacg attgatccta atagcttatt tgacatacaa gtcaagcgca
2041 ttcatgaata caagagacaa ctgctaaata tttttgggcgc aatctacaga tacaagaagt
2101 tgaaggagat gagccctcag gagcggaaga aaactactcc acgcaccatt atgtttggag
2161 ggaaagcatt tgcaacatat acaaacgcaa aaagaatagt aaagttggtt aatgatgttg
2221 gtgaagtcgt caacaccgat cctgaggtca atagttattt gaaggtggta tttgttccaa
2281 attacaatgt ctctgttgcg gagttgctta ttccaggaag tgagctatct cagcatatta
2341 gcacagcagg catggaggca agtggcacaa gcaacatgaa attttctcta aatggttgcc
2401 tcattatagg aacattggat ggagctaatg tggaaatcag gcaggagata ggagaggaga
2461 atttctttct ctttggtgca ggagcagacc aagtccctaa gctgcggaag gaaagagaag
2521 atggattgtt caaaccagat cctcggtttg aagaggccaa gcaatttata agaagtggag
2581 catttggaag ctatgactac aacccgcttc ttgattccct ggaggggaac actggttatg
2641 gtcgtggtga ttatttttcta gttggttatg acttcccaag ttacttagag gctcaggaca
2701 gagttgacca agcttacaag gaccggaaga agtggctgaa gatgtctata ttaagtacag
2761 ctggcagtgg gaaattcagc agtgatcgca caattgcaca gtatgctaag gaaatctgga
2821 acataacaga atgccgtaca tcatgaTAAA TGGAGGCGCT CGTTGATCTG AGCCTTGCCC
```

```
2881 CCTGACGAAC GGCGGTGGAT GGAAGATACT GCTCTCAAGT GCTGAAGCGG TAGCTTAGCT

2941 CCCCGTTTCG TGCTGATCAG TCTTTTTCAA CACGTAAAAA GCGGAGGAGT TTTGCAATTT

3001 TGTTGGTTGT AACGATCCTC CGTTGATTTT GGCCTCTTTC TCCATGGGCG GGCTGGGCGT

3061 ATTTGAAGCg gttctctctt ctgccgtta
//

Sequence No. 20
Example 20: a designer Hexose-Kinase DNA construct (1949 bp)
   1 AGAAAATCTG GCACCACACC atggtagggt gcgagtgacc ccgcgcgact tggaagggtt 61 caaacgaccc cgccgtacga acttttgtcg gggggcgctc ccggatggta gggtgcgagt 121 gaccccgcgc gacttggaag ggttcaaacg accccgccgt acgaactttt gtcgggggc 181 gctcccggAT GGCCGCCGTC ATTGCCAAGT CCTCCGTCTC CGCGGCCGTG GCTCGCCCGG

241 CCCGCTCCAG CGTGCGCCCC ATGGCCGCGC TGAAGCCCGC CGTCAAGGCT GCCCCCGTGG

301 CTGCCCCGGC TCAGGCCAAC CAGatggcta taacaccccg ccgaaaacct tcccggaagg 361 gatcaatggc tgatatgccg aaggatgtgc ttgaccagct caagacgctg gaagagctct 421 tcacagttga ccaggagaag ctgaagcaga tcgttgagca tttcatcaag gagttacaga 481 agggcctcag tgtcgaaggc ggaaacattc ccatgaacgt gacttgggtt ctgggatttc 541 ccactggcca tgagaaaggt acatttctgg ctctggacat gggggggcacc aacctgcgcg 601 tctgcgaaat tgagctctcc gaagagaagg gcgagtttga tgtcacacag tccaagtatc 661 gaatccccga agagctcaag agcggtgaat catcagaact atgggaatat attgccgact 721 gtgtacagca gttcatagaa tactaccatg acggttgcac ggctttgcca gacctgccgc 781 tgggctttac cttttcgtac cctgctactc aagaatatgt tgaccacggt gtcctacaga 841 gatggaccaa gggttttgat attgacggcg tcgagggcaa agacgtcgtc ccaatgttag 901 aagaagcttt ggctaagaag gttaaaaatt cagctctttc cccatttttc tttggctata 961 tggtgctaat tactttacag ggtctcccca ttaaagttgc cgctctagta aacgacacga 1021 ctggcacact tattgcttcc gcctacactg acccagagat gaaaatcggc tgtatcttcg 1081 gcacaggcgt caacgccgcc tacatggaaa atgcgggctc tatccctaaa atagcccact 1141 acaatttacc tcccgacacc ccagtcgcta tcaactgcga atacggcgcc ttcgacaacg 1201 aactcattgt cctcccccga acgcagtatg acgacgtatc caactacgt aaaccatact 1261 ccctggactc ctccttccta gccttcatcg aagaagatcc cttcgagaac ctgtcagaaa 1321 cgcgagatct cttcgaacgc accctgggga tctacgcatt gccctcggag ctagaattct 1381 gcagacgcct ggcggaattg atcggcacac gtgccgcacg cctctccgct gcggtgttg 1441 cggccatctg caagaagaaa aatatcaccc attgccatgt cggagcggac gggtcggtgt 1501 tcgagaagta cccgcatttc aaggccaggg gcgccagagc cctgcgggag atccttgact 1561 ggccagatag tgaaccggat cgggttgtga tgagcggagc ggaggatggg tctggcgttg 1621 gtgcggcgct tattgcggct ttgacgcttg agagggttaa acaagcttct tgggaatgga 1681 agtacatcgg aagcggtctg tcttaaTAAA TGGAGGCGCT CGTTGATCTG AGCCTTGCCC

1741 CCTGACGAAC GGCGGTGGAT GGAAGATACT GCTCTCAAGT GCTGAAGCGG TAGCTTAGCT

1801 CCCCGTTTCG TGCTGATCAG TCTTTTTCAA CACGTAAAAA GCGGAGGAGT TTTGCAATTT

1861 TGTTGGTTGT AACGATCCTC CGTTGATTTT GGCCTCTTTC TCCATGGGCG GGCTGGGCGT

1921 ATTTGAAGCg gttctctctt ctgccgtta
//
```

Sequence No. 21
Example 21: a designer Phosphoglucomutase DNA construct (2249 bp)

```
   1 AGAAAATCTG GCACCACACC atggtagggt gcgagtgacc ccgcgcgact tggaagggtt
  61 caaacgaccc cgccgtacga acttttgtcg gggggcgctc ccggatggta gggtgcgagt
 121 gaccccgcgc gacttggaag ggttcaaacg accccgccgt acgaactttt gtcgggggcgc
 181 gctcccggAT GGCCGCCGTC ATTGCCAAGT CCTCCGTCTC CGCGGCCGTG GCTCGCCCGG
 241 CCCGCTCCAG CGTGCGCCCC ATGGCCGCGC TGAAGCCCGC CGTCAAGGCT GCCCCCGTGG
 301 CTGCCCCGGC TCAGGCCAAC CAGatgtccg atttctccgt ccagaccatt gccaccacgg
 361 ccttcacaga ccaaaagcct ggaacctctg gtctcagaaa gaaagttact gtgtttcaac
 421 agcctcacta cactgaaaac ttcattcagg ctattctcga tgccattccg gaaggtgccc
 481 aaggtgccac tcttgttgta ggaggtgatg ccgtttcta caacgacaag gtcatcaact
 541 tgatcgccaa aatcgcctcg gccaacggag tttccaagtt gattttgggt caagacggga
 601 ttctttccac tccagcaact tcgcatgtaa tcaggatcag gggtgcaact ggaggaatta
 661 ttctcactgc ttcacacaac cccggaggcc ccaaaaacga tttgggtatt aagtacaact
 721 tgggaaacgg tgcaccagct ccagaatcgg ttaccaacaa gatctatgat gtctccaagg
 781 aattgacttc gtacaagctc attgatttac ccgacattga tttgtccaaa acccagaccg
 841 tgcaattggg ccctcttgaa gtggaaatca ttgactccac ctctgattac gtagccatgt
 901 tgaaggatat ctttgacttc cccttgatca agtcgttcct cgagactgcc actaaggagc
 961 agggattcaa ggttttattt gattcgctca atggtgtcac tggcccctac ggctacaaga
1021 tcttcgttga agaattagga ttgcctctta actcaatcca aaattaccac ccattgcctg
1081 actttggtgg tttacaccca gatccaaact tgacctatgc tcatactttg gtcgagaggg
1141 tcgataagga gaatattgcc tttggtgctg catctgatgg tgacggtgac agaaacatga
1201 tctacggtgc tggtacccttt gtttcgcctg gtgactctgt agccatcatc tcggaatacg
1261 ccgattccat cccttacttc aagaagcaag gtgtctacgg ttttggccaga tccatgccta
1321 cctctggagc catcgatttg gtagcaaagg ctaaaggatt gaatgtttac gaagtgccaa
1381 ccggttggaa gttcttctgc aacctttcg acgctgacaa gttgagtatc tgtggtgaag
1441 agtcgtttgg aacaggctcc aaccacatca gagaaaagga cggcctttgg gctgtagttg
1501 cctggttgaa cgtgctagca gattacaacg tcaagaatcc agaatccaag acatctattt
1561 ctgtagtgca gaactcgttt tggaagaaat acggaagaac tttcttcact agatatgact
1621 acgaaaacgt atcgtctgaa ggtgctgccg agctcatcaa cttgttgtct tctattgttg
1681 actctaagaa accaggaagt agcttagctg atggctacgt cgtcaaggaa gctgctaact
1741 tctcgtacac cgatttggac ggctctgttt cgtccaacca aggtttgttc atcaagtttg
1801 aaagcggctt gagattcata gtaagattgt ctggtactgg atcatccggt gctacagtca
1861 gattatatct cgaaaagcac tctgccgacg aatccaccta tggcttaggc gtagaccagt
1921 acttagttga tgacatcaag tttgtcttgg acttgttgaa gttcaagcag ttcttgggaa
1981 aggatgaacc agatgttcgt acctagTAAA TGGAGGCGCT CGTTGATCTG AGCCTTGCCC
2041 CCTGACGAAC GGCGGTGGAT GGAAGATACT GCTCTCAAGT GCTGAAGCGG TAGCTTAGCT
2101 CCCCGTTTCG TGCTGATCAG TCTTTTTCAA CACGTAAAAA GCGGAGGAGT TTTGCAATTT
2161 TGTTGGTTGT AACGATCCTC CGTTGATTTT GGCCTCTTTC TCCATGGGCG GGCTGGGCGT
2221 ATTTGAAGCg gttctctctt ctgccgtta
//
```

Sequence No. 22
Example 22: a designer Glucosephosphate-Isomerase DNA construct (2231 bp)

```
   1 AGAAAATCTG GCACCACACC atggtagggt gcgagtgacc ccgcgcgact tggaagggtt
  61 caaacgaccc cgccgtacga acttttgtcg ggggcgctc ccggatggta gggtgcgagt
 121 gaccccgcgc gacttggaag ggttcaaacg accccgccgt acgaactttt gtcgggggc
 181 gctcccggAT GGCCGCCGTC ATTGCCAAGT CCTCCGTCTC CGCGGCCGTG GCTCGCCCGG
 241 CCCGCTCCAG CGTGCGCCCC ATGGCCGCGC TGAAGCCCGC CGTCAAGGCT GCCCCCGTGG
 301 CTGCCCCGGC TCAGGCCAAC CAGatgtcca ataactcatt cactaacttc aaactggcca
 361 ctgaattgcc agcctggtct aagttgcaaa aaatttatga atctcaaggt aagactttgt
 421 ctgtcaagca agaattccaa aaagatgcca agcgttttga aaaattgaac aagactttca
 481 ccaactatga tggttccaaa atcttgttcg actactcaaa gaacttggtc aacgatgaaa
 541 tcattgctgc attgattgaa ctggccaagg aggctaacgt caccggtttg agagatgcta
 601 tgttcaaagg tgaacacatc aactccactg aagatcgtgc tgtctaccac gtcgcattga
 661 gaaacagagc taacaagcca atgtacgttg atggtgtcaa cgttgctcca gaagtcgact
 721 ctgtcttgaa gcacatgaag gagttctctg aacaagttcg ttctggtgaa tggaagggtt
 781 ataccggtaa gaagatcacc gatgttgtta acatcggtat tggtggttcc gatttgggtc
 841 cagtcatggt cactgaggct ttgaagcact acgctggtgt cttggatgtc cacttcgttt
 901 ccaacattga cggtactcac attgctgaaa ccttgaaggt tgttgaccca gaaactactt
 961 tgtttttgat tgcttccaag actttcacta ccgctgaaac tatcactaac gctaacactg
1021 ccaagaactg gttcttgtcg aagacaggta atgatccatc tcacattgct aagcatttcg
1081 ctgctttgtc cactaacgaa accgaagttg ccaagttcgg tattgacacc aaaaacatgt
1141 ttggtttcga agttgggtc ggtggtcgtt actctgtctg gtcggctatt ggtttgtctg
1201 ttgccttgta cattggctat gacaactttg aggctttctt gaagggtgct gaagccgtcg
1261 acaaccactt cacccaaacc ccattggaag acaacattcc attgttgggt ggtttgttgt
1321 ctgtctggta caacaacttc tttggtgctc aaacccattt ggttgctcca ttcgaccaat
1381 acttgcacag attcccagcc tacttgcaac aattgtcaat ggaatctaac ggtaagtctg
1441 ttaccagagg taacgtgttt actgactact ctactggttc tatcttgttt ggtgaaccag
1501 ctaccaacgc tcaacactct ttcttccaat tggttcacca aggtaccaag ttgattccat
1561 ctgatttcat cttagctgct caatctcata acccaattga gaacaaatta catcaaaaga
1621 tgttggcttc aaacttcttt gctcaagctg aagctttaat ggttggtaag gatgaagaac
1681 aagttaaggc tgaaggtgcc actggtggtt tggtcccaca caaggtcttc tcaggtaaca
1741 gaccaactac ctctatcttg gctcaaaaga ttactccagc tactttgggt gctttgattg
1801 cctactacga acatgttact ttcactgaag gtgccatttg aatatcaac tctttcgacc
1861 aatggggtgt tgaattgggt aaagtcttgg ctaaagtcat cggcaaggaa ttggacaact
1921 cctccaccat ttctacccac gatgcttcta ccaacggttt aatcaatcaa ttcaaggaat
1981 ggatgtgaTA AATGGAGGCG CTCGTTGATC TGAGCCTTGC CCCCTGACGA ACGGCGGTGG
2041 ATGGAAGATA CTGCTCTCAA GTGCTGAAGC GGTAGCTTAG CTCCCCGTTT CGTGCTGATC
2101 AGTCTTTTTC AACACGTAAA AAGCGGAGGA GTTTTGCAAT TTTGTTGGTT GTAACGATCC
2161 TCCGTTGATT TTGGCCTCTT TCTCCATGGG CGGGCTGGGC GTATTTGAAG Cggttctctc
2221 ttctgccgtt a
//
```

REFERENCES

1. Gfeller, R. aid M. Gibbs (1984), "Fermentative metabolism of *Chlamydomonas reinhardtii*," Plant Physiol. 75: 212-218.
2. Cinco, R. M., U. M. MacInnis, and E. Greenbaum (1993), "The role of carbon dioxide in light-activated hydrogen production by *Chlamydomonas reinhardtii*," Photosynthesis Research 38: 27-33.
3. Quinn, J. M., P. Barraco, M. Ericksson and S. Merchant (2000), "Coordinate copper- and oxygen-responsive Cyc6 and Cpx1 expression in *Chlamydomonas* is mediated by the same element," J Biol Chem 275: 6080-6089.
4. Teramoto, H., T. Ono and J. Minigawa (2001), "Identification of Lhcb gene family encoding the light-harvesting chlorophyll-a/b proteins of photosystem 11 in *Chlamydomonas reinhardtii*," Plant Cell Physiol 42(8): 849-856.
5. Pattanayak, D., S. Chatterjee (1998), "Nicotinamide adenine dinucleotide phosphate phosphatase facilitates dark reduction of nitrate: regulation by nitrate and ammonia," Biologia Plantarium 41(1): 75-84.
6. Muto, S. S. Miyachi, H. Usuda, G. Edwards and J. Bassham (1981), "Light-induced conversion of nicotinamide adenine dinucleotide to nicotinamide adenine dinucleotide phosphate in higher plant leaves," Plant Physiology 68(2): 324-328.
7. Matsumura-Kadota, H., S. Muto, S. Miyachi (1982), "Light-induced conversion of NAD+ to NADP+ in *Chlorella* cells," Biochimica Biophysica Acta 679(2): 300-300.
8. Liszewski, K. (2003), Progress in RNA interference, Genetic Engineering News, Vol. 23, number 11, pp. 1-59.
9. Fire A., Xu S. Montgomery M K, Kostas S A, Driver S E, Mello C C (1998), "Potent and specific genetic interference by double-stranded RNA in *Caenorhabditis elegans*," Nature 391(6669): 806-11.
10. Dykxhoom D M, Novina C D, Sharp P A (2003), "Killing the messenger: short RNAs that silence gene expression," Nat Rev Mol Cell Biol. 4(6): 457-467.
11. Lee, James W., Stephen L. Blankinship and Elias Greenbaum (1995). "Temperature effect on production of hydrogen and oxygen by *Chlamydomonas* cold strain CCMP 1619 and wild type 137c," Applied Biochemistry aid Biotechnology 51/52: 379-386.
12. Lee, James W., Laurens Mets, and Elias Greenbaum (2002), "Improvement of photosynthetic efficiency at high light intensity through reduction of chlorophyll antenna size," Applied Biochemistry and Biotechnology 98-100: 37-48.

---

What is claimed is:

1. A method for photosynthetic production of ethanol comprising growing a transgenic designer plant or plant cells in a liquid medium, wherein the plant or plant cells are genetically engineered to express a set of enzymes in the chloroplast that act on an intermediate product of the Calvin cycle and convert the intermediate product into ethanol by utilizing NADPH and ATP generated from photosynthesis in said plant or plant cells; and recovering ethanol from said liquid medium.

2. The method according to claim 1, wherein said plant is an aquatic or non-aquatic plant.

3. The method of claim 2, wherein said plant is an alga.

4. The method of claim 1, wherein said set of enzymes consists of phosphoglycerate mutase, enolase, pyruvate kinase, pyruvate decarboxylase, and alcohol dehydrogenase.

5. The method of claim 1, wherein said set of enzymes consists of glyceraldehyde-3-phosphate dehydrogenase, phosphoglycerate kinase, phosphoglycerate mutase, enolase, pyruvate kinase, pyruvate decarboxylase, and alcohol dehydrogenase.

6. The method of claim 1, wherein said set of enzymes consists of aldolase, triose phosphate isomerase, glyceraldehyde-3-phosphate dehydrogenase, phosphoglycerate kinase, phosphoglycerate mutase, enolase, pyruvate kinase, pyruvate decarboxylase, and alcohol dehydrogenase.

7. The method of claim 1, wherein said set of enzymes consists of phosphofructose kinase, aldolase, triose phosphate isomerase, glyceraldehyde-3-phosphate dehydrogenase, phosphoglycerate kinase, phosphoglycerate mutase, enolase, pyruvate kinase, pyruvate decarboxylase, and alcohol dehydrogenase.

8. The method of claim 1, wherein said set of enzymes consists of amylase, starch phosphorylase, hexokinase, phosphoglucomutase, glucose-phosphate isomerase, phosphofructose kinase, aldolase, triose phosphate isomerase, glyceraldehyde-3-phosphate dehydrogenase, phosphoglycerate kinase, phosphoglycerate mutase, enolase, pyruvate kinase, pyruvate decarboxylase, and alcohol dehydrogenase.

9. The method of claim 1, wherein said set of enzymes is genetically engineered to be inserted into the chloroplasts of the transgenic designer plant or plant cells, wherein said insertion is directed by a stroma signal peptide.

10. The method of claim 1, wherein the expression of a said enzyme is controlled by an inducible promoter.

11. The method of claim 10, wherein said promoter is selected from the group consisting of hydrogenase promoters and nitrate reductase promoters.

12. The method of claim 1, wherein the plant or plant cells are genetically engineered to also contain a DNA construct coding for at least one enzyme that facilitates the NADPH/NADH conversion for enhanced photobiological production of ethanol.

13. The method of claim 1, wherein the plant or plant cells are genetically engineered to also inactivate starch-synthesis activity.

14. The method of claim 1, wherein the plant or plant cells are genetically engineered to also inducibly express an additional set of designer enzymes that facilitate starch degradation and glycolysis in the stroma region of the chloroplast.

15. The method of claim 4, wherein said alcohol dehydrogenase utilizes NADPH.

16. The method according to any one of claims 5-8, wherein said glyceraldehydes-3-phosphate dehydrogenase is NAD+-dependent.

17. The method of claim 12, wherein said at least one enzyme is an NADPH phosphatase or an NAD kinase.

* * * * *